United States Patent
Daniel

(10) Patent No.: US 11,006,949 B2
(45) Date of Patent: May 18, 2021

(54) METHOD AND APPARATUS FOR A SHAPE MEMORY IMPLANT

(71) Applicant: DEPUY SYNTHES PRODUCTS, INC., Raynham, MA (US)

(72) Inventor: Steffan Daniel, Zuchwil (CH)

(73) Assignee: DePuy Synthesis Products, Inc., Raynham, MA (US)

(*) Notice: Subject to any disclaimer, the term of this patent is extended or adjusted under 35 U.S.C. 154(b) by 183 days.

(21) Appl. No.: 16/225,336

(22) Filed: Dec. 19, 2018

(65) Prior Publication Data
US 2020/0197005 A1    Jun. 25, 2020

(51) Int. Cl.
| | |
|---|---|
| A61B 17/06 | (2006.01) |
| A61B 17/064 | (2006.01) |
| A61B 17/068 | (2006.01) |
| A61B 17/88 | (2006.01) |
| A61B 17/10 | (2006.01) |
| A61B 17/00 | (2006.01) |

(52) U.S. Cl.
CPC ........ *A61B 17/0642* (2013.01); *A61B 17/068* (2013.01); *A61B 17/8872* (2013.01); *A61B 17/10* (2013.01); *A61B 2017/00526* (2013.01); *A61B 2017/00867* (2013.01); *A61B 2017/0645* (2013.01)

(58) Field of Classification Search
CPC ... A61B 17/88; A61B 17/8872; A61B 17/064; A61B 17/068
See application file for complete search history.

(56) References Cited

U.S. PATENT DOCUMENTS

| | | |
|---|---|---|
| 5,993,476 A | 11/1999 | Groiso |
| 6,187,009 B1 | 2/2001 | Herzog et al. |
| 6,554,852 B1 | 4/2003 | Oberlander |
| 8,679,123 B2 | 3/2014 | Kinmon et al. |
| 8,801,786 B2 | 8/2014 | Bernard et al. |
| 8,951,254 B2 | 2/2015 | Mayer et al. |
| 9,585,656 B2 | 3/2017 | Taber et al. |

(Continued)

FOREIGN PATENT DOCUMENTS

FR    2668921 A1    5/1992

OTHER PUBLICATIONS

PHILOS with Augmentation Surgical Technique, DePuy Synthes, Synthes GmbH, Eimattstrasse 3, 4436 Oberdorf, Switzerland, May 2017.

(Continued)

*Primary Examiner* — Christopher J Beccia
(74) *Attorney, Agent, or Firm* — Christopher L. Makay

(57) ABSTRACT

An apparatus for fixating bone includes an orthopedic implant. The orthopedic implant may be manufactured from a shape memory material such that the orthopedic implant is moveable between a natural shape and an insertion shape. The orthopedic implant defines at least a first cannulation therethrough adapted to deliver a bone augmentation material to the bone. The orthopedic implant implants into the bone in its insertion shape. After implantation of the orthopedic implant, the first cannulation facilitates delivery into the bone of a bone augmentation material that augments the bone. The orthopedic implant once implanted attempts to transition from its insertion shape to its natural shape such that the orthopedic implant fixates the bone.

20 Claims, 33 Drawing Sheets

(56) References Cited

U.S. PATENT DOCUMENTS

| | | |
|---|---|---|
| 10,117,647 B2 | 11/2018 | Cheney |
| 2002/0143329 A1 | 10/2002 | Serhan et al. |
| 2007/0093839 A1 | 4/2007 | Beckendorf et al. |
| 2008/0065154 A1 | 3/2008 | Allard et al. |
| 2016/0000489 A1* | 1/2016 | Kaloostian ........... A61B 17/866 606/323 |
| 2016/0015384 A1* | 1/2016 | Roedl ................ A61B 17/0642 606/75 |
| 2016/0066907 A1 | 3/2016 | Cheney et al. |
| 2016/0074037 A1 | 3/2016 | Cheney et al. |
| 2017/0065275 A1* | 3/2017 | Cheney .............. A61B 17/0642 |

OTHER PUBLICATIONS

TFN Advanced Proximal Femoral Nailing System, DePuy Synthes, Synthes GmbH, Eimattstrasse 3, 4436 Oberdorf, Switzerland, May 2016.
European Search Report dated Apr. 2, 2020 received in connection with EP application counterpart to U.S. Appl. No. 16/225,336.

* cited by examiner

METHOD AND APPARATUS FOR A SHAPE MEMORY IMPLANT

BACKGROUND OF THE INVENTION

1. Field of the Invention

The present invention relates to surgical implants suitable for use in affixing bone, bones, or bone pieces and, more particularly, but not by way of limitation, to a method and apparatus for a shape memory implant that affixes bone, bones, or bone pieces in order to fuse or distract the bone, bones, or bone pieces and promote a healing thereof.

2. Description of the Related Art

Shape memory materials such as nitinol (nickel-titanium) due to their superelastic or temperature dependent properties currently are employed in the manufacture of surgical implants designed to affix bone, bones, or bone pieces. A surgical implant manufactured from a shape memory material with superelastic or temperature dependent properties typically includes a natural shape. Nevertheless, the surgical implant may be deformed from its natural shape to an insertion shape whereby the surgical implant stores energy deliverable to a bone, bones, or bone pieces. The surgical implant when deformed to its insertion shape typically loads on a mechanical constraint that prevents transition of the surgical implant from its insertion shape to its natural shape. The surgical implant once loaded on a mechanical constraint is deliverable to a bone, bones, or bone pieces. After the surgical implant is delivered and released from the mechanical constraint, the surgical implant attempts to transition from its insertion shape to its natural shape such that the surgical implant exerts either a compressive or distractive force to the bone, bones, or bone pieces.

Surgical implants manufactured from a shape memory material with superelastic or temperature dependent properties include surgical staples. A surgical staple typically includes a bridge with one or more transition sections having legs extending therefrom. The surgical staple includes a natural shape where the one or more transition sections maintain the legs in a natural position, which normally is converging for fusion or substantially parallel for distraction. The surgical staple, however, deforms from its natural shape to an insertion shape where the one or more transition sections move the legs to an insertion position, which normally is substantially parallel for fusion or converging for distraction for distraction. The surgical staple once deformed to its insertion shape typically loads on a mechanical constraint prior to the delivery of the surgical staple into a bone, bones, or bone pieces. After the surgical staple is delivered and released from the mechanical constraint, the surgical staple, due to its superelastic or temperature dependent properties, attempts to transition from its insertion shape to its natural shape such that the surgical staple exerts either a compressive or distractive force, to the bone, bones, or bone pieces.

While surgical staples in most instances operate adequately in the healing of bone, bones, or bone pieces, the quality of the bone, bones, or bone pieces into which a surgical staple is implanted impacts the ability of the surgical staple to fuse the bone, bones, or bone pieces. Bone, bones, or bone pieces in patients exhibiting a typical bone quality provide structural integrity sufficient to arrest movement of the legs for a surgical staple during its attempted transition from its insertion shape to its natural shape such that the surgical staple imparts a force adequate to fuse or distract the bone, bones, or bone pieces. Conversely, bone, bones, or bone pieces in patients exhibiting a poorer bone quality, due to osteoporosis, trauma, or the like, lack structural integrity sufficient to arrest movement of the legs for a surgical staple during its attempted transition from its insertion shape to its natural shape such that the surgical staple over-transitions to a leg position incapable of imparting a force adequate to properly fuse or distract the bone, bones, or bone pieces. As a consequence, the bone, bones, or bone pieces experience a loss of fixation that may result in an improper fusion or distraction of the bone, bones, or bone pieces.

Accordingly, a method and apparatus for a shape memory implant that allows for bone, bones, or bone pieces to be structurally augmented during implantation of the shape memory implant will overcome the disadvantages currently experienced with shape memory implants due to the quality of bone, bones, or bone pieces and, in particular, bone, bones, or bone pieces of poorer quality.

SUMMARY OF THE INVENTION

In accordance with the present invention, an apparatus for fixating bone includes an orthopedic implant. The orthopedic implant, which may be manufactured from a shape memory material, is moveable between a natural shape and an insertion shape. The orthopedic implant defines at least a first cannulation therethrough adapted to deliver a bone augmentation material to the bone. The orthopedic implant further may define a second cannulation therethrough adapted to deliver a bone augmentation material to the bone. The orthopedic implant implants into the bone in its insertion shape. After implantation of the orthopedic implant, a bone augmentation material delivered into the bone via the first cannulation augments the bone. The second cannulation allows delivery of additional bone augmentation material into the bone that further augments the bone. The orthopedic implant once implanted attempts to transition from its insertion shape to its natural shape such that the orthopedic implant fixates the bone.

The orthopedic implant in a first embodiment includes a bridge with a first end and a second end, a first leg extending from the bridge adjacent its first end, and a second leg extending from the bridge adjacent its second end. The bridge and the first leg define the first cannulation, whereas the bridge and the second leg define the second cannulation. The first and second legs reside in a natural position when the orthopedic implant resides in its natural shape. Conversely, the first and second legs reside in an insertion position when the orthopedic implant resides in its insertion shape. The first and second legs implant into the bone in their insertion position with the bridge traversing a fixation zone of the bone. The first and second legs after implantation of the orthopedic implant attempt to move from their insertion position to their natural position when the orthopedic implant attempts to transition from its insertion shape to its natural shape. The bridge includes at least one transition section moveable between a natural form when the orthopedic implant resides in its natural shape that locates the first and second legs in their natural position and an insertion form when the orthopedic implant resides in its insertion shape that locates the first and second legs in their insertion shape.

The first cannulation includes an inlet in the bridge and at least one outlet in the first leg. The first cannulation traverses the bridge and the first leg to deliver a bone augmentation material into the bone around the first leg. Likewise, the second cannulation includes an inlet in the bridge and at least one outlet in the second leg. The second cannulation traverses the bridge and the second leg to deliver a bone augmentation material into the bone around the second leg.

The orthopedic implant in a second embodiment includes a third leg extending from the bridge between the first leg and a central axis of the bridge. The bridge and the third leg define a third cannulation adapted to deliver a bone augmentation material to the bone. The third cannulation includes an inlet in the bridge and at least one outlet in the third leg. The third cannulation traverses the bridge and the third leg to deliver a bone augmentation material into the bone around the third leg. The orthopedic implant in the second embodiment includes a fourth leg extending from the bridge between the second leg and a central axis of the bridge. The bridge and the fourth leg define a fourth cannulation adapted to deliver a bone augmentation material to the bone. The fourth cannulation includes an inlet in the bridge and at least one outlet in the fourth leg. The fourth cannulation traverses the bridge and the fourth leg to deliver a bone augmentation material into the bone around the fourth leg.

The orthopedic implant in a third embodiment includes a first aperture in the bridge adjacent its first end and a second aperture in the bridge adjacent its second end. The first aperture receives therethrough a fixation device that engages the bone. Similarly, the second aperture receives therethrough a fixation device that engages the bone. In the third embodiment, the first leg extends from the bridge between the first aperture and a central axis of the bridge, whereas the second leg extends from the bridge between the second aperture and the central axis of the bridge.

The orthopedic implant in a fourth embodiment includes a third leg adjacent the first leg that extends from the bridge at its first end. The bridge and the third leg define a third cannulation adapted to deliver a bone augmentation material to the bone. The third cannulation includes an inlet in the bridge and at least one outlet in the third leg. The third cannulation traverses the bridge and the third leg to deliver a bone augmentation material into the bone around the third leg.

The orthopedic implant in a fifth embodiment includes, in addition to a third leg similar to the third leg of the fourth embodiment, a fourth leg adjacent the second leg that extends from the bridge at its second end. The bridge and the fourth leg define a fourth cannulation adapted to deliver a bone augmentation material to the bone. The fourth cannulation includes an inlet in the bridge and at least one outlet in the fourth leg. The fourth cannulation traverses the bridge and the fourth leg to deliver a bone augmentation material into the bone around the fourth leg.

In a method for the orthopedic implant of the present invention, the orthopedic implant transitions from its natural shape to its insertion shape followed by a mechanical constraint engaging the orthopedic implant in its insertion shape. The orthopedic implant implants into a bone while the orthopedic implant resides in its insertion shape. The first cannulation defined by the orthopedic implant delivers a bone augmentation material into the bone whereby the bone augmentation material augments the bone. The second cannulation defined by the orthopedic implant also may deliver a bone augmentation material into the bone via a whereby the bone augmentation material augments the bone. The mechanical constraint releases the orthopedic implant such that an attempted transition of the orthopedic implant from its insertion shape to its natural shape fixates the bone.

In an alternative method for the orthopedic implant of the present invention, the orthopedic implant transitions from its natural shape to its insertion shape followed by a mechanical constraint engaging the orthopedic implant in its insertion shape. The orthopedic implant implants into a bone while the orthopedic implant resides in its insertion shape. The mechanical constraint releases the orthopedic implant such that an attempted transition of the orthopedic implant from its insertion shape to its natural shape fixates the bone. The first cannulation defined by the orthopedic implant delivers a bone augmentation material into the bone whereby the bone augmentation material augments the bone. The second cannulation defined by the orthopedic implant also may deliver a bone augmentation material into the bone via a whereby the bone augmentation material augments the bone.

More particularly with respect to the methods for the orthopedic implant, implanting the orthopedic implant includes implanting the first and second legs into the bone in their insertion position with the bridge traversing a fixation zone of the bone. Releasing the orthopedic implant from the mechanical constraint includes an attempted movement of the first and second legs from their insertion position to their natural position when the orthopedic implant attempts transition from its insertion shape to its natural shape. Delivering a bone augmentation material into the bone includes introducing a bone augmentation material into the first cannulation via an inlet thereof in the bridge, flowing the bone augmentation material through the bridge and the first leg via the first cannulation, and conveying the bone augmentation material into the bone around the first leg via at least one outlet in the first leg. Delivering a bone augmentation material into the bone further includes introducing a bone augmentation material into the second cannulation via an inlet thereof in the bridge, flowing the bone augmentation material through the bridge and the second leg via the second cannulation, and conveying the bone augmentation material into the bone around the second leg via at least one outlet in the second leg.

It is therefore an object of the present invention to provide an orthopedic implant comprising a shape memory material such the orthopedic implant transitions between a natural shape and an insertion shape.

It is another object of the present invention to provide the orthopedic implant with at least one cannulation therethrough adapted to deliver a bone augmentation material to the bone whereby the delivered bone augmentation material augments the bone.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

DETAILED DESCRIPTION OF THE PREFERRED EMBODIMENTS

Figure 1:
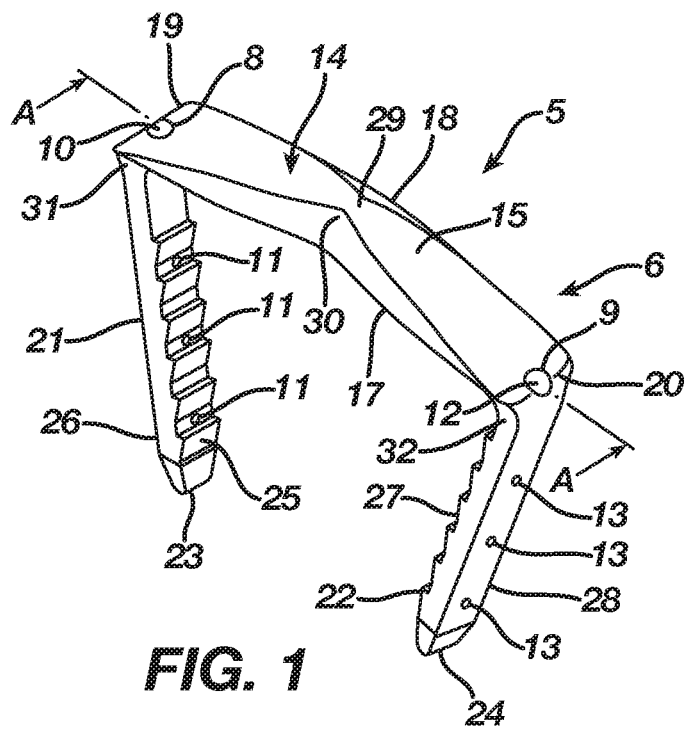
FIG. 1 is an isometric view illustrating a shape memory implant according to a first embodiment in a natural shape.
Figure 2:
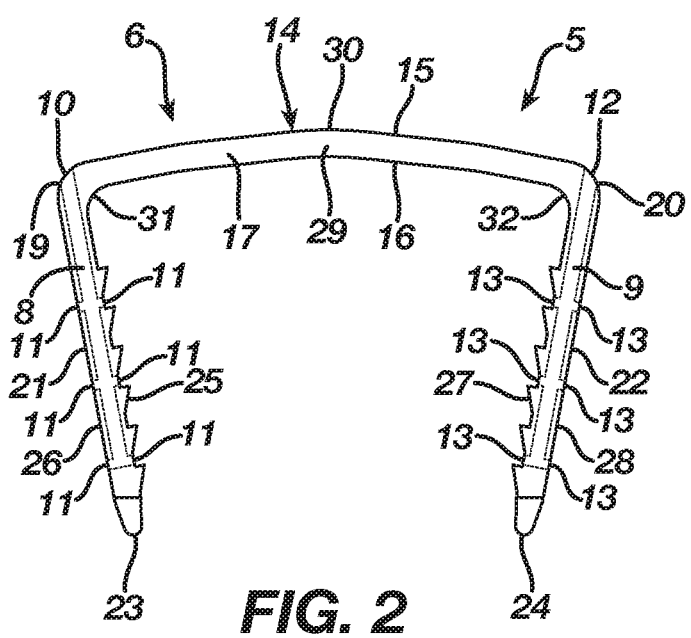
FIG. 2 is a side view thereof.
Figure 3:
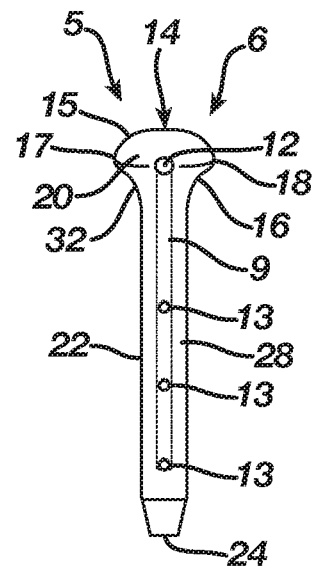
FIG. 3 is an end view thereof.
Figure 4:
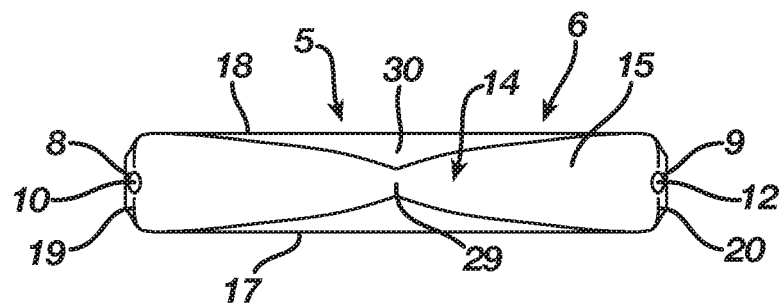
FIG. 4 is a top view thereof.
Figure 5:
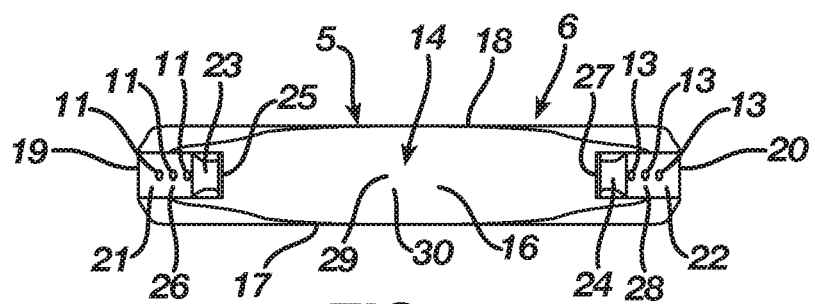
FIG. 5 is a bottom view thereof.
Figure 6:
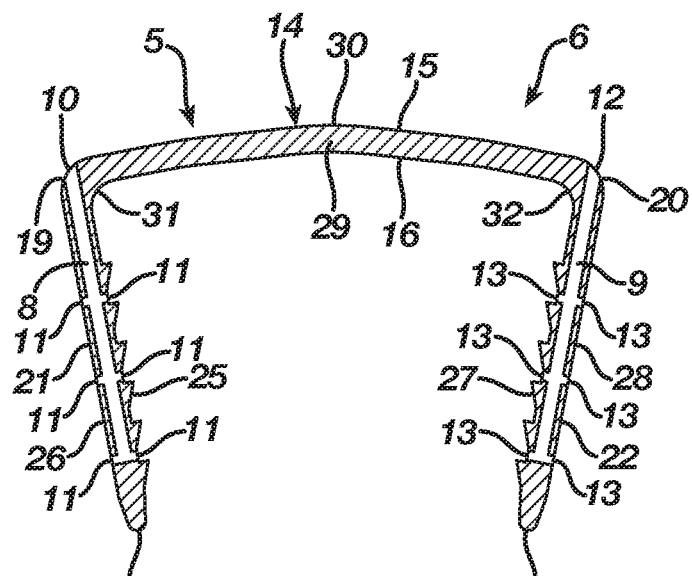
FIG. 6 is a cross-sectional view taken along lines A-A of FIG. 1 illustrating the shape memory implant according to the first embodiment in its natural shape.
Figure 7:
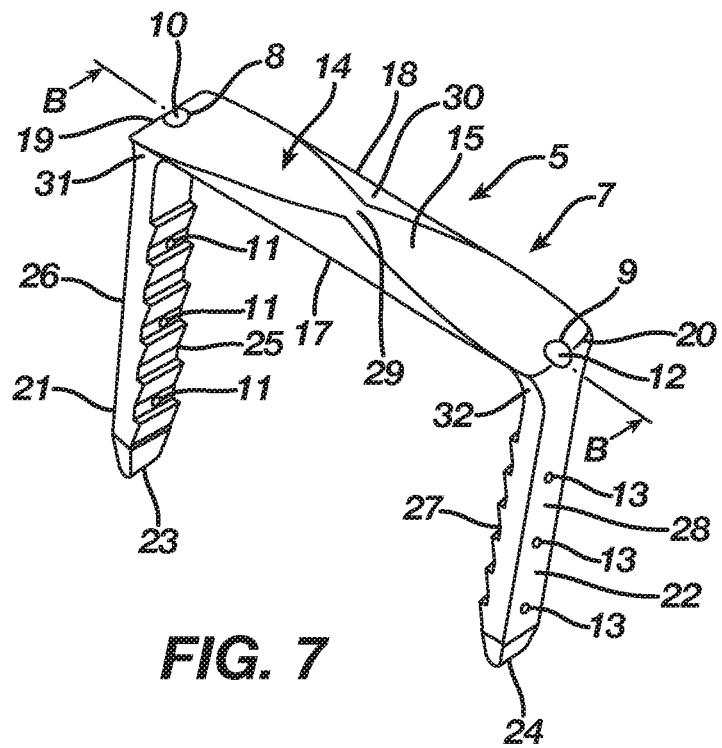
FIG. 7 is an isometric view illustrating the shape memory implant according to the first embodiment in an insertion shape.
Figure 8:
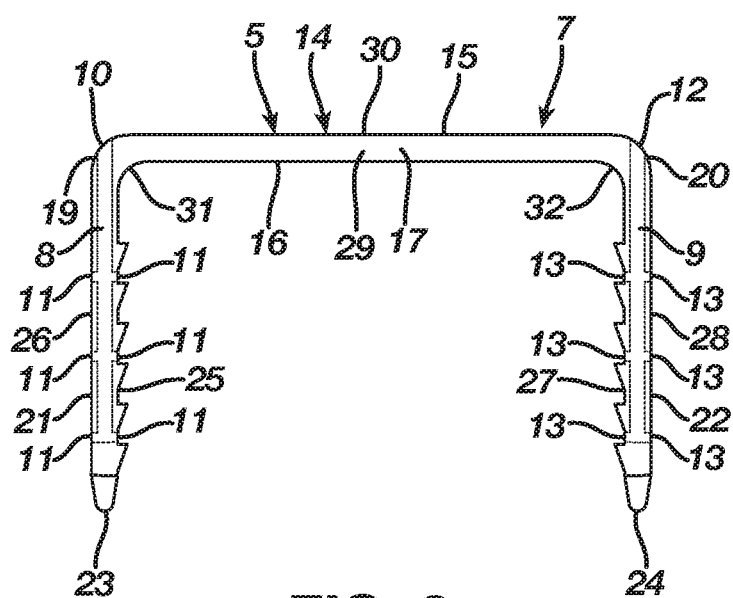
FIG. 8 is a side view thereof.
Figure 9:
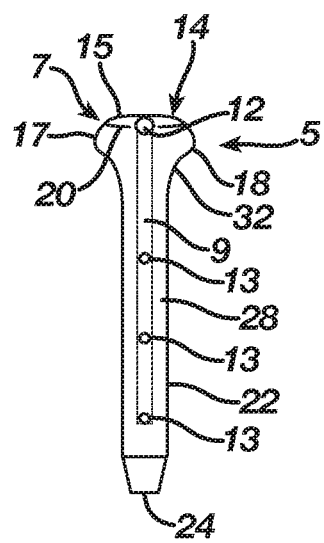
FIG. 9 is an end view thereof.
Figure 10:
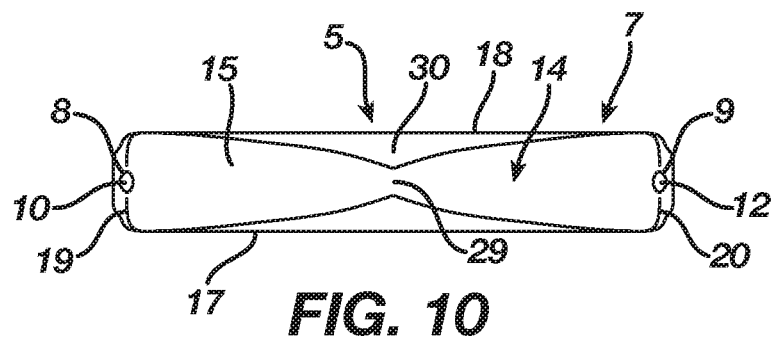
FIG. 10 is a top view thereof.
Figure 11:
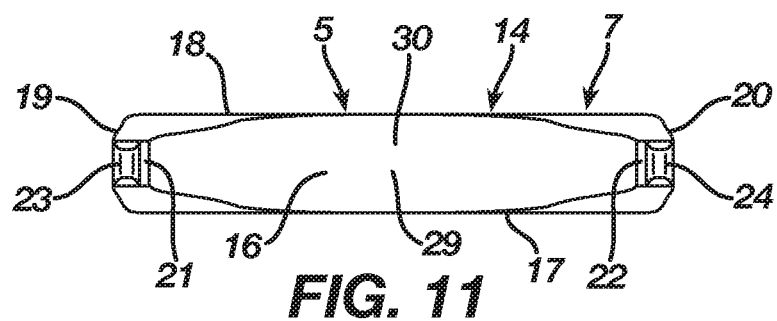
FIG. 11 is a bottom view thereof.
Figure 12:
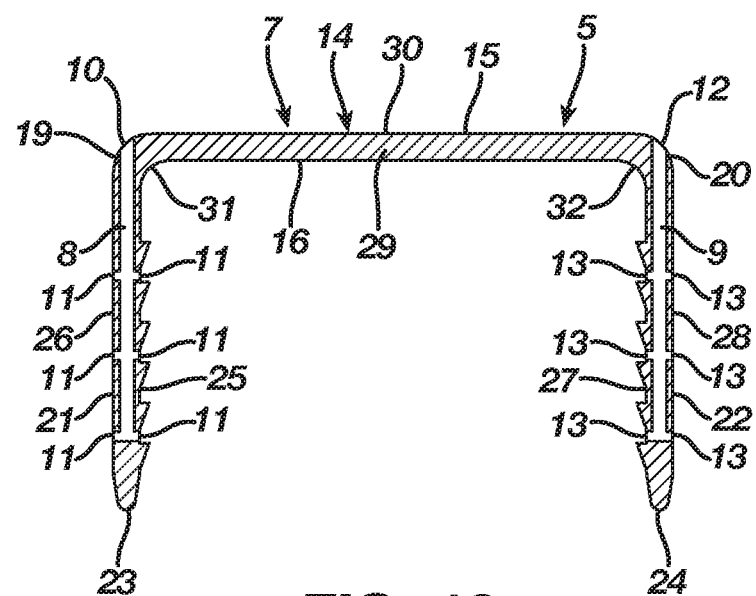
FIG. 12 is a cross-sectional view taken along lines B-B of FIG. 7 illustrating the shape memory implant according to the first embodiment in its insertion shape.

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

FIGS. 1-6 illustrate an orthopedic implant 5 according to a first embodiment in a natural shape 6, whereas FIGS. 7-12 illustrate the orthopedic implant 5 in an insertion shape 7. The implant 5 in the first embodiment may be manufactured from a shape memory material with superelastic or temperature dependent properties (e.g., Nitinol) such that the implant 5 transitions between its natural shape 6 and its insertion shape 7. The implant 5 when deformed from its natural shape 6 to its insertion shape 7 stores energy deliverable to bone, bones, or bone pieces. In accordance with its manufacture from shape memory material, the implant 5 begins in its natural shape 6, is transitionable to its insertion shape 7, and, once implanted in bone, bones, or bone pieces, attempts to transition from its insertion shape 7 to its natural shape 6 whereby the implant 5 delivers the energy stored therein to the bone, bones, or bone pieces in order to affix the bone, bones, or bone pieces and promote a healing thereof. In the first embodiment, attempted transition of the implant 5 from its insertion shape 7 to its natural shape 6 continuously compresses the bone, bones, or bone pieces to promote fusion thereof. Nevertheless, one of ordinary skill in the art will recognize that the attempted transition of the implant 5 from its insertion shape 7 to its natural shape 6 may distract the bone, bones, or bone pieces to hold the bone, bones, or bone pieces in an arrangement that promotes a healing thereof. In a distraction configuration, FIGS. 7-12 would illustrate an orthopedic implant 5 in a natural shape, whereas FIGS. 1-6 would illustrate the orthopedic implant 5 in an insertion shape.

When the implant 5 inserts into bone, bones, or bone pieces of a patient having a typical bone quality, the bone, bones, or bone pieces exhibit a structural integrity sufficient to arrest movement of the implant 5 during its attempted transition from its insertion shape 7 to its natural shape 6 such that the implant 5 imparts a force adequate to fuse or distract the bone, bones, or bone pieces. Conversely, when the implant 5 inserts into bone, bones, or bone pieces of a patient with a poorer bone quality, due to osteoporosis, trauma, or the like, the bone, bones, or bone pieces lack structural integrity sufficient to arrest movement of the implant 5 during its attempted transition from its insertion shape 7 to its natural shape 6 such that the implant 5 over-transitions resulting in the implant 5 failing to impart a force adequate to properly fuse or distract the bone, bones, or bone pieces. As a consequence, the bone, bones, or bone pieces of poorer quality may experience a loss of fixation and subsequent improper fusion or distraction thereof.

In order to enhance implantation of the implant 5 into bone, bones, or bone pieces including an ability of the implant 5 to overcome any implantation issues associated with bone, bones, or bone pieces of poorer quality, the implant 5 includes at least one cannulation 8 and, in the first embodiment, a second cannulation 9. The cannulation 8 includes an inlet 10 and at least one outlet 11 and, in the first embodiment, multiple outlets 11. Likewise, the cannulation 9 includes an inlet 12 and at least one outlet 13 and, in the first embodiment, multiple outlets 13. During the insertion of the implant 5 into bone, bones, or bone pieces, the cannulation 8 permits introduction of a bone augmentation material, such as bone cement, into the bone, bones, or bone pieces whereby the bone augmentation material enters and fills the bone, bones, or bone pieces to augment the structural integrity thereof. In particular, the bone augmentation material enters the cannulation 8 via its inlet 10, traverses the cannulation 8, and then exits the cannulation 8 via its one or more outlets 11 into the bone, bones, or bone pieces. The bone augmentation material fills the bone, bones, or bone pieces, and, once its sets or cures, the bone augmentation material enhances the structural integrity of the bone, bones, or bone pieces whereby the bone, bones, or bone pieces receive energy imparted thereto from the implant 5 without experiencing a structural failure that causes a loss of fixation and subsequent improper fusion or distraction thereof. The bone augmentation material accordingly augments the bone, bones, or bone pieces resulting in the bone, bones, or bone pieces arresting movement of the implant 5 during its attempted transition from its insertion shape 7 to its natural shape 6 such that the implant 5 imparts a force sufficient to fuse or distract the bone, bones, or bone pieces. Similar to the cannulation 8, the cannulation 9 permits introduction of a bone augmentation material, such as bone cement, into the bone, bones, or bone pieces during the insertion of the implant 5 into bone, bones, or bone pieces. The bone augmentation material enters the cannulation 9 via its inlet 12, traverses the cannulation 9, and then exits the cannulation 9 via its one or more outlets 13 into the bone, bones, or bone pieces. The cannulation 9 accordingly delivers the bone augmentation material into the bone, bones, or bone pieces at a location different from that of the cannulation 8 whereby the bone augmentation material enters and fills the bone, bones, or bone pieces to further augment the structural integrity thereof.

In the first embodiment, the implant 5 includes a bridge 14 with a three-dimensional form having a length, width, and height, and, in particular, the bridge 14 includes a central axis 30 and an upper surface 15 and a lower surface 16 with first and second sides 17 and 18 and first and second ends 19 and 20 therebetween. The bridge 14 is tapered to present a non-uniform cross-sectional thickness between the upper and lower surfaces 15 and 16 in order to provide strength to the bridge 14 while lowering its profile. Although the bridge 14 is tapered in the first embodiment, one of ordinary skill in the art will recognize that the bridge 14 may include a uniform cross-sectional thickness between the upper and lower surfaces 15 and 16.

The implant 5 in the first embodiment includes an anchoring member in the form of a leg 21 extending from the lower surface 16 of the bridge 14 at its end 19 and an anchoring member in the form of a leg 22 extending from the lower surface 16 of the bridge 14 at its end 20. In the first embodiment, the leg 21 is formed integrally with the bridge 14 at its end 19, while the leg 22 is formed integrally with the bridge 14 at its end 20. Each leg 21 and 22, which has a respective tip 23 and 24, may include barbs thereon that improve the pull-out resistance of the implant 5. The implant 5 includes anchoring members in the form of legs 21 and 22 in order to facilitate a securing of the implant 5 with bone, bones, or bone pieces whereby the bridge 14 between the legs 21 and 22 traverses a fixation zone of the bone, bones, or bone pieces such that the implant 5, after its insertion and attempted transition from the insertion shape 7 to the natural shape 6, delivers energy to the bone, bones, or bone pieces at the fixation zone.

The cannulation 8 in the first embodiment of the implant 5 originates in the bridge 14 with its inlet 10 in the bridge 14 at the leg 21 adjacent the end 19 of the bridge 14. The cannulation 8 traverses the bridge 14 and then the leg 21 until the cannulation 8 exits the leg 21 in at least one outlet 11 located at any point along the leg 21 including at the tip 23 such that the at least one outlet 11 delivers a bone augmentation material around the leg 21. While the cannulation 8 requires only a single outlet 11, the cannulation 8 in the first embodiment includes multiple outlets 11 located along an interior side 25 and an exterior side 26 of the leg 21 such that the multiple outlets 11 facilitate delivery of a bone augmentation material around the leg 21 and its tip 23. Nevertheless, one of ordinary skill in the art will recognize that the multiple outlets 11 may be located at any point along the leg 21 including at the tip 23. The cannulation 8 includes its inlet 10 located in the bridge 14 at the leg 21 adjacent the end 19 of the bridge 14 to allow access thereto from the bridge 14 on the basis the bridge 14 resides atop bone, bones, or bone pieces after implantation of the implant 5. The cannulation 8 traverses the bridge 14 and the leg 21 and exits the leg 21 at the outlets 11 located in the leg 21 because, after implantation of the implant 5, the leg 21 resides in bone, bones, or bone pieces, thereby facilitating delivery of bone augmentation material into the bone, bones, or bone pieces via the cannulation 8.

The cannulation 9 in the first embodiment of the implant 5 originates in the bridge 14 with its inlet 12 in the bridge 14 at the leg 22 adjacent the end 20 of the bridge 14. The cannulation 9 traverses the bridge 14 and then the leg 22 until the cannulation 9 exits the leg 22 in at least one outlet 13 located at any point along the leg 22 including at the tip 24 such that the at least one outlet 13 delivers a bone augmentation material around the leg 22. While the cannulation 9 requires only a single outlet 13, the cannulation 9 in the first embodiment includes multiple outlets 13 located along an interior side 27 and an exterior side 28 of the leg 22 such that the multiple outlets 13 facilitate delivery of a bone augmentation material around the leg 22 and its tip 24. Nevertheless, one of ordinary skill in the art will recognize that the multiple outlets 13 may be located at any point along the leg 22 including at the tip 24. The cannulation 9 includes its inlet 12 located in the bridge 14 at the leg 22 adjacent the end 20 of the bridge 14 to allow access thereto from the bridge 14 on the basis the bridge 14 resides atop bone, bones, or bone pieces after implantation of the implant 5. The cannulation 9 traverses the bridge 14 and the leg 22 and exits the leg 22 at the outlets 13 located in the leg 22 because, after implantation of the implant 5, the leg 22 resides in bone, bones, or bone pieces, thereby facilitating delivery of bone augmentation material into the bone, bones, or bone pieces via the cannulation 9.

In the first embodiment, the bridge 14 includes a transition section 29 disposed at the central axis 30 thereof. The regular inherent shape of the implant 5 according to the first embodiment, as illustrated in FIGS. 1-6, is its natural shape 6 where the transition section 29 locates the bridge 14 in a natural form consisting of a closed or angular profile whereby the first and second ends 19 and 20 reside at a first distance and the legs 21 and 22 reside in a natural position whereby the legs 21 and 22 are convergent and spaced apart at a first distance. Nevertheless, as illustrated in FIGS. 6-12, the implant 5 is deformable under the action of superelasticity or temperature dependent shape memory to its insertion shape 7 where the transition section 29 deforms to store energy while also moving the bridge 14 from its natural form to an insertion form which, in the first embodiment, is an open or substantially linear profile whereby the first and second ends 19 and 20 reside at a second distance that is greater than the first distance and the legs 21 and 22 reside in an insertion position whereby the legs 21 and 22 are substantially parallel and spaced apart at a second distance that is greater than the first distance. Since the insertion shape 7 is not the regular inherent shape of the implant 5, the transition section 29 typically is mechanically constrained or chilled until it reaches its martensite phase whereby the transition section 29 once deformed maintains the bridge 14 in its insertion form. After implantation into bone, bones, or bone pieces and a release of a mechanical constraint or a heating of the implant 5 to its austenite phase, the implant 5 delivers the energy stored in the transition section 29 such that the bridge 14 attempts to transition from its insertion form to its natural form, resulting in the legs 21 and 22 attempting to move from their insertion position to their natural position whereby the implant 5 affixes the bone, bones, or bone pieces through an application of a compressive force thereto.

While the transition section 29 of the bridge 14 has been described as moving to create compression, one of ordinary skill in the art will recognize that movement of the transition section 29 and attempted transition of the bridge 14 from its insertion form to its natural form may distract bone, bones, or bone pieces to hold the bone, bones, or bone pieces in an arrangement that promotes a healing thereof. In a distraction configuration, FIGS. 7-12 would illustrate an orthopedic implant 5 in a natural shape, whereas FIGS. 1-6 would illustrate the orthopedic implant 5 in an insertion shape. The transition section 29 for distraction locates the bridge 14 in a natural form consisting of an open or substantially linear profile whereby the first and second ends 19 and 20 reside at a first distance and the legs 21 and 22 reside in a natural position whereby the legs 21 and 22 are substantially parallel and spaced apart at a first distance. Nevertheless, the transition section 29 deforms to store energy while also moving the bridge 14 from its natural form to an insertion form which is a closed or angular profile whereby the first and second ends 19 and 20 reside at a second distance that is less than the first distance and the legs 21 and 22 reside in an insertion position whereby the legs 21 and 22 are convergent and spaced apart at a second distance that is less than the first distance. Upon implantation into bone, bones, or bone pieces and a release of a mechanical constraint or a heating of the implant 5 to its austenite phase, the implant 5 delivers the energy stored in the transition section 29 such that the bridge 14 attempts to transition from its insertion form to its natural form, resulting in the legs 21 and 22 attempting to move from their insertion position to their natural position whereby the implant 5 affixes the bone, bones, or bone pieces through an application of a distractive force thereto.

Figure 13:
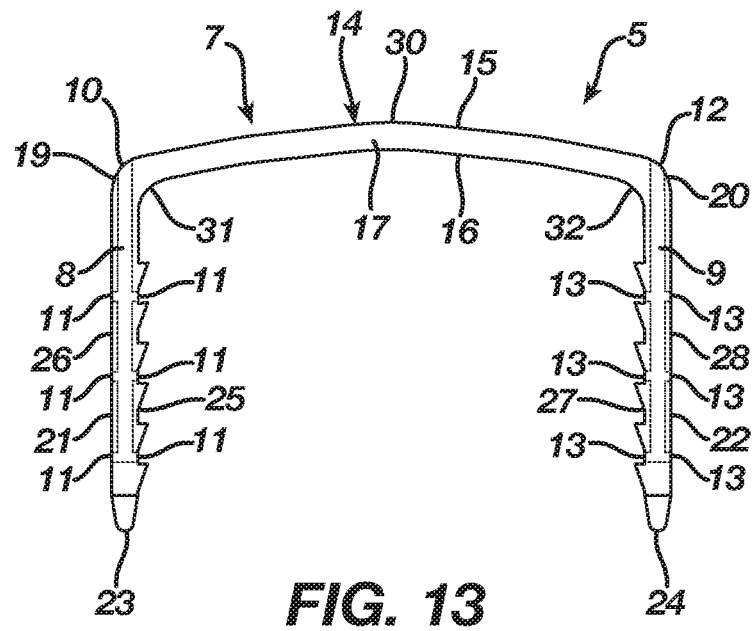
FIG. 13 is a side view of a shape memory implant according to an alternative of the first embodiment in an insertion shape.

Alternatively, the bridge 14 in the first embodiment may include transition sections 31 and 32 located respectively where the legs 21 and 22 extend from the bridge 14. The regular inherent shape of the implant 5, as illustrated in FIGS. 1-6, is its natural shape 6 where the transition sections 31 and 32 locate the bridge 14 in a natural form that places the legs 21 and 22 in a natural position whereby the legs 21 and 22 are convergent and spaced apart at a first distance. Nevertheless, as illustrated in FIG. 13, the implant 5 is deformable under the action of superelasticity or temperature dependent shape memory to an insertion shape 7 where the transition sections 31 and 32 deform to store energy while also moving the bridge 14 from its natural form to an insertion form that places the legs 21 and 22 in an insertion position whereby the legs 21 and 22 are substantially parallel and spaced apart at a second distance that is greater than the first distance. Since the insertion shape 7 is not the regular inherent shape of the implant 5, the transition sections 31 and 32 typically are mechanically constrained or chilled until they reach their martensite phase whereby the transition sections 31 and 32 once deformed maintain the bridge 14 in its insertion form. After implantation into bone, bones, or bone pieces and a release of a mechanical constraint or a heating of the implant 5 to its austenite phase, the implant 5 delivers the energy stored in the transition sections 31 and 32 such that the bridge 14 attempts to transition from its insertion form to its natural form, resulting in the legs 21 and 22 attempting to move from their insertion position to their natural position whereby the implant 5 affixes the bone, bones, or bone pieces through an application of a compressive force thereto.

While the transition sections 31 and 32 of the bridge 14 have been described as moving to create compression, one of ordinary skill in the art will recognize that movement of the transition sections 31 and 32 and attempted transition of the bridge 14 from its insertion form to its natural form may distract bone, bones, or bone pieces to hold the bone, bones, or bone pieces in an arrangement that promotes a healing thereof. In a distraction configuration, FIG. 13 would illustrate an orthopedic implant 5 in a natural shape, whereas FIGS. 1-6 would illustrate the orthopedic implant 5 in an insertion shape. The transition sections 31 and 32 for distraction locate the bridge 14 in a natural form that places the legs 21 and 22 in a natural position whereby the legs 21 and 22 are substantially parallel and spaced apart at a first distance. Nevertheless, the transition sections 31 and 32 deform to store energy while also moving the bridge 14 from its natural form to an insertion form that places the legs 21 and 22 in an insertion position whereby the legs 21 and 22 are convergent and spaced apart at a second distance that is less than the first distance. Upon implantation into bone, bones, or bone pieces and a release of a mechanical constraint or a heating of the implant 5 to its austenite phase, the implant 5 delivers the energy stored in the transition sections 31 and 32 such that the bridge 14 attempts to transition from its insertion form to its natural form, resulting in the legs 21 and 22 attempting to move from their insertion position to their natural position whereby the implant 5 affixes the bone, bones, or bone pieces through an application of a distractive force thereto.

Figure 14:
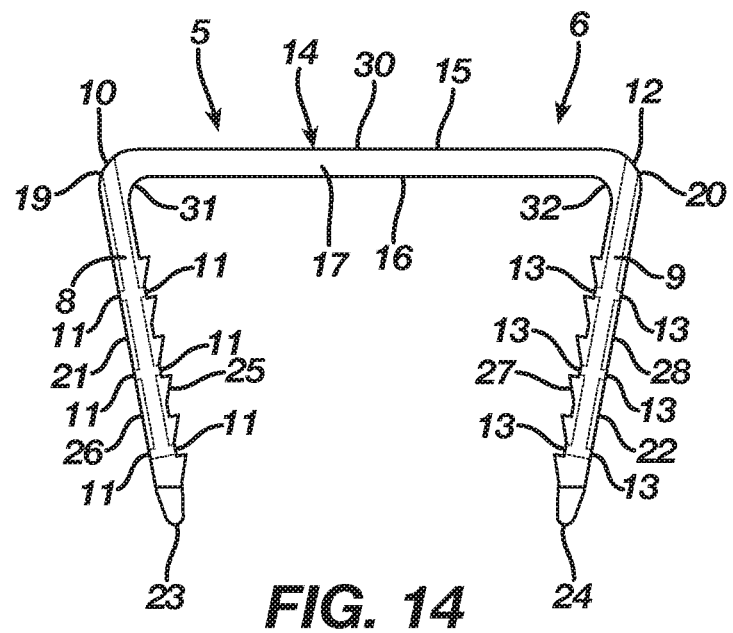
FIG. 14 is a side view of a shape memory implant according to an alternative of the first embodiment in a natural shape.
Figure 15:
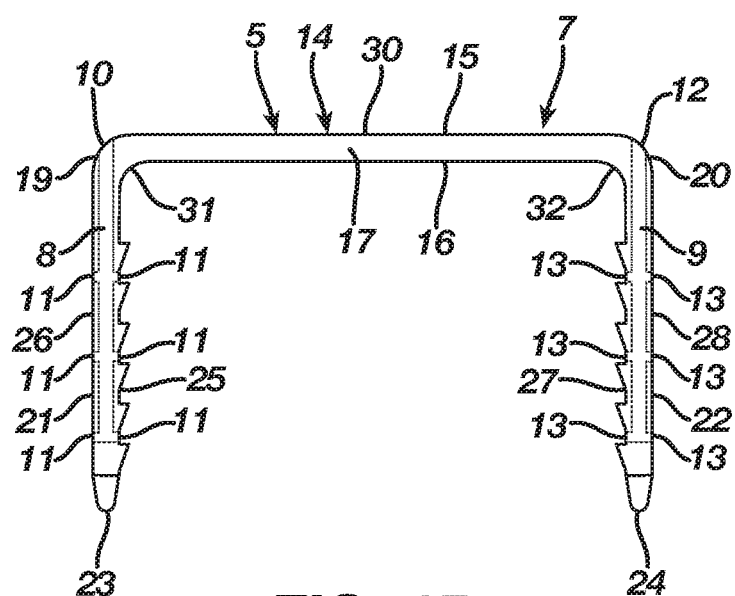
FIG. 15 is a side view of a shape memory implant according to an alternative of the first embodiment in an insertion shape.
Figure 16:
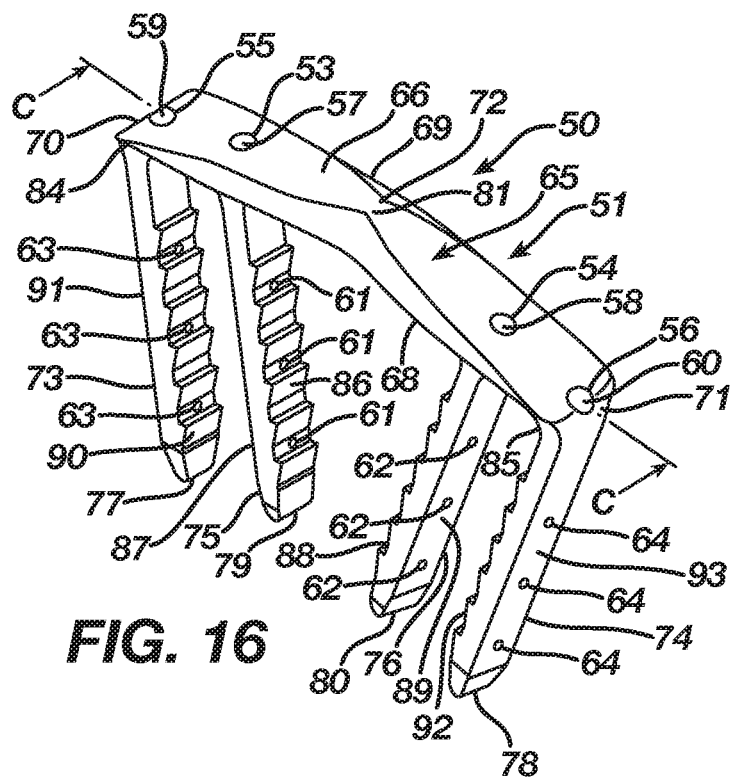
FIG. 16 is an isometric view illustrating a shape memory implant according to a second embodiment in a natural shape.
Figure 17:
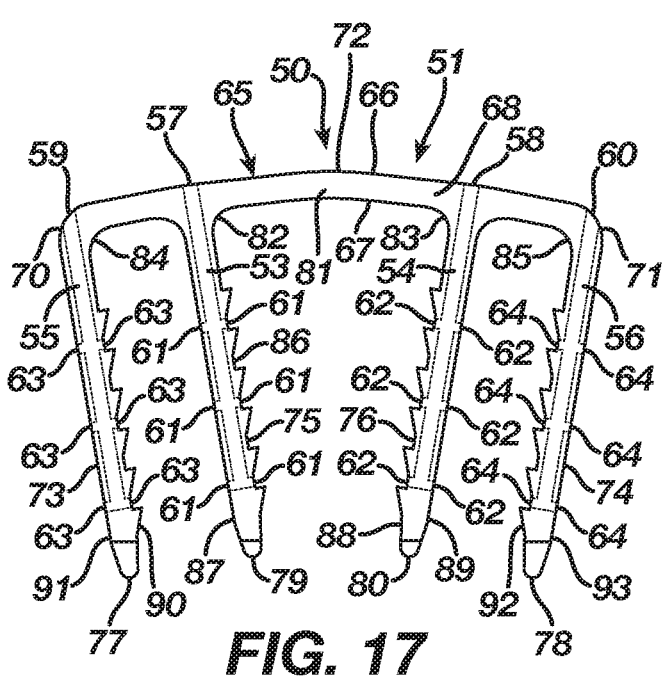
FIG. 17 is a side view thereof.
Figure 18:
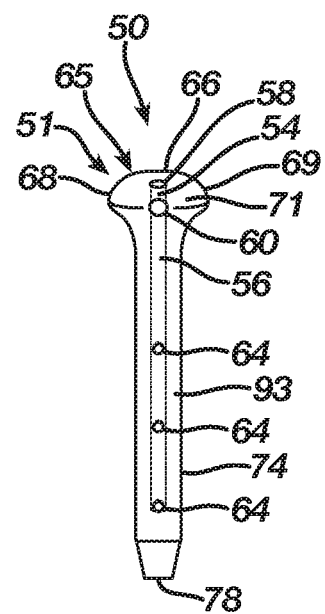
FIG. 18 is an end view thereof.
Figure 19:
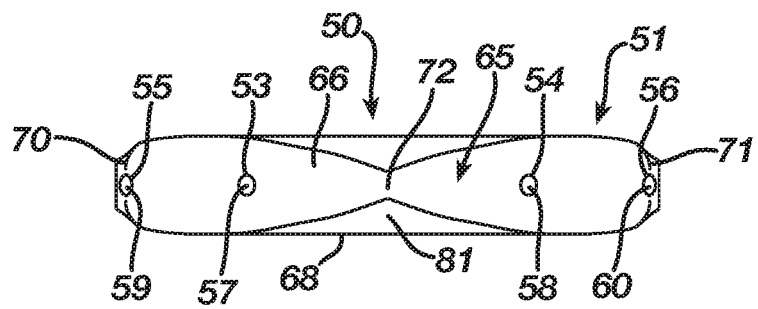
FIG. 19 is a top view thereof.
Figure 20:
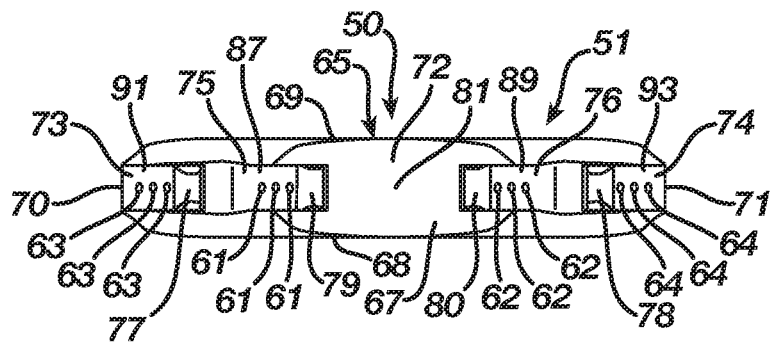
FIG. 20 is a bottom view thereof.
Figure 21:
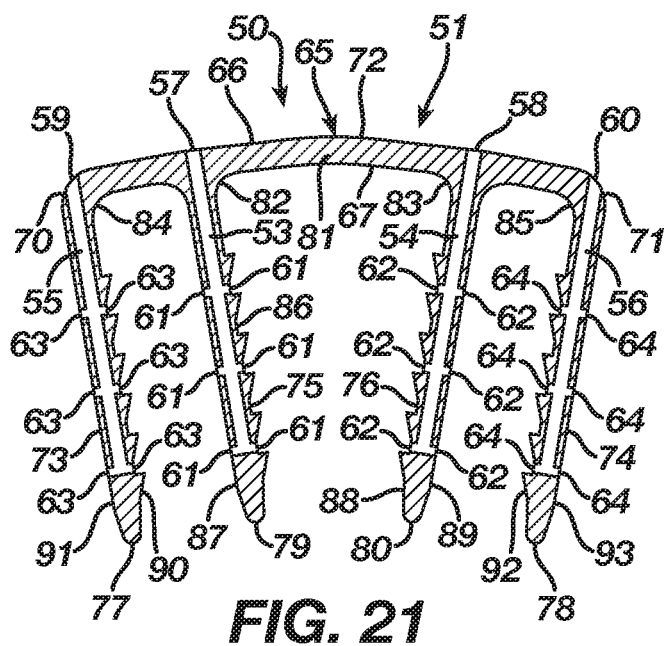
FIG. 21 is a cross-sectional view taken along lines C-C of FIG. 16 illustrating the shape memory implant according to the second embodiment in its natural shape.
Figure 22:
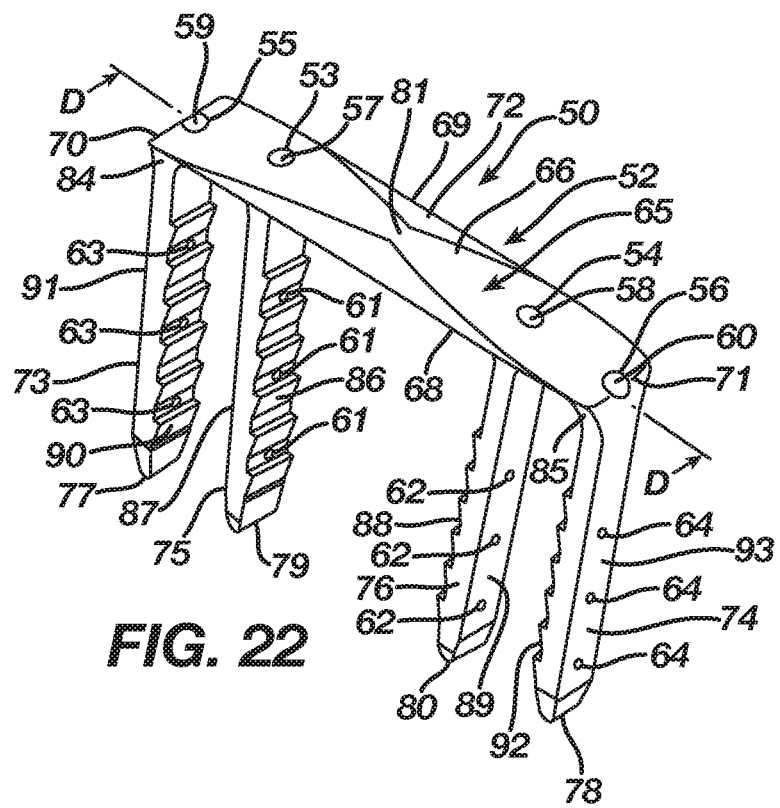
FIG. 22 is an isometric view illustrating the shape memory implant according to the second embodiment in an insertion shape.
Figure 23:
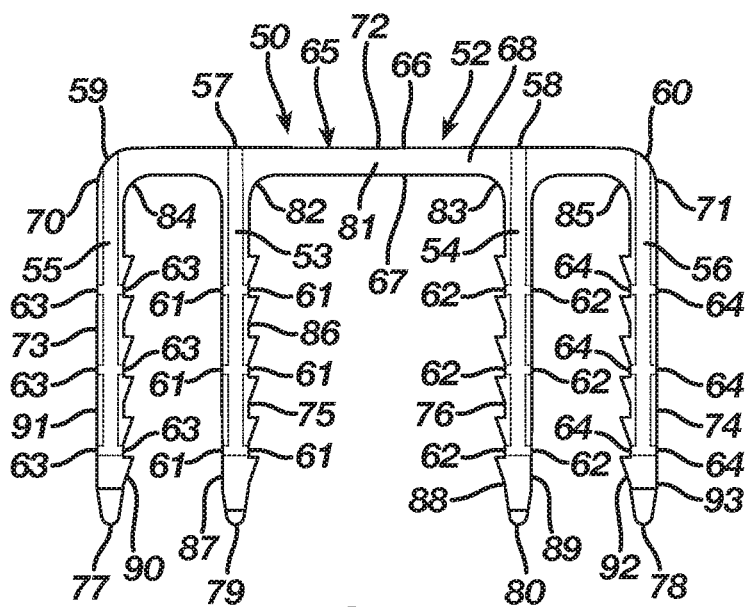
FIG. 23 is a side view thereof.
Figure 24:
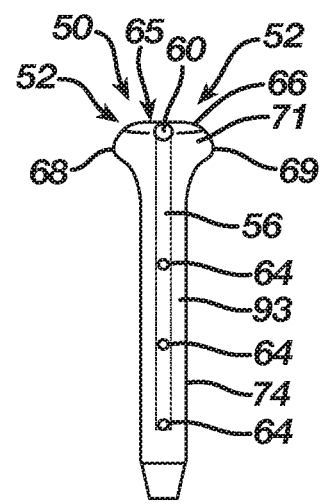
FIG. 24 is an end view thereof.
Figure 25:
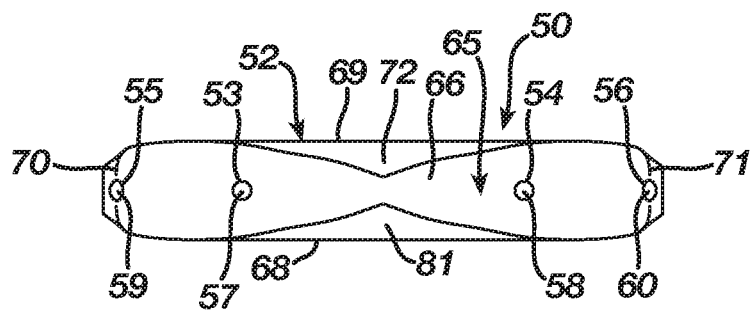
FIG. 25 is a top view thereof.
Figure 26:
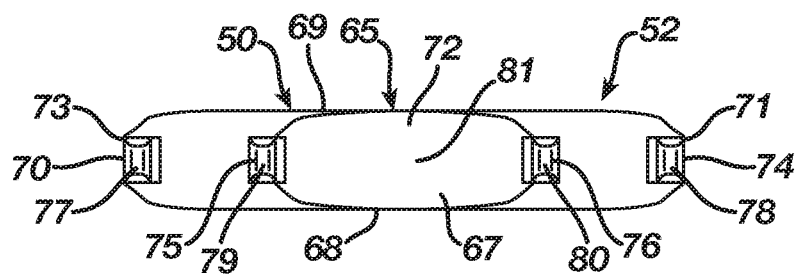
FIG. 26 is a bottom view thereof.
Figure 27:
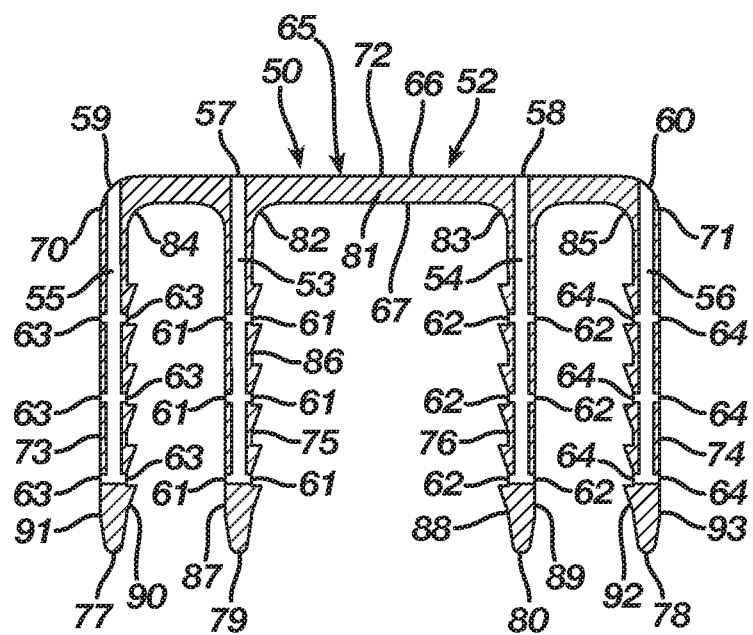
FIG. 27 is a cross-sectional view taken along lines D-D of FIG. 22 illustrating the shape memory implant according to the second embodiment in its insertion shape.

Although the first embodiment of the implant 5 includes either the transition section 29 or the transition sections 31 and 32 to produce deformation thereof, one of ordinary skill in the art will recognize that the bridge 14 of the implant 5 may include both the transition section 29 and the transition sections 31 and 32 to produce deformation thereof. Moreover, while the bridge 14 in the first embodiment includes an angular profile in the natural shape of the implant 5, it should be understood by one of ordinary skill in the art that a bridge 14 incorporating the transition sections 31 and 32 may include a substantially linear profile for the natural shape of the implant 5. In particular, when the implant 5 exerts a compressive force to bone, bones, or bone pieces, the bridge 14, as illustrated in FIG. 14, includes a substantially linear profile in the natural shape of the implant 5. Furthermore, the bridge 14, as shown in FIG. 15, maintains its substantially linear profile once the implant 5 deforms to an insertion shape. Conversely, when the implant 5 exerts a distractive force to bone, bones, or bone pieces, FIG. 15 illustrates the implant 5 in a natural shape, whereas FIG. 14 illustrates the implant 5 in an insertion shape.

An implantation of the implant 5 into bone, bones, or bone pieces includes the bridge 14 spanning a fixation zone of the bone, bones, or bone pieces with the leg 21 inserting into the bone, bones, or bone pieces adjacent a first side of the fixation zone and the leg 22 inserting into the bone, bones, or bone pieces adjacent a second side of the fixation zone followed by an attempted transition of the implant 5 from its insertion shape 7 to its natural shape 6 and a corresponding delivery of energy to the bone, bones, or bone pieces at the fixation zone. In order to enhance implantation of the implant 5 into the bone, bones, or bone pieces including an ability of the implant 5 to overcome any implantation issues associated with bone, bones, or bone pieces of poorer quality, the implant 5 includes the cannulation 8 that traverses the bridge 14 and the leg 21 until exiting the leg 21 at the outlets 11 and the cannulation 9 that traverses the bridge 14 and the leg 22 until exiting the leg 22 at the outlets 13. During implantation of the implant 5, a bone augmentation material introduced into the cannulation 8 via its inlet 10 traverses the cannulation 8 and then exits the cannulation 8 at its outlets 11 such that the bone augmentation material enters the bone, bones, or bone pieces around the leg 21 and its tip 23. Likewise, a bone augmentation material introduced into the cannulation 9 via its inlet 12 traverses the cannulation 9 and then exits the cannulation 9 at its outlets 13 such that the bone augmentation material enters the bone, bones, or bone pieces around the leg 22 and its tip 24. The bone augmentation material fills the bone, bones, or bone pieces around the legs 21 and 22, and, once its sets or cures, the bone augmentation material enhances the structural integrity of the bone, bones, or bone pieces whereby the bone, bones, or bone pieces receive energy imparted thereto from the implant 5 without experiencing a structural failure that causes a loss of fixation and subsequent improper fusion or distraction thereof. The bone augmentation material accordingly augments the bone, bones, or bone pieces resulting in the bone, bones, or bone pieces arresting movement of the legs 21 and 22 from their insertion position to their natural position during an attempted transition of the bridge 14 from its insertion form to its natural form such that the implant 5 imparts a force sufficient to fuse or distract the bone, bones, or bone pieces.

FIGS. 16-21 illustrate an orthopedic implant 50 according to a second embodiment in a natural shape 51, whereas FIGS. 22-27 illustrate the orthopedic implant 50 in an insertion shape 52. The implant 50 in the second embodiment may be manufactured from a shape memory material with superelastic or temperature dependent properties (e.g., Nitinol) such that the implant 50 transitions between its natural shape 51 and its insertion shape 52. The implant 50 when deformed from its natural shape 51 to its insertion shape 52 stores energy deliverable to bone, bones, or bone pieces. In accordance with its manufacture from shape memory material, the implant 50 begins in its natural shape 51, is transitionable to its insertion shape 52, and, once implanted in bone, bones, or bone pieces, attempts to transition from its insertion shape 52 to its natural shape 51 whereby the implant 50 delivers the energy stored therein to the bone, bones, or bone pieces in order to affix the bone, bones, or bone pieces and promote a healing thereof. In the first embodiment, attempted transition of the implant 50 from its insertion shape 52 to its natural shape 51 continuously compresses the bone, bones, or bone pieces to promote fusion thereof. Nevertheless, one of ordinary skill in the art will recognize that the attempted transition of the implant 50 from its insertion shape 52 to its natural shape 51 may distract the bone, bones, or bone pieces to hold the bone, bones, or bone pieces in an arrangement that promotes a healing thereof. In a distraction configuration, FIGS. 22-27 would illustrate an orthopedic implant 5 in a natural shape, whereas FIGS. 16-21 would illustrate the orthopedic implant 5 in an insertion shape.

When the implant 50 inserts into bone, bones, or bone pieces of a patient having a typical bone quality, the bone, bones, or bone pieces exhibit a structural integrity sufficient to arrest movement of the implant 50 during its attempted transition from its insertion shape 52 to its natural shape 51 such that the implant 50 imparts a force adequate to fuse or distract the bone, bones, or bone pieces. Conversely, when the implant 50 inserts into bone, bones, or bone pieces of a patient with a poorer bone quality, due to osteoporosis, trauma, or the like, the bone, bones, or bone pieces lack structural integrity sufficient to arrest movement of the implant 50 during its attempted transition from its insertion shape 52 to its natural shape 51 such that the implant 50 over-transitions resulting in the implant 50 failing to impart a force adequate to properly fuse or distract the bone, bones, or bone pieces. As a consequence, the bone, bones, or bone pieces of poorer quality may experience a loss of fixation and subsequent improper fusion or distraction thereof.

In order to enhance implantation of the implant 50 into bone, bones, or bone pieces including an ability of the implant 50 to overcome any implantation issues associated with bone, bones, or bone pieces of poorer quality, the implant 50 includes at least one cannulation 53 and, in the second embodiment, a second cannulation 54 as well as a third cannulation 55 and a fourth cannulation 56 when additional enhancement is desired. The cannulation 53 includes an inlet 57 and at least one outlet 61 and, in the second embodiment, multiple outlets 61. Likewise, the cannulation 54 includes an inlet 58 and at least one outlet 62 and, in the second embodiment, multiple outlets 62; the cannulation 55 includes an inlet 59 and at least one outlet 63 and, in the second embodiment, multiple outlets 63; and the cannulation 56 includes an inlet 60 and at least one outlet 64 and, in the second embodiment, multiple outlets 64. During the insertion of the implant 50 into bone, bones, or bone pieces, the cannulation 53 permits introduction of a bone augmentation material, such as bone cement, into the bone, bones, or bone pieces whereby the bone augmentation material enters and fills the bone, bones, or bone pieces to augment the structural integrity thereof. In particular, the bone augmentation material enters the cannulation 53 via its inlet 57, traverses the cannulation 53, and then exits the cannulation 53 via its one or more outlets 61 into the bone, bones, or bone pieces. The bone augmentation material fills the bone, bones, or bone pieces, and, once its sets or cures, the bone augmentation material enhances the structural integrity of the bone, bones, or bone pieces whereby the bone, bones, or bone pieces receive energy imparted thereto from the implant 50 without experiencing a structural failure that causes a loss of fixation and subsequent improper fusion or distraction thereof. The bone augmentation material accordingly augments the bone, bones, or bone pieces resulting in the bone, bones, or bone pieces arresting movement of the implant 50 during its attempted transition from its insertion shape 52 to its natural shape 51 such that the implant 50 imparts a force sufficient to fuse or distract the bone, bones, or bone pieces. Similar to the cannulation 53, the cannulations 54-56 permit introduction of a bone augmentation material, such as bone cement, into the bone, bones, or bone pieces during the insertion of the implant 50 into bone, bones, or bone pieces. The bone augmentation material enters the cannulations 54-56 via their respective inlets 58-60, traverses the cannulations 54-56, and then exits the cannulations 54-56 via their respective one or more outlets 62-64 into the bone, bones, or bone pieces. The cannulations 54-56 accordingly delivers the bone augmentation material into the bone, bones, or bone pieces at locations different from that of the cannulation 54 whereby the bone augmentation material enters and fills the bone, bones, or bone pieces to further augment the structural integrity thereof.

In the second embodiment, the implant 50 includes a bridge 65 with a three-dimensional form having a length, width, and height, and, in particular, the bridge 65 includes a central axis 72 and an upper surface 66 and a lower surface 67 with first and second sides 68 and 69 and first and second ends 70 and 71 therebetween. The bridge 65 is tapered to present a non-uniform cross-sectional thickness between the upper and lower surfaces 66 and 67 in order to provide strength to the bridge 65 while lowering its profile. Although the bridge 65 is tapered in the second embodiment, one of ordinary skill in the art will recognize that the bridge 65 may include a uniform cross-sectional thickness between the upper and lower surfaces 66 and 67.

The implant 50 in the second embodiment includes an anchoring member in the form of a leg 73 extending from the lower surface 67 of the bridge 65 at its end 70, an anchoring member in the form of a leg 74 extending from the lower surface 67 of the bridge 65 at its end 71, an anchoring member in the form of a leg 75 extending from the lower surface 67 of the bridge 65 between the central axis 72 of the bridge 65 and the leg 73, and an anchoring member in the form of a leg 76 extending from the lower surface 67 of the bridge 65 between the central axis 72 of the bridge 65 and the leg 74. In the second embodiment, the legs 73 and 74 are formed integrally with the bridge 65 at a respective end 70 and 71, while the legs 75 and 76 are formed integrally with the bridge 66 between the central axis 72 of the bridge 65 and a respective leg 73 and 74. Each leg 73-76, which has a respective tip 77-80, may include barbs thereon that improve the pull-out resistance of the implant 50. The implant 50 includes anchoring members in the form of legs 73-76 in order to facilitate a securing of the implant 50 with bone, bones, or bone pieces whereby the bridge 65 and in particular a segment of the bridge 65 between the legs 75 and 76 traverses a fixation zone of the bone, bones, or bone pieces such that the implant 50, after its insertion and attempted transition from the insertion shape 52 to the natural shape 51, delivers energy to the bone, bones, or bone pieces at the fixation zone.

The cannulation 53 in the second embodiment of the implant 50 originates in the bridge 65 with its inlet 57 in the bridge 65 at the leg 75. The cannulation 53 traverses the bridge 65 and then the leg 75 until the cannulation 53 exits the leg 75 in at least one outlet 61 located at any point along the leg 75 including at the tip 79 such that the at least one outlet 61 delivers a bone augmentation material around the leg 75. While the cannulation 53 requires only a single outlet 61, the cannulation 53 in the second embodiment includes multiple outlets 61 located along an interior side 86 and an exterior side 87 of the leg 75 such that the multiple outlets 61 facilitate delivery of a bone augmentation material around the leg 75 and its tip 79. Nevertheless, one of ordinary skill in the art will recognize that the multiple outlets 61 may be located at any point along the leg 75 including at the tip 79. The cannulation 53 includes its inlet 57 located in the bridge 65 at the leg 75 to allow access thereto from the bridge 65 on the basis the bridge 65 resides atop bone, bones, or bone pieces after implantation of the implant 50. The cannulation 53 traverses the bridge 65 and the leg 75 and exits the leg 75 at the outlets 61 located in the leg 75 because, after implantation of the implant 50, the leg 75 resides in bone, bones, or bone pieces, thereby facilitating delivery of bone augmentation material into the bone, bones, or bone pieces via the cannulation 53.

The cannulation 54 in the second embodiment of the implant 50 originates in the bridge 65 with its inlet 58 in the bridge 65 at the leg 76. The cannulation 54 traverses the bridge 65 and then the leg 76 until the cannulation 54 exits the leg 76 in at least one outlet 62 located at any point along the leg 76 including at the tip 80 such that the at least one outlet 62 delivers a bone augmentation material around the leg 76. While the cannulation 54 requires only a single outlet 62, the cannulation 54 in the second embodiment includes multiple outlets 62 located along an interior side 88 and an exterior side 89 of the leg 76 such that the multiple outlets 62 facilitate delivery of a bone augmentation material around the leg 76 and its tip 80. Nevertheless, one of ordinary skill in the art will recognize that the multiple outlets 62 may be located at any point along the leg 76 including at the tip 80. The cannulation 54 includes its inlet 58 located in the bridge 65 at the leg 76 to allow access thereto from the bridge 65 on the basis the bridge 65 resides atop bone, bones, or bone pieces after implantation of the implant 50. The cannulation 54 traverses the bridge 65 and the leg 76 and exits the leg 76 at the outlets 62 located in the leg 76 because, after implantation of the implant 50, the leg 76 resides in bone, bones, or bone pieces, thereby facilitating delivery of bone augmentation material into the bone, bones, or bone pieces via the cannulation 54.

The cannulation 55 in the second embodiment of the implant 50 originates in the bridge 65 with its inlet 59 in the bridge 65 at the leg 73 adjacent the end 70 of the bridge 65. The cannulation 55 traverses the bridge 65 and then the leg 73 until the cannulation 55 exits the leg 73 in at least one outlet 63 located at any point along the leg 73 including at the tip 77 such that the at least one outlet 63 delivers a bone augmentation material around the leg 73. While the cannulation 55 requires only a single outlet 63, the cannulation 55 in the second embodiment includes multiple outlets 63 located along an interior side 90 and an exterior side 91 of the leg 73 such that the multiple outlets 63 facilitate delivery of a bone augmentation material around the leg 73 and its tip 77. Nevertheless, one of ordinary skill in the art will recognize that the multiple outlets 63 may be located at any point along the leg 73 including at the tip 77. The cannulation 55 includes its inlet 59 located in the bridge 65 at the leg 73 adjacent the end 70 to allow access thereto from the bridge 65 on the basis the bridge 65 resides atop bone, bones, or bone pieces after implantation of the implant 50. The cannulation 55 traverses the bridge 65 and the leg 73 and exits the leg 73 at the outlets 63 located in the leg 73 because, after implantation of the implant 50, the leg 73 resides in bone, bones, or bone pieces, thereby facilitating delivery of bone augmentation material into the bone, bones, or bone pieces via the cannulation 55.

The cannulation 56 in the second embodiment of the implant 50 originates in the bridge 65 with its inlet 60 in the bridge 65 at the leg 74 adjacent the end 71 of the bridge 65. The cannulation 56 traverses the bridge 65 and then the leg 74 until the cannulation 56 exits the leg 74 in at least one outlet 64 located at any point along the leg 74 including at the tip 78 such that the at least one outlet 64 delivers a bone augmentation material around the leg 74. While the cannulation 56 requires only a single outlet 64, the cannulation 56 in the second embodiment includes multiple outlets 64 located along an interior side 92 and an exterior side 93 of the leg 74 such that the multiple outlets 64 facilitate delivery of a bone augmentation material around the leg 74 and its tip 78. Nevertheless, one of ordinary skill in the art will recognize that the multiple outlets 64 may be located at any point along the leg 74 including at the tip 78. The cannulation 56 includes its inlet 60 located in the bridge 65 at the leg 74 adjacent the end 71 to allow access thereto from the bridge 65 on the basis the bridge 65 resides atop bone, bones, or bone pieces after implantation of the implant 50. The cannulation 55 traverses the bridge 65 and the leg 74 and exits the leg 74 at the outlets 64 located in the leg 74 because, after implantation of the implant 50, the leg 74 resides in bone, bones, or bone pieces, thereby facilitating delivery of bone augmentation material into the bone, bones, or bone pieces via the cannulation 56.

In the second embodiment, the bridge 65 includes a transition section 81 disposed at the central axis 72 thereof. The regular inherent shape of the implant 50 according to the first embodiment, as illustrated in FIGS. 16-21, is its natural shape 51 where the transition section 81 locates the bridge 65 in a natural form consisting of a closed or angular profile whereby the first and second ends 70 and 71 reside at a first distance and the legs 73-76 reside in a natural position whereby the legs 73 and 75 are convergent with and spaced apart at a first distance from the legs 74 and 76. Nevertheless, as illustrated in FIGS. 22-27, the implant 50 is deformable under the action of superelasticity or temperature dependent shape memory to its insertion shape 52 where the transition section 81 deforms to store energy while also moving the bridge 65 from its natural form to an insertion form which, in the second embodiment, is an open or substantially linear profile whereby the first and second ends 70 and 71 reside at a second distance that is greater than the first distance and the legs 73-76 reside in an insertion position whereby the legs 73 and 75 are substantially parallel with and spaced apart at a second distance that is greater than the first distance from the legs 74 and 76. Since the insertion shape 52 is not the regular inherent shape of the implant 50, the transition section 81 typically is mechanically constrained or chilled until it reaches its martensite phase whereby the transition section 81 once deformed maintains the bridge 65 in its insertion form. After implantation into bone, bones, or bone pieces and a release of a mechanical constraint or a heating of the implant 50 to its austenite phase, the implant 50 delivers the energy stored in the transition section 81 such that the bridge 65 attempts to transition from its insertion form to its natural form, resulting in the legs 73-76 attempting to move from their insertion position to their natural position whereby the implant 50 affixes the bone, bones, or bone pieces through an application of a compressive force thereto.

While the transition section 81 of the bridge 65 has been described as moving to create compression, one of ordinary skill in the art will recognize that movement of the transition section 81 and attempted transition of the bridge 65 from its insertion form to its natural form may distract bone, bones, or bone pieces to hold the bone, bones, or bone pieces in an arrangement that promotes a healing thereof. In a distraction configuration, FIGS. 22-27 would illustrate an orthopedic implant 50 in a natural shape, whereas FIGS. 16-21 would illustrate the orthopedic implant 50 in an insertion shape. The transition section 81 for distraction locates the bridge 65 in a natural form consisting of an open or substantially linear profile whereby the first and second ends 70 and 71 reside at a first distance and the legs 73-76 reside in a natural position whereby the legs 73 and 75 are substantially parallel with and spaced apart at a first distance from the legs 74 and 76. Nevertheless, the transition section 81 deforms to store energy while also moving the bridge 65 from its natural form to an insertion form which is a closed or angular profile whereby the first and second ends 70 and 71 reside at a second distance that is less than the first distance and the legs 73-76 reside in an insertion position whereby the legs 73 and 75 are convergent with and spaced apart at a second distance that is less than the first distance from the legs 74 and 76. Upon implantation into bone, bones, or bone pieces and a release of a mechanical constraint or a heating of the implant 50 to its austenite phase, the implant 50 delivers the energy stored in the transition section 81 such that the bridge 65 attempts to transition from its insertion form to its natural form, resulting in the legs 73-76 attempting to move from their insertion position to their natural position whereby the implant 50 affixes the bone, bones, or bone pieces through an application of a distractive force thereto.

Figure 28:
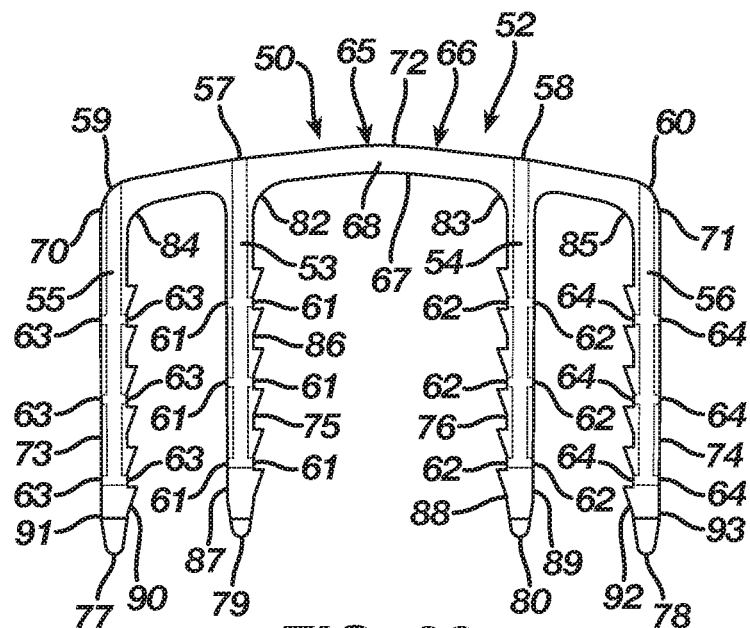
FIG. 28 is a side view of a shape memory implant according to an alternative of the second embodiment in an insertion shape.

Alternatively, the bridge 65 in the second embodiment may include transition sections 82 and 83 located respectively where the legs 75 and 76 extend from the bridge 65, and, in addition thereto when supplementary transition is desired, the bridge 65 may include transition sections 84 and 85 located respectively where the legs 73 and 74 extend from the bridge 65. The regular inherent shape of the implant 50, as illustrated in FIGS. 16-21, is its natural shape 51 where the transition sections 82 and 83 and if included the transition sections 84 and 85 locate the bridge 65 in a natural form that places the legs 73-76 in a natural position whereby the legs 73 and 75 are convergent with and spaced apart at a first distance from the legs 74 and 76. Nevertheless, as illustrated in FIG. 28, the implant 50 is deformable under the action of superelasticity or temperature dependent shape memory to an insertion shape 52 where the transition sections 82 and 83 and if included the transition sections 84 and 85 deform to store energy while also moving the bridge 65 from its natural form to an insertion form that places the legs 73-76 in an insertion position whereby the legs 73 and 75 are substantially parallel with and spaced apart at a second distance that is greater than the first distance from the legs 74 and 76. Since the insertion shape 52 is not the regular inherent shape of the implant 50, the transition sections 82 and 83 typically are mechanically constrained or chilled along with the transition sections 84 and 85 if included until they reach their martensite phase whereby the transition sections 82-85 once deformed maintain the bridge 65 in its insertion form. After implantation into bone, bones, or bone pieces and a release of a mechanical constraint or a heating of the implant 50 to its austenite phase, the implant 50 delivers the energy stored in the transition sections 82 and 83 and if included the transition sections 84 and 85 such that the bridge 65 attempts to transition from its insertion form to its natural form, resulting in the legs 73-76 attempting to move from their insertion position to their natural position whereby the implant 50 affixes the bone, bones, or bone pieces through an application of a compressive force thereto.

While the transition sections 82 and 83 and if included the transition sections 84 and 85 of the bridge 65 have been described as moving to create compression, one of ordinary skill in the art will recognize that movement of the transition sections 82-85 and attempted transition of the bridge 14 from its insertion form to its natural form may distract bone, bones, or bone pieces to hold the bone, bones, or bone pieces in an arrangement that promotes a healing thereof. In a distraction configuration, FIG. 28 would illustrate an orthopedic implant 50 in a natural shape, whereas FIGS. 16-21 would illustrate the orthopedic implant 50 in an insertion shape. The transition sections 82 and 83 and if included the transition sections 84 and 85 for distraction locate the bridge 65 in a natural form that places the legs 73-76 in a natural position whereby the legs 73 and 75 are substantially parallel with and spaced apart at a first distance from the legs 74 and 76. Nevertheless, the transition sections 82 and 83 and if included the transition sections 84 and 85 deform to store energy while also moving the bridge 65 from its natural form to an insertion form that places the legs 73-76 in an insertion position whereby the legs 73 and 75 are convergent with and spaced apart at a second distance that is less than the first distance from the legs 74 and 76. Upon implantation into bone, bones, or bone pieces and a release of a mechanical constraint or a heating of the implant 50 to its austenite phase, the implant 50 delivers the energy stored in the transition sections 82 and 83 and if included the transition sections 84 and 85 such that the bridge 65 attempts to transition from its insertion form to its natural form, resulting in the legs 73-76 attempting to move from their insertion position to their natural position whereby the implant 50 affixes the bone, bones, or bone pieces through an application of a distractive force thereto.

Figure 29:
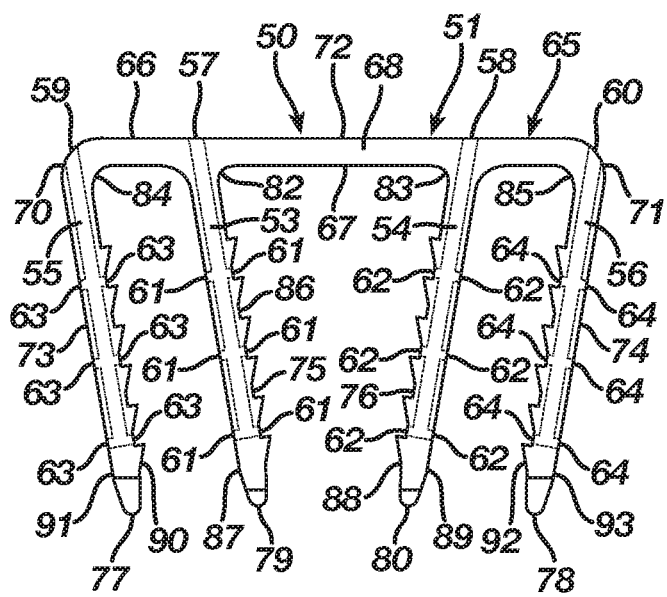
FIG. 29 is a side view of a shape memory implant according to an alternative of the second embodiment in a natural shape.
Figure 30:
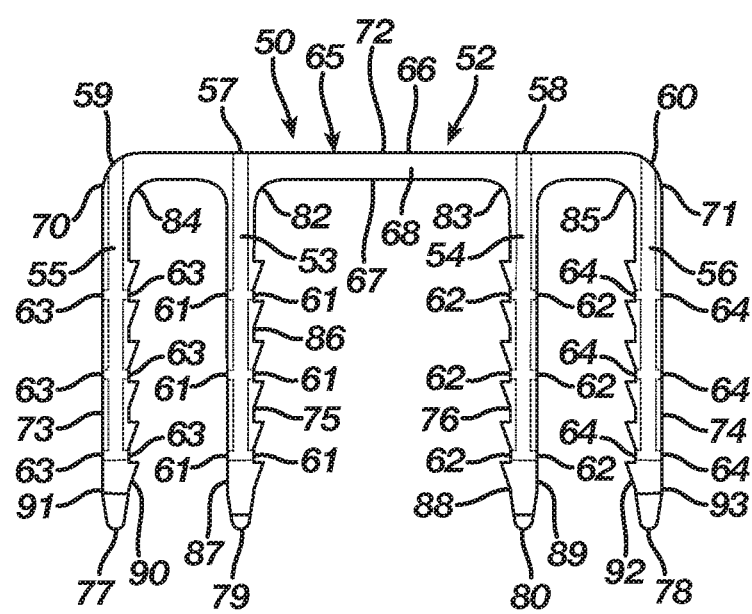
FIG. 30 is a side view of a shape memory implant according to an alternative of the second embodiment in an insertion shape.
Figure 31:
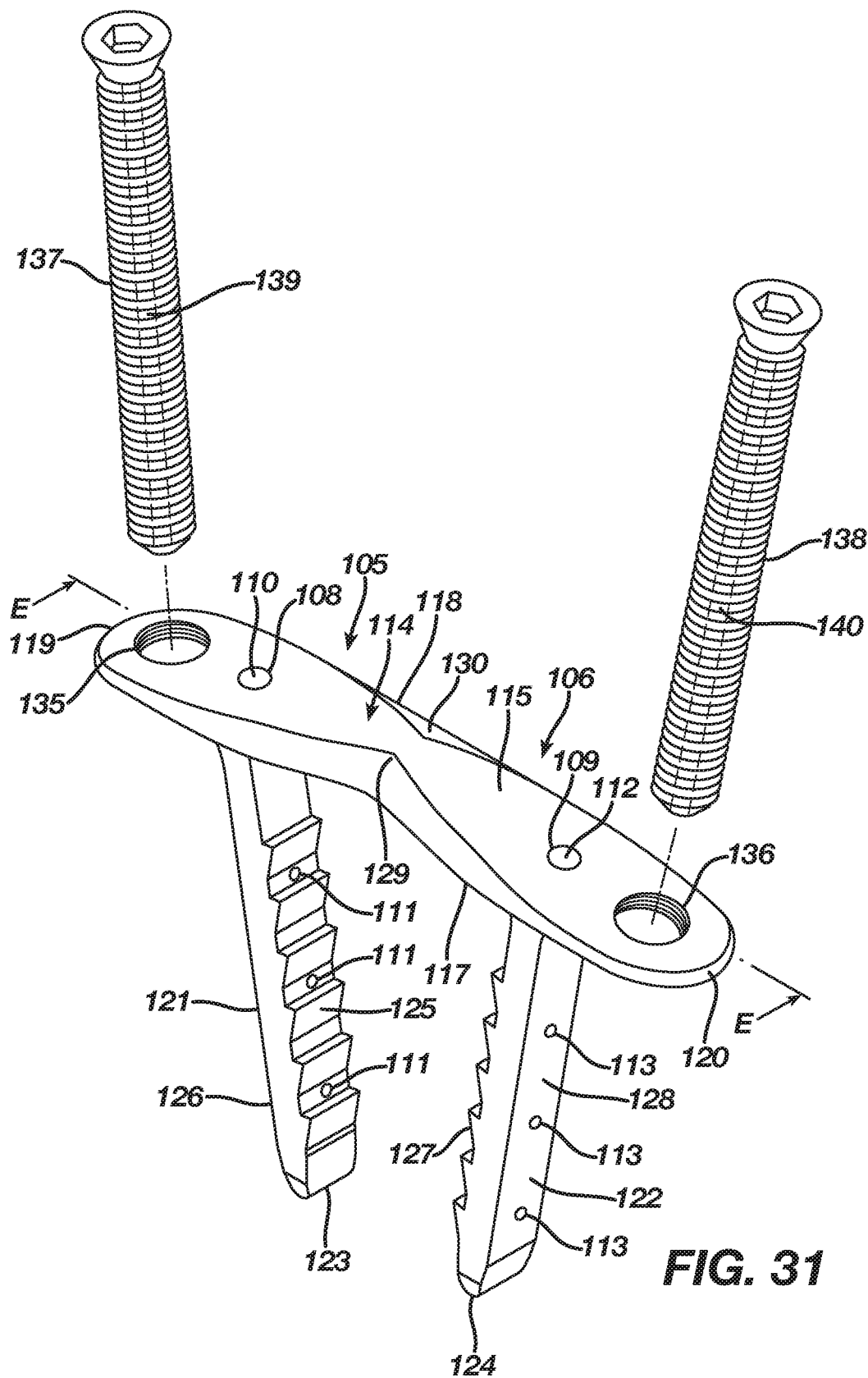
FIG. 31 is an isometric view illustrating a shape memory implant according to a third embodiment in a natural shape.
Figure 32:
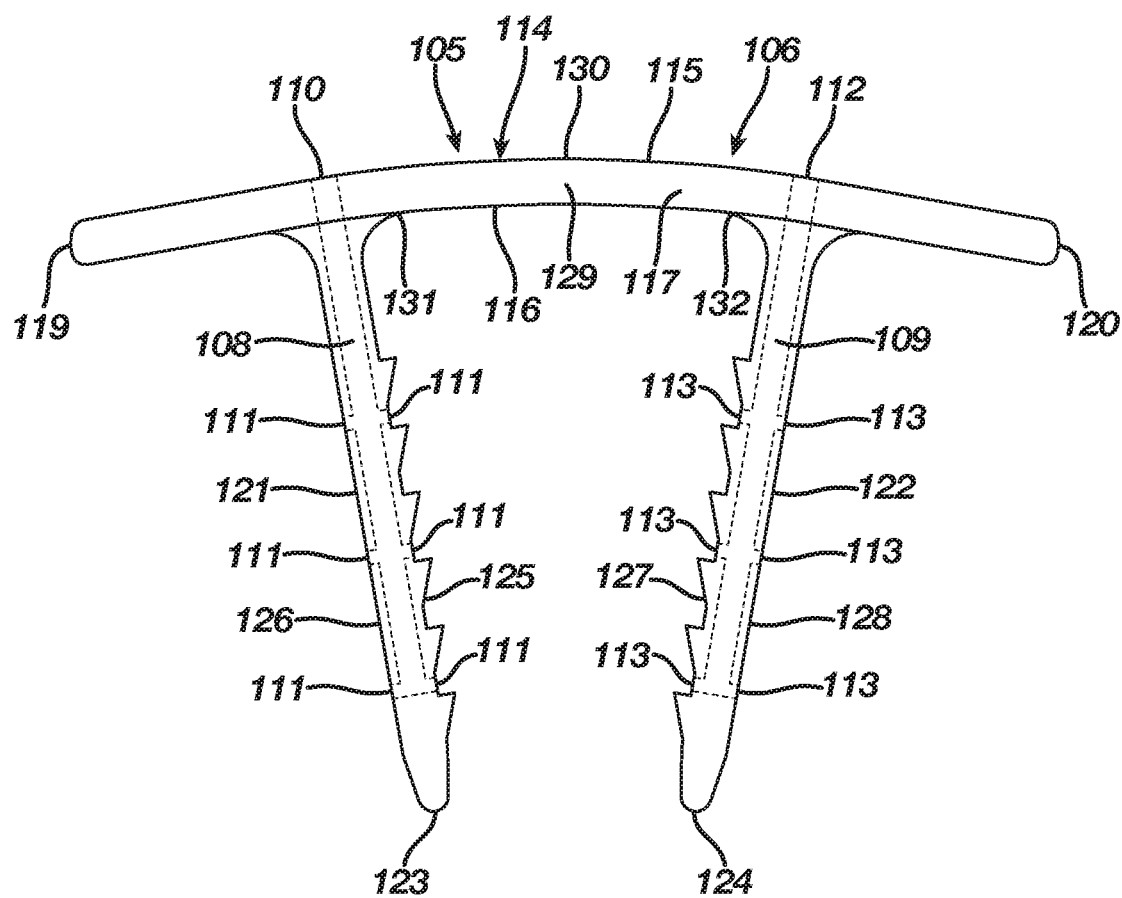
FIG. 32 is a side view thereof.
Figure 33:
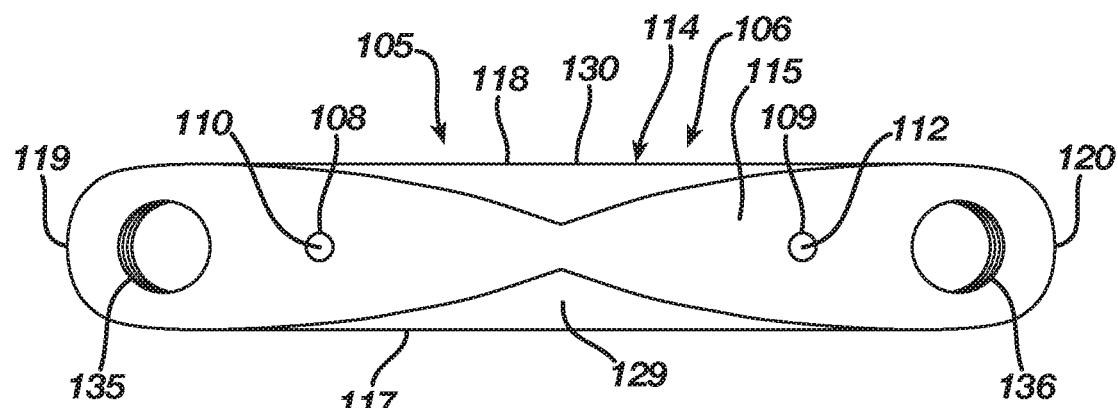
FIG. 33 is a top view thereof.
Figure 34:
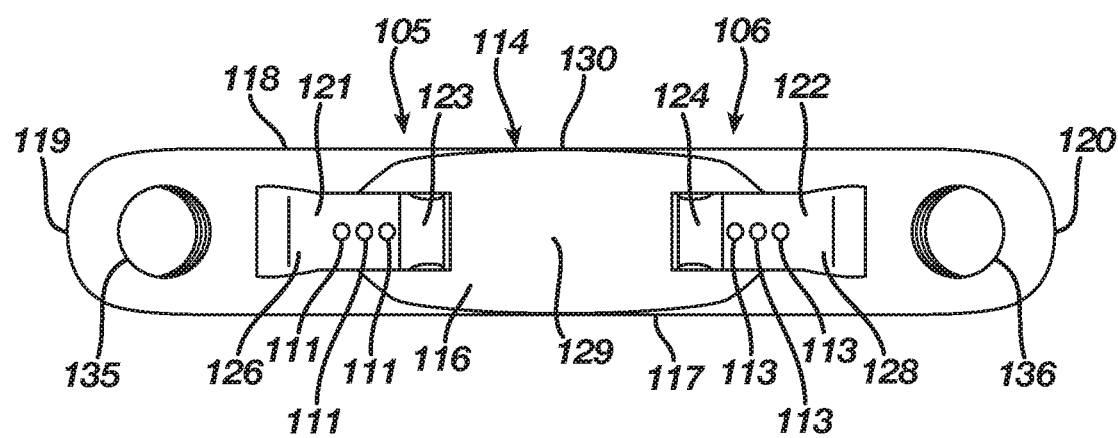
FIG. 34 is a bottom view thereof.
Figure 35:
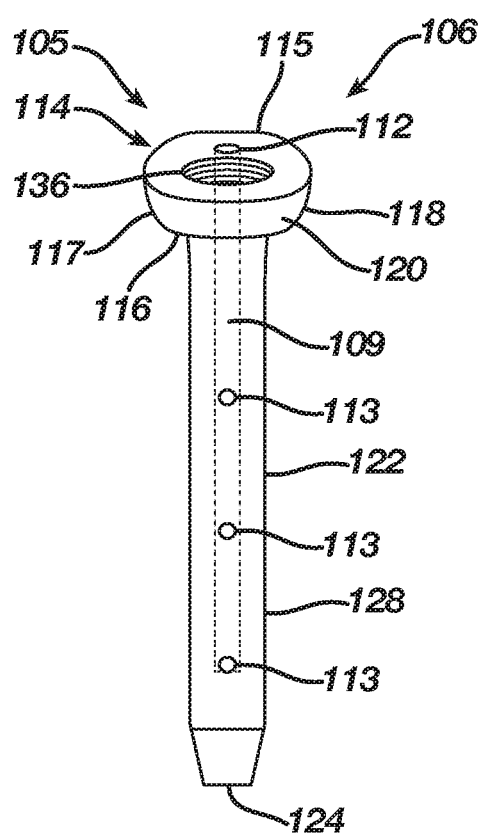
FIG. 35 is an end view thereof.
Figure 36:
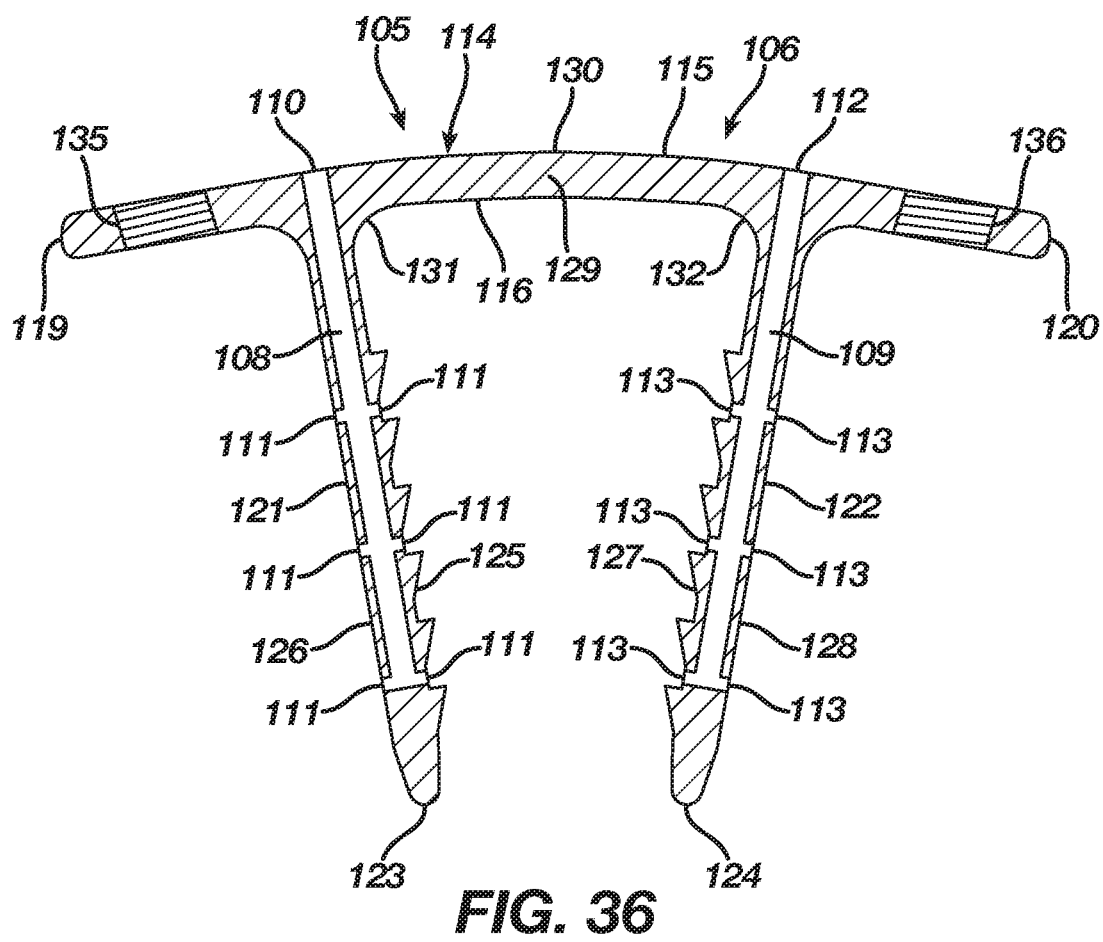
FIG. 36 is a cross-sectional view taken along lines E-E of FIG. 31 illustrating the shape memory implant according to the third embodiment in its natural shape.
Figure 37:
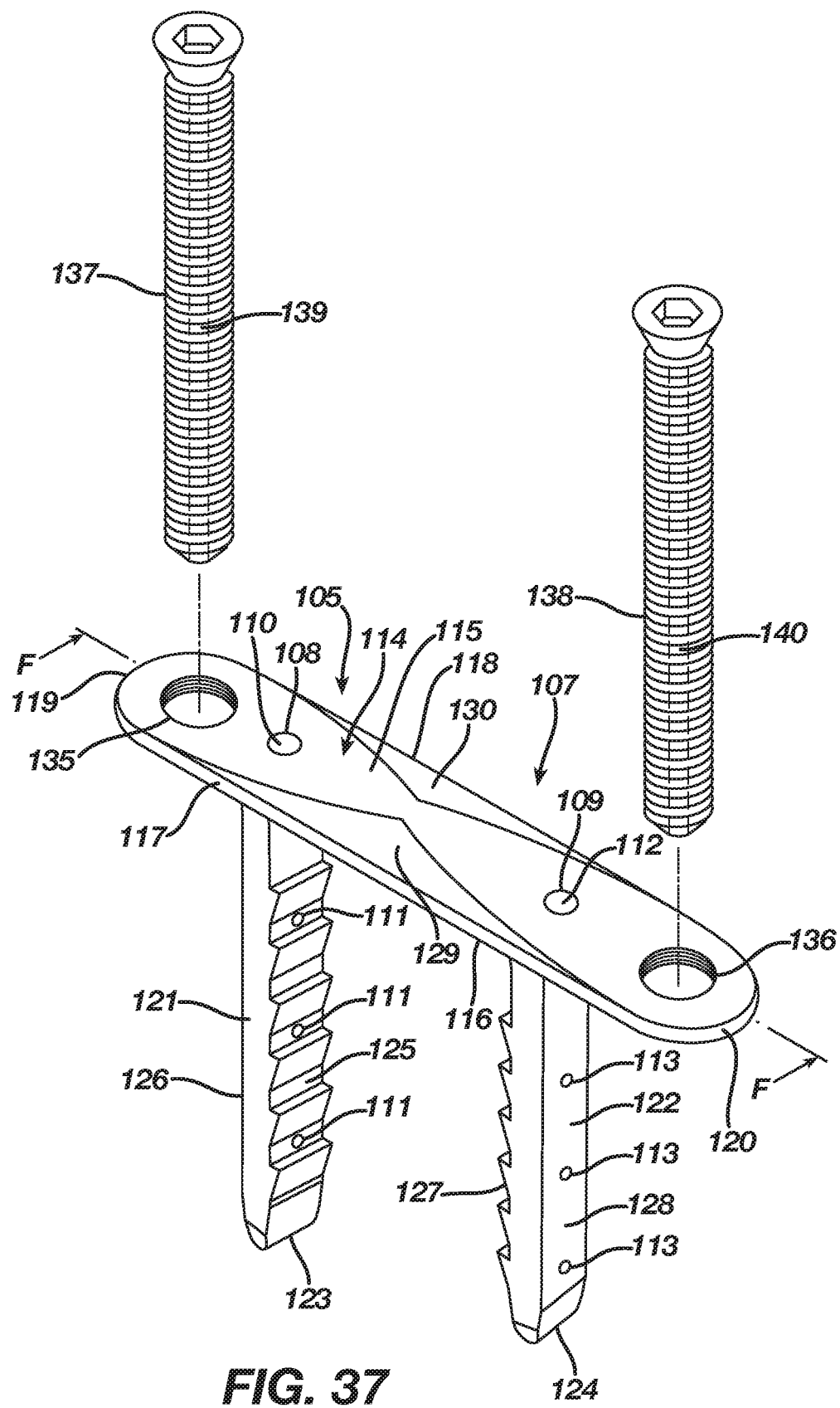
FIG. 37 is an isometric view illustrating the shape memory implant according to the third embodiment in an insertion shape.
Figure 38:
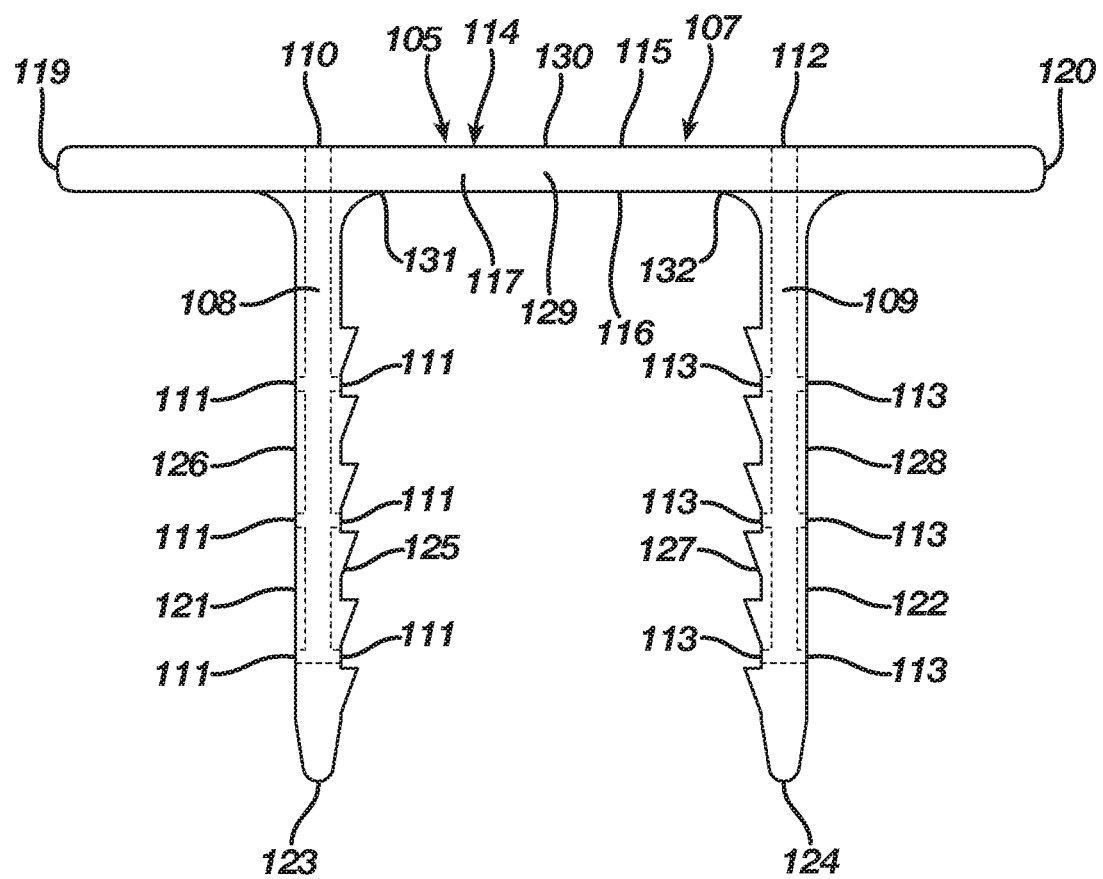
FIG. 38 is a side view thereof.
Figure 39:
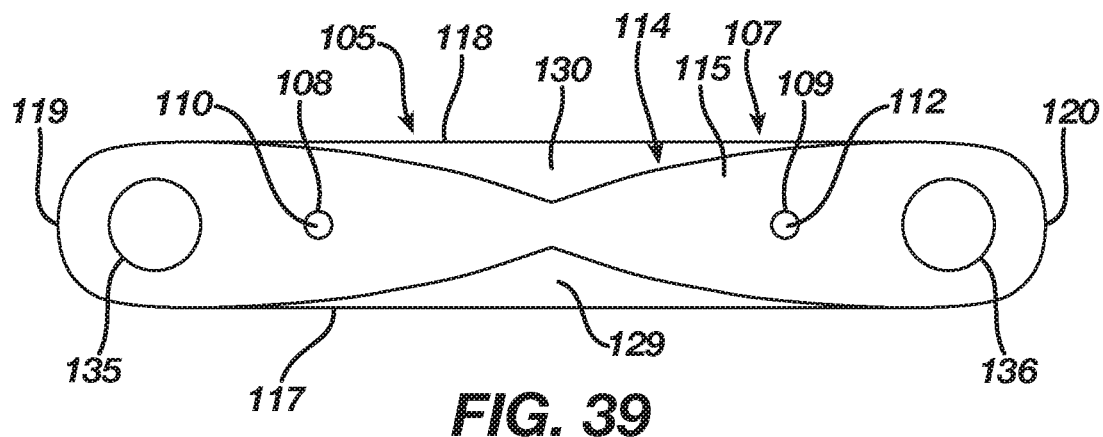
FIG. 39 is a top view thereof.
Figure 40:
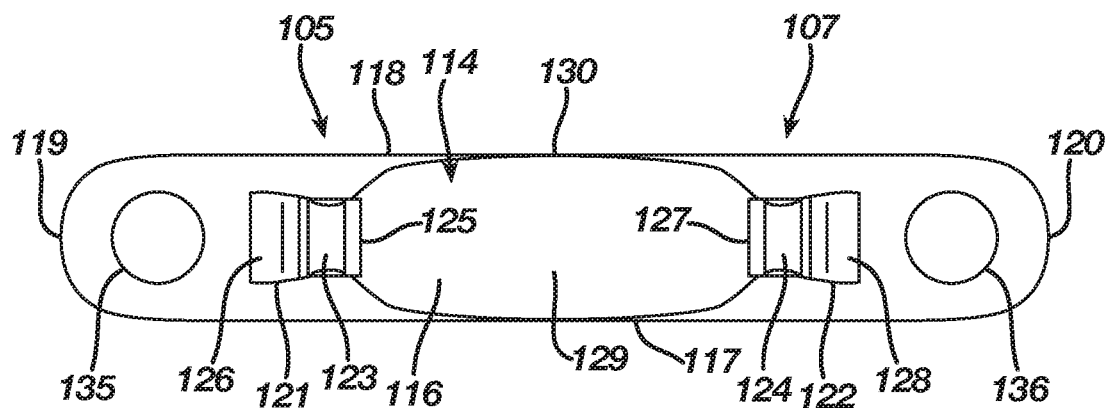
FIG. 40 is a bottom view thereof.
Figure 41:
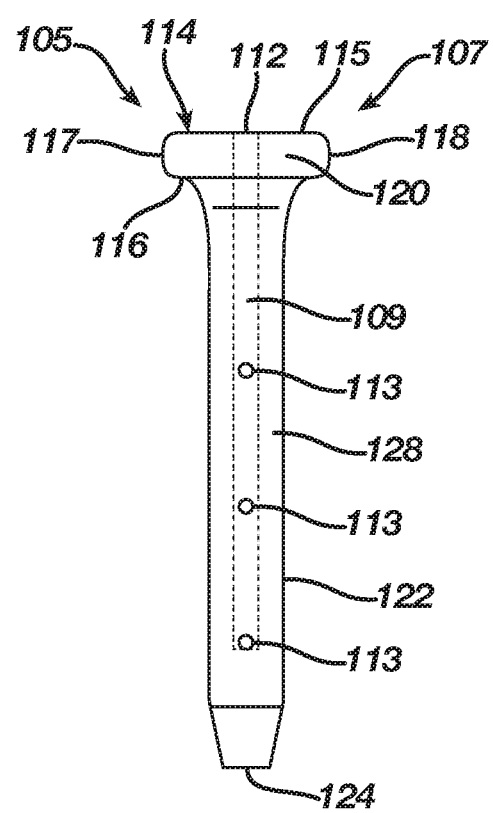
FIG. 41 is an end view thereof.
Figure 42:
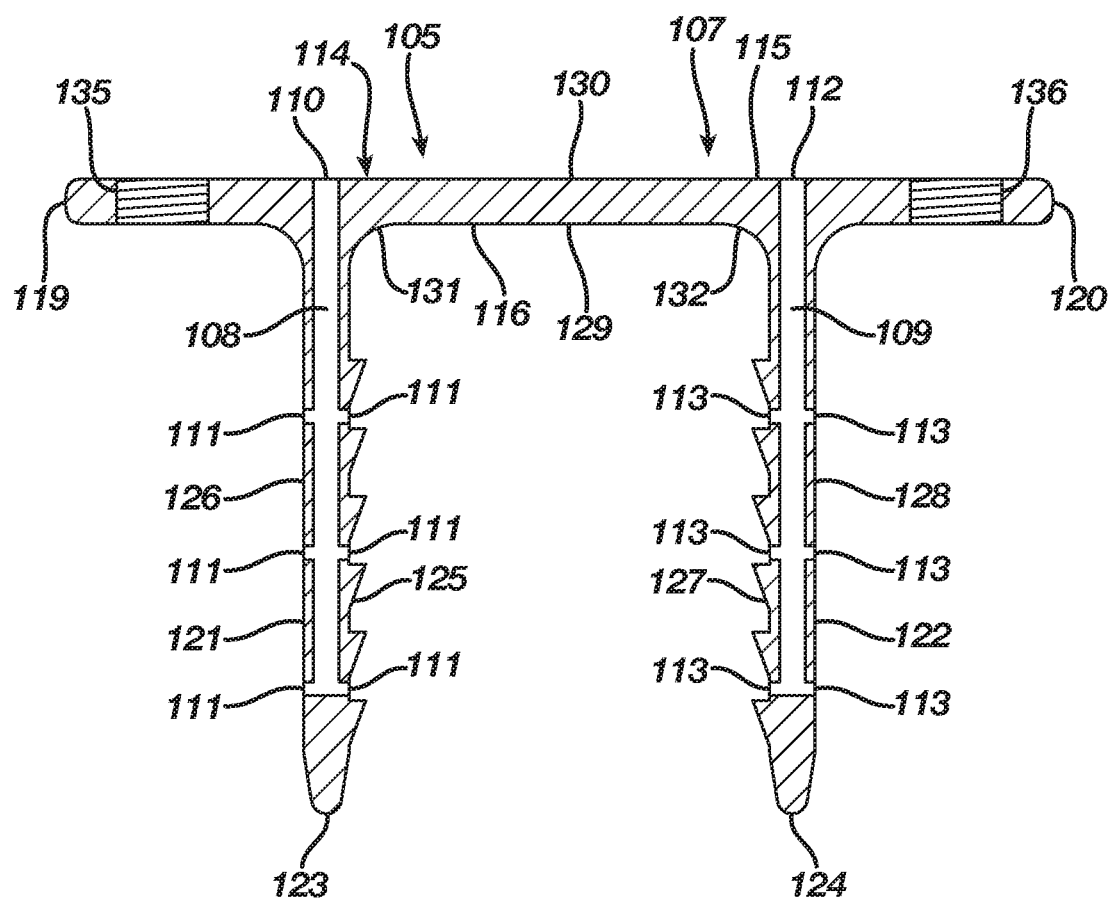
FIG. 42 is a cross-sectional view taken along lines F-F of FIG. 37 illustrating the shape memory implant according to the third embodiment in its insertion shape.

Although the first embodiment of the implant 50 includes either the transition section 81 or the transition sections 82 and 83 and if included the transition sections 84 and 85 to produce deformation thereof, one of ordinary skill in the art will recognize that the bridge 65 of the implant 50 may include both the transition section 81 and the transition sections 82 and 83 along with the transition sections 84 and 85 if included to produce deformation thereof. Moreover, while the bridge 65 in the second embodiment includes an angular profile in the natural shape of the implant 50, it should be understood by one of ordinary skill in the art that a bridge 65 incorporating the transition sections 82 and 83 and if included the transition sections 84 and 85 may include a substantially linear profile for the natural shape of the implant 50. In particular, when the implant 50 exerts a compressive force to bone, bones, or bone pieces, the bridge 65, as illustrated in FIG. 29, includes a substantially linear profile in the natural shape of the implant 50. Furthermore, the bridge 65, as shown in FIG. 30, maintains its substantially linear profile once the implant 50 deforms to an insertion shape. Conversely, when the implant 50 exerts a distractive force to bone, bones, or bone pieces, FIG. 30 illustrates the implant 50 in a natural shape, whereas FIG. 29 illustrates the implant 50 in an insertion shape.

An implantation of the implant 50 into bone, bones, or bone pieces includes the bridge 65, and, in particular, a segment of the bridge 65 between the legs 75 and 76, spanning a fixation zone of the bone, bones, or bone pieces with the legs 73 and 75 inserting into the bone, bones, or bone pieces adjacent a first side of the fixation zone and the legs 74 and 76 inserting into the bone, bones, or bone pieces adjacent a second side of the fixation zone followed by an attempted transition of the implant 50 from its insertion shape 52 to its natural shape 51 and a corresponding delivery of energy to the bone, bones, or bone pieces at the fixation zone. In order to enhance implantation of the implant 50 into the bone, bones, or bone pieces including an ability of the implant 50 to overcome any implantation issues associated with bone, bones, or bone pieces of poorer quality, the implant 50 includes the cannulation 53 that traverses the bridge 65 and the leg 75 until exiting the leg 75 at the outlets 61, the cannulation 54 that traverses the bridge 65 and the leg 76 until exiting the leg 76 at the outlets 62, the cannulation 55 that traverses the bridge 65 and the leg 73 until exiting the leg 73 at the outlets 63, and the cannulation 56 that traverses the bridge 65 and the leg 74 until exiting the leg 74 at the outlets 64. During implantation of the implant 50, a bone augmentation material introduced into the cannulation 53 via its inlet 61 traverses the cannulation 53 and then exits the cannulation 53 at its outlets 61 such that the bone augmentation material enters the bone, bones, or bone pieces around the leg 75 and its tip 79. Likewise, a bone augmentation material introduced into the cannulations 54-56 via their respective inlets 58-60 traverses the cannulations 54-56 and then exits the cannulations 54-56 at their respective outlets 62-64 such that the bone augmentation material enters the bone, bones, or bone pieces around the legs 73, 74, and 76 and their respective tips 77, 78, and 80. The bone augmentation material fills the bone, bones, or bone pieces around the legs 73-76, and, once its sets or cures, the bone augmentation material enhances the structural integrity of the bone, bones, or bone pieces whereby the bone, bones, or bone pieces receive energy imparted thereto from the implant 50 without experiencing a structural failure that causes a loss of fixation and subsequent improper fusion or distraction thereof. The bone augmentation material accordingly augments the bone, bones, or bone pieces resulting in the bone, bones, or bone pieces arresting movement of the legs 73-76 from their insertion position to their natural position during an attempted transition of the bridge 65 from its insertion form to its natural form such that the implant 50 imparts a force sufficient to fuse or distract the bone, bones, or bone pieces.

FIGS. 31-36 illustrate an orthopedic implant 105 according to a third embodiment in a natural shape 106, whereas FIGS. 37-42 illustrate the orthopedic implant 105 in an insertion shape 107. The implant 105 in the third embodiment may be manufactured from a shape memory material with superelastic or temperature dependent properties (e.g., Nitinol) such that the implant 105 transitions between its natural shape 106 and its insertion shape 107. The implant 105 when deformed from its natural shape 106 to its insertion shape 107 stores energy deliverable to bone, bones, or bone pieces. In accordance with its manufacture from shape memory material, the implant 105 begins in its natural shape 106, is transitionable to its insertion shape 107, and, once implanted in bone, bones, or bone pieces, attempts to transition from its insertion shape 107 to its natural shape 106 whereby the implant 105 delivers the energy stored therein to the bone, bones, or bone pieces in order to affix the bone, bones, or bone pieces and promote a healing thereof. In the third embodiment, attempted transition of the implant 105 from its insertion shape 107 to its natural shape 106 continuously compresses the bone, bones, or bone pieces to promote fusion thereof. Nevertheless, one of ordinary skill in the art will recognize that the attempted transition of the implant 105 from its insertion shape 107 to its natural shape 106 may distract the bone, bones, or bone pieces to hold the bone, bones, or bone pieces in an arrangement that promotes a healing thereof. In a distraction configuration, FIGS. 37-42 would illustrate an orthopedic implant 105 in a natural shape, whereas FIGS. 31-36 would illustrate the orthopedic implant 105 in an insertion shape.

When the implant 105 inserts into bone, bones, or bone pieces of a patient having a typical bone quality, the bone, bones, or bone pieces exhibit a structural integrity sufficient to arrest movement of the implant 105 during its attempted transition from its insertion shape 107 to its natural shape 106 such that the implant 105 imparts a force adequate to fuse or distract the bone, bones, or bone pieces. Conversely, when the implant 105 inserts into bone, bones, or bone pieces of a patient with a poorer bone quality, due to osteoporosis, trauma, or the like, the bone, bones, or bone pieces lack structural integrity sufficient to arrest movement of the implant 105 during its attempted transition from its insertion shape 107 to its natural shape 106 such that the implant 105 over-transitions resulting in the implant 105 failing to impart a force adequate to properly fuse or distract the bone, bones, or bone pieces. As a consequence, the bone, bones, or bone pieces of poorer quality may experience a loss of fixation and subsequent improper fusion or distraction thereof.

In order to enhance implantation of the implant 105 into bone, bones, or bone pieces including an ability of the implant 105 to overcome any implantation issues associated with bone, bones, or bone pieces of poorer quality, the implant 105 includes at least one cannulation 108 and, in the third embodiment, a second cannulation 109. The cannulation 108 includes an inlet 110 and at least one outlet 111 and, in the third embodiment, multiple outlets 111. Likewise, the cannulation 109 includes an inlet 112 and at least one outlet 113 and, in the third embodiment, multiple outlets 113. During the insertion of the implant 105 into bone, bones, or bone pieces, the cannulation 108 permits introduction of a bone augmentation material, such as bone cement, into the bone, bones, or bone pieces whereby the bone augmentation material enters and fills the bone, bones, or bone pieces to augment the structural integrity thereof. In particular, the bone augmentation material enters the cannulation 108 via its inlet 110, traverses the cannulation 108, and then exits the cannulation 108 via its one or more outlets 111 into the bone, bones, or bone pieces. The bone augmentation material fills the bone, bones, or bone pieces, and, once its sets or cures, the bone augmentation material enhances the structural integrity of the bone, bones, or bone pieces whereby the bone, bones, or bone pieces receive energy imparted thereto from the implant 105 without experiencing a structural failure that causes a loss of fixation and subsequent improper fusion or distraction thereof. The bone augmentation material accordingly augments the bone, bones, or bone pieces resulting in the bone, bones, or bone pieces arresting movement of the implant 105 during its attempted transition from its insertion shape 107 to its natural shape 106 such that the implant 105 imparts a force sufficient to fuse or distract the bone, bones, or bone pieces. Similar to the cannulation 108, the cannulation 109 permits introduction of a bone augmentation material, such as bone cement, into the bone, bones, or bone pieces during the insertion of the implant 105 into bone, bones, or bone pieces. The bone augmentation material enters the cannulation 109 via its inlet 112, traverses the cannulation 109, and then exits the cannulation 109 via its one or more outlets 113 into the bone, bones, or bone pieces. The cannulation 109 accordingly delivers the bone augmentation material into the bone, bones, or bone pieces at a location different from that of the cannulation 108 whereby the bone augmentation material enters and fills the bone, bones, or bone pieces to further augment the structural integrity thereof.

In the third embodiment, the implant 105 includes a bridge 114 with a three-dimensional form having a length, width, and height, and, in particular, the bridge 114 includes a central axis 130 and an upper surface 115 and a lower surface 116 with first and second sides 117 and 118 and first and second ends 119 and 120 therebetween. The bridge 114 is tapered to present a non-uniform cross-sectional thickness between the upper and lower surfaces 115 and 116 in order to provide strength to the bridge 114 while lowering its profile. Although the bridge 114 is tapered in the first embodiment, one of ordinary skill in the art will recognize that the bridge 114 may include a uniform cross-sectional thickness between the upper and lower surfaces 115 and 116.

The bridge 114 includes an aperture 135 therethrough that, in the third embodiment, is threaded and receives therethrough a fixation device 137, such as a non-locking or locking bone screw. The aperture 135 is positioned from the central axis 130 lengthwise along the bridge 114 to a location adjacent the end 119 of the bridge. The fixation device 137 engages the aperture 135 and further inserts into bone, bones, or bone pieces in order to assist in securing the implant 105 with the bone, bones, or bone pieces at the end 119 of the bridge 114. The fixation device 137 in the third embodiment may include a cannulation 139 therethrough that facilitates delivery of a bone augmentation material into bone, bones, or bone pieces at a location different from that of the cannulation 108 whereby the bone augmentation material enters and fills the bone, bones, or bone pieces to further augment the structural integrity thereof. Likewise, the bridge 114 includes an aperture 136 therethrough that, in the third embodiment, is threaded and receives therethrough a fixation device 138, such as a non-locking or locking bone screw. The aperture 136 is positioned from the central axis 130 lengthwise along the bridge 114 to a location adjacent the end 120 of the bridge 114. The fixation device 138 engages the aperture 136 and further inserts into bone, bones, or bone pieces in order to assist in securing the implant 105 with the bone, bones, or bone pieces at the end 120 of the bridge 114. The fixation device 138 in the third embodiment may include a cannulation 140 therethrough that facilitates delivery of a bone augmentation material into bone, bones, or bone pieces at a location different from that of the cannulation 109 whereby the bone augmentation material enters and fills the bone, bones, or bone pieces to further augment the structural integrity thereof.

The implant 105 in the third embodiment includes an anchoring member in the form of a leg 121 extending from the lower surface 116 of the bridge 114 between the central axis 130 of the bridge 114 and the aperture 135 adjacent the end 119 of the bridge 114 and an anchoring member in the form of a leg 122 extending from the lower surface 116 of the bridge 114 between the central axis 130 of the bridge 114 and the aperture 136 adjacent the end 120 of the bridge 114. In the third embodiment, the legs 121 and 122 are formed integrally with the bridge 114 between the central axis 130 of the bridge 114 and a respective aperture 135 and 136. Each leg 121 and 122, which has a respective tip 123 and 124, may include barbs thereon that improve the pull-out resistance of the implant 105. The implant 105 includes anchoring members in the form of legs 121 and 122 in order to facilitate a securing of the implant 105 with bone, bones, or bone pieces whereby the bridge 114 and in particular a segment of the bridge 114 between the legs 121 and 122 traverses a fixation zone of the bone, bones, or bone pieces such that the implant 105, after its insertion and attempted transition from the insertion shape 107 to the natural shape 106, delivers energy to the bone, bones, or bone pieces at the fixation zone.

The cannulation 108 in the third embodiment of the implant 105 originates in the bridge 114 with its inlet 110 in the bridge 114 at the leg 121. The cannulation 108 traverses the bridge 114 and then the leg 121 until the cannulation 108 exits the leg 121 in at least one outlet 111 located at any point along the leg 121 including at the tip 123 such that the at least one outlet 111 delivers a bone augmentation material around the leg 121. While the cannulation 108 requires only a single outlet 111, the cannulation 108 in the third embodiment includes multiple outlets 111 located along an interior side 125 and an exterior side 126 of the leg 121 such that the multiple outlets 111 facilitate delivery of a bone augmentation material around the leg 121 and its tip 123. Nevertheless, one of ordinary skill in the art will recognize that the multiple outlets 111 may be located at any point along the leg 121 including at the tip 123. The cannulation 108 includes its inlet 110 located in the bridge 114 at the leg 121 adjacent the end 119 of the bridge 114 to allow access thereto from the bridge 114 on the basis the bridge 114 resides atop bone, bones, or bone pieces after implantation of the implant 105. The cannulation 108 traverses the bridge 114 and the leg 121 and exits the leg 121 at the outlets 111 located in the leg 121 because, after implantation of the implant 105, the leg 121 resides in bone, bones, or bone pieces, thereby facilitating delivery of bone augmentation material into the bone, bones, or bone pieces via the cannulation 108.

The cannulation 109 in the third embodiment of the implant 105 originates in the bridge 114 with its inlet 112 in the bridge 114 at the leg 122. The cannulation 109 traverses the bridge 114 and then the leg 122 until the cannulation 109 exits the leg 122 in at least one outlet 113 located at any point along the leg 122 including at the tip 124 such that the at least one outlet 113 delivers a bone augmentation material around the leg 122. While the cannulation 109 requires only a single outlet 113, the cannulation 109 in the third embodiment includes multiple outlets 113 located along an interior side 127 and an exterior side 128 of the leg 122 such that the multiple outlets 113 facilitate delivery of a bone augmentation material around the leg 122 and its tip 124. Nevertheless, one of ordinary skill in the art will recognize that the multiple outlets 113 may be located at any point along the leg 122 including at the tip 124. The cannulation 109 includes its inlet 112 located in the bridge 114 at the leg 122 adjacent the end 120 of the bridge 114 to allow access thereto from the bridge 114 on the basis the bridge 114 resides atop bone, bones, or bone pieces after implantation of the implant 105. The cannulation 109 traverses the bridge 114 and the leg 122 and exits the leg 122 at the outlets 113 located in the leg 122 because, after implantation of the implant 105, the leg 122 resides in bone, bones, or bone pieces, thereby facilitating delivery of bone augmentation material into the bone, bones, or bone pieces via the cannulation 109.

In the third embodiment, the bridge 114 includes a transition section 129 disposed at the central axis 130 thereof. The regular inherent shape of the implant 105 according to the third embodiment, as illustrated in FIGS. 31-36, is its natural shape 106 where the transition section 129 locates the bridge 114 in a natural form consisting of a closed or angular profile whereby the first and second ends 119 and 120 reside at a first distance and the legs 121 and 122 reside in a natural position whereby the legs 121 and 122 are convergent and spaced apart at a first distance. Nevertheless, as illustrated in FIGS. 36-42, the implant 105 is deformable under the action of superelasticity or temperature dependent shape memory to its insertion shape 107 where the transition section 129 deforms to store energy while also moving the bridge 114 from its natural form to an insertion form which, in the third embodiment, is an open or substantially linear profile whereby the first and second ends 119 and 120 reside at a second distance that is greater than the first distance and the legs 121 and 122 reside in an insertion position whereby the legs 121 and 122 are substantially parallel and spaced apart at a second distance that is greater than the first distance. Since the insertion shape 107 is not the regular inherent shape of the implant 105, the transition section 129 typically is mechanically constrained or chilled until it reaches its martensite phase whereby the transition section 129 once deformed maintains the bridge 114 in its insertion form. After implantation into bone, bones, or bone pieces and a release of a mechanical constraint or a heating of the implant 105 to its austenite phase, the implant 105 delivers the energy stored in the transition section 129 such that the bridge 114 attempts to transition from its insertion form to its natural form, resulting in the legs 121 and 122 attempting to move from their insertion position to their natural position whereby the implant 105 affixes the bone, bones, or bone pieces through an application of a compressive force thereto.

While the transition section 129 of the bridge 114 has been described as moving to create compression, one of ordinary skill in the art will recognize that movement of the transition section 129 and attempted transition of the bridge 114 from its insertion form to its natural form may distract bone, bones, or bone pieces to hold the bone, bones, or bone pieces in an arrangement that promotes a healing thereof. In a distraction configuration, FIGS. 37-42 would illustrate an orthopedic implant 105 in a natural shape, whereas FIGS. 31-36 would illustrate the orthopedic implant 105 in an insertion shape. The transition section 129 for distraction locates the bridge 114 in a natural form consisting of an open or substantially linear profile whereby the first and second ends 119 and 120 reside at a first distance and the legs 121 and 122 reside in a natural position whereby the legs 121 and 122 are substantially parallel and spaced apart at a first distance. Nevertheless, the transition section 129 deforms to store energy while also moving the bridge 114 from its natural form to an insertion form which is a closed or angular profile whereby the first and second ends 119 and 120 reside at a second distance that is less than the first distance and the legs 121 and 122 reside in an insertion position whereby the legs 121 and 122 are convergent and spaced apart at a second distance that is less than the first distance. Upon implantation into bone, bones, or bone pieces and a release of a mechanical constraint or a heating of the implant 105 to its austenite phase, the implant 105 delivers the energy stored in the transition section 129 such that the bridge 114 attempts to transition from its insertion form to its natural form, resulting in the legs 121 and 122 attempting to move from their insertion position to their natural position whereby the implant 105 affixes the bone, bones, or bone pieces through an application of a distractive force thereto.

Figure 43:
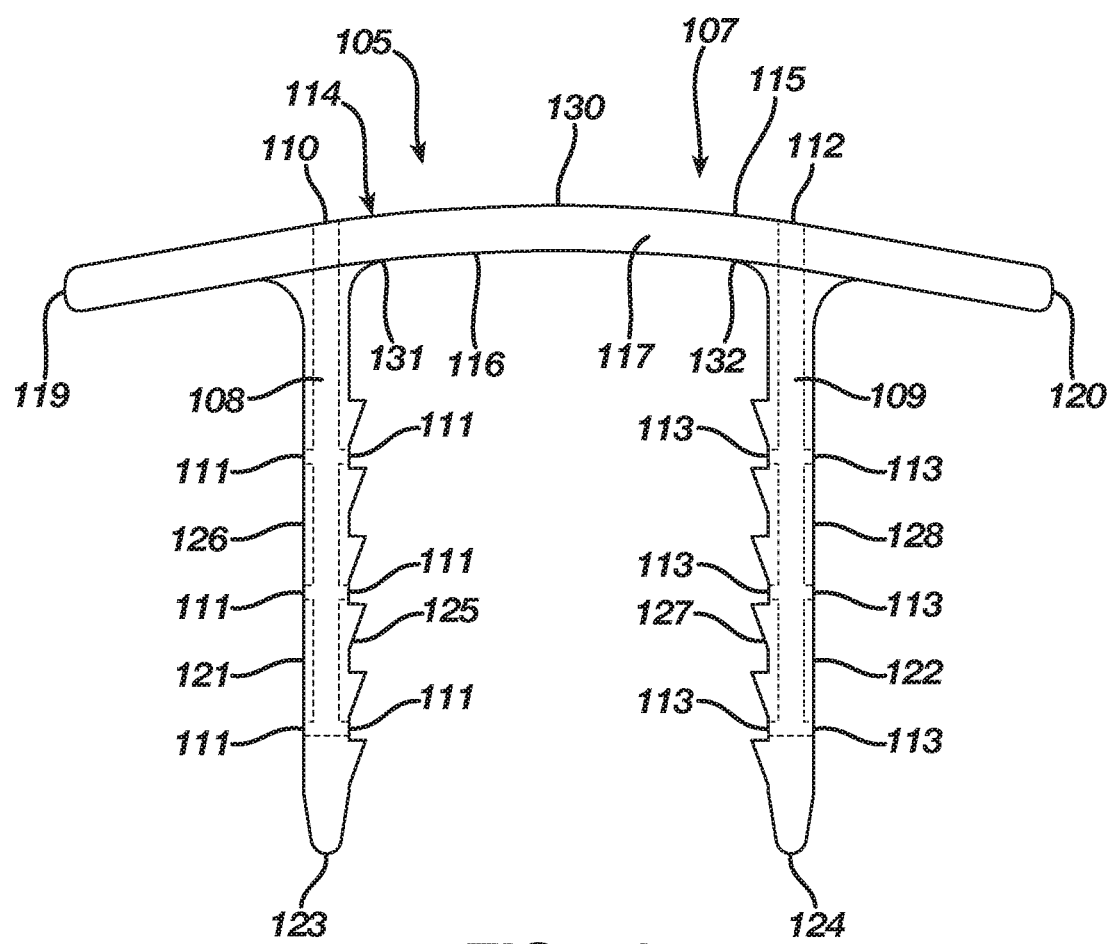
FIG. 43 is a side view of a shape memory implant according to an alternative of the third embodiment in an insertion shape.

Alternatively, the bridge 114 in the third embodiment may include transition sections 131 and 132 located respectively where the legs 121 and 122 extend from the bridge 114. The regular inherent shape of the implant 105, as illustrated in FIGS. 31-36, is its natural shape 106 where the transition sections 131 and 132 locate the bridge 114 in a natural form that places the legs 121 and 122 in a natural position whereby the legs 121 and 122 are convergent and spaced apart at a first distance. Nevertheless, as illustrated in FIG. 43, the implant 105 is deformable under the action of superelasticity or temperature dependent shape memory to an insertion shape 107 where the transition sections 131 and 132 deform to store energy while also moving the bridge 114 from its natural form to an insertion form that places the legs 121 and 122 in an insertion position whereby the legs 121 and 122 are substantially parallel and spaced apart at a second distance that is greater than the first distance. Since the insertion shape 107 is not the regular inherent shape of the implant 105, the transition sections 131 and 132 typically are mechanically constrained or chilled until they reach their martensite phase whereby the transition sections 131 and 132 once deformed maintain the bridge 114 in its insertion form. After implantation into bone, bones, or bone pieces and a release of a mechanical constraint or a heating of the implant 105 to its austenite phase, the implant 105 delivers the energy stored in the transition sections 131 and 132 such that the bridge 114 attempts to transition from its insertion form to its natural form, resulting in the legs 121 and 122 attempting to move from their insertion position to their natural position whereby the implant 105 affixes the bone, bones, or bone pieces through an application of a compressive force thereto.

While the transition sections 131 and 132 of the bridge 114 have been described as moving to create compression, one of ordinary skill in the art will recognize that movement of the transition sections 131 and 132 and attempted transition of the bridge 114 from its insertion form to its natural form may distract bone, bones, or bone pieces to hold the bone, bones, or bone pieces in an arrangement that promotes a healing thereof. In a distraction configuration, FIG. 43 would illustrate an orthopedic implant 105 in a natural shape, whereas FIGS. 31-36 would illustrate the orthopedic implant 105 in an insertion shape. The transition sections 131 and 132 for distraction locate the bridge 114 in a natural form that places the legs 121 and 122 in a natural position whereby the legs 121 and 122 are substantially parallel and spaced apart at a first distance. Nevertheless, the transition sections 131 and 132 deform to store energy while also moving the bridge 114 from its natural form to an insertion form that places the legs 121 and 122 in an insertion position whereby the legs 121 and 122 are convergent and spaced apart at a second distance that is less than the first distance. Upon implantation into bone, bones, or bone pieces and a release of a mechanical constraint or a heating of the implant 105 to its austenite phase, the implant 105 delivers the energy stored in the transition sections 131 and 132 such that the bridge 114 attempts to transition from its insertion form to its natural form, resulting in the legs 121 and 122 attempting to move from their insertion position to their natural position whereby the implant 105 affixes the bone, bones, or bone pieces through an application of a distractive force thereto.

Figure 44:
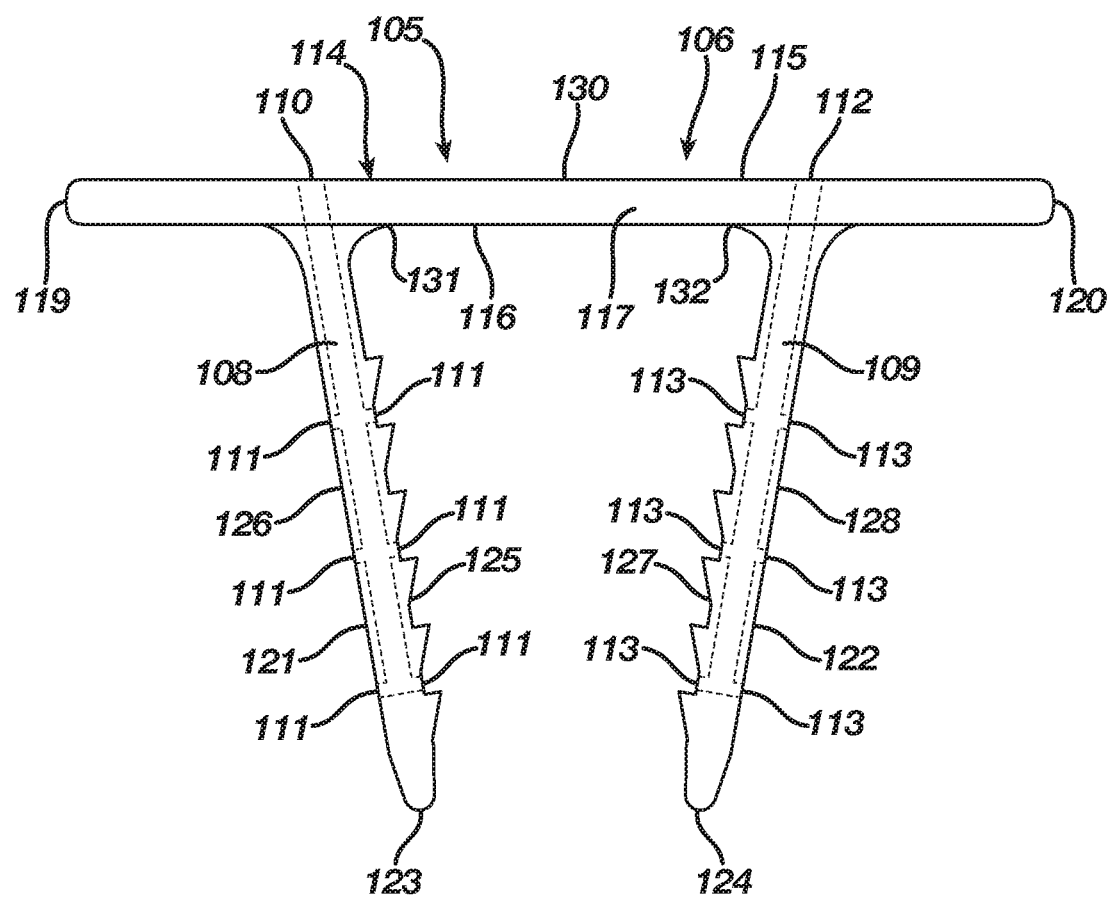
FIG. 44 is a side view of a shape memory implant according to an alternative of the third embodiment in a natural shape.
Figure 45:
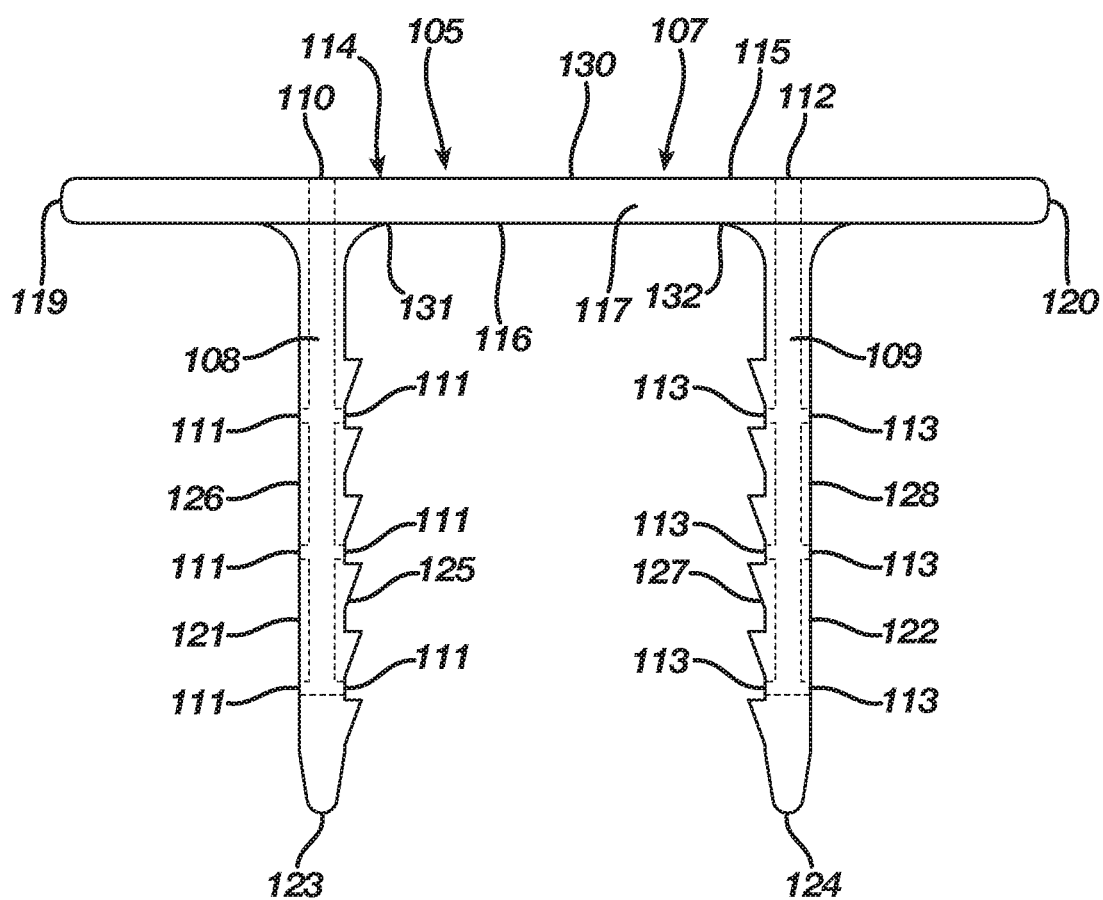
FIG. 45 is a side view of a shape memory implant according to an alternative of the third embodiment in an insertion shape.

Although the third embodiment of the implant 105 includes either the transition section 129 or the transition sections 131 and 132 to produce deformation thereof, one of ordinary skill in the art will recognize that the bridge 114 of the implant 105 may include both the transition section 129 and the transition sections 131 and 132 to produce deformation thereof. Moreover, while the bridge 114 in the third embodiment includes an angular profile in the natural shape of the implant 105, it should be understood by one of ordinary skill in the art that a bridge 114 incorporating the transition sections 131 and 132 may include a substantially linear profile for the natural shape of the implant 105. In particular, when the implant 105 exerts a compressive force to bone, bones, or bone pieces, the bridge 114, as illustrated in FIG. 44, includes a substantially linear profile in the natural shape of the implant 105. Furthermore, the bridge 114, as shown in FIG. 45, maintains its substantially linear profile once the implant 105 deforms to an insertion shape. Conversely, when the implant 105 exerts a distractive force to bone, bones, or bone pieces, FIG. 45 illustrates the implant 105 in a natural shape, whereas FIG. 44 illustrates the implant 105 in an insertion shape.

An implantation of the implant 105 into bone, bones, or bone pieces includes the bridge 114 and in particular a segment of the bridge 114 between the legs 121 and 122 spanning a fixation zone of the bone, bones, or bone pieces with the leg 121 inserting into the bone, bones, or bone pieces adjacent a first side of the fixation zone and the leg 122 inserting into the bone, bones, or bone pieces adjacent a second side of the fixation zone followed by an attempted transition of the implant 105 from its insertion shape 107 to its natural shape 106 and a corresponding delivery of energy to the bone, bones, or bone pieces at the fixation zone. In order to enhance implantation of the implant 105 into the bone, bones, or bone pieces including an ability of the implant 105 to overcome any implantation issues associated with bone, bones, or bone pieces of poorer quality, the implant 105 includes the cannulation 108 that traverses the bridge 114 and the leg 121 until exiting the leg 121 at the outlets 111 and the cannulation 109 that traverses the bridge 114 and the leg 122 until exiting the leg 122 at the outlets 113. During implantation of the implant 105, a bone augmentation material introduced into the cannulation 108 via its inlet 110 traverses the cannulation 108 and then exits the cannulation 108 at its outlets 111 such that the bone augmentation material enters the bone, bones, or bone pieces around the leg 121 and its tip 123. Likewise, a bone augmentation material introduced into the cannulation 109 via its inlet 112 traverses the cannulation 109 and then exits the cannulation 109 at its outlets 113 such that the bone augmentation material enters the bone, bones, or bone pieces around the leg 122 and its tip 124. The bone augmentation material fills the bone, bones, or bone pieces around the legs 121 and 122, and, once its sets or cures, the bone augmentation material enhances the structural integrity of the bone, bones, or bone pieces whereby the bone, bones, or bone pieces receive energy imparted thereto from the implant 105 without experiencing a structural failure that causes a loss of fixation and subsequent improper fusion or distraction thereof. The bone augmentation material accordingly augments the bone, bones, or bone pieces resulting in the bone, bones, or bone pieces arresting movement of the legs 121 and 122 from their insertion position to their natural position during an attempted transition of the bridge 114 from its insertion form to its natural form such that the implant 105 imparts a force sufficient to fuse or distract the bone, bones, or bone pieces.

After implantation of the implant 105 into bone, bones, or bone pieces, the fixation device 137 passes through the aperture 135 of the bridge 114 while also remaining engaged therewith and further inserts into the bone, bones, or bone pieces in order to assist in securing the implant 105 with the bone, bones, or bone pieces at the end 119 of the bridge 114. Similarly, the fixation device 138 passes through the aperture 136 of the bridge 114 while also remaining engaged therewith and further inserts into the bone, bones, or bone pieces in order to assist in securing the implant 105 with the bone, bones, or bone pieces at the end 120 of the bridge 114. When the fixation devices 137 and 138 include respective cannulations 139 and 140, a bone augmentation material introduced into the bone, bones, or bone pieces via the cannulations 139 and 140 fills the bone, bones, or bone pieces, and, once its sets or cures, the bone augmentation material augments the structural integrity of the bone, bones, or bone pieces in order to enhance the ability of the bone, bones, or bone pieces to retain the implant 105 therein.

Figure 46:
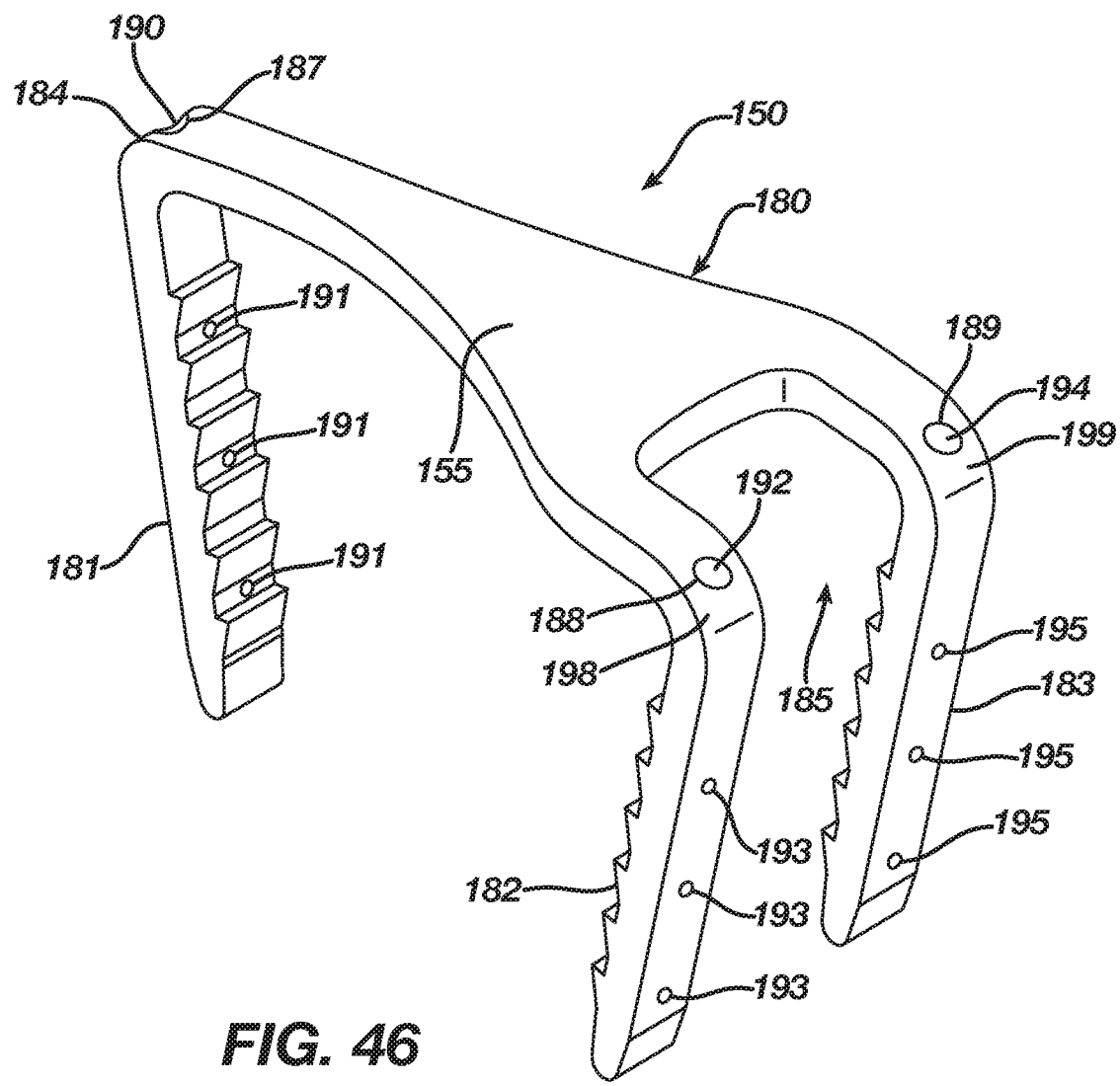
FIG. 46 is an isometric view illustrating a shape memory implant according to a fourth embodiment in a natural shape.
Figure 47:
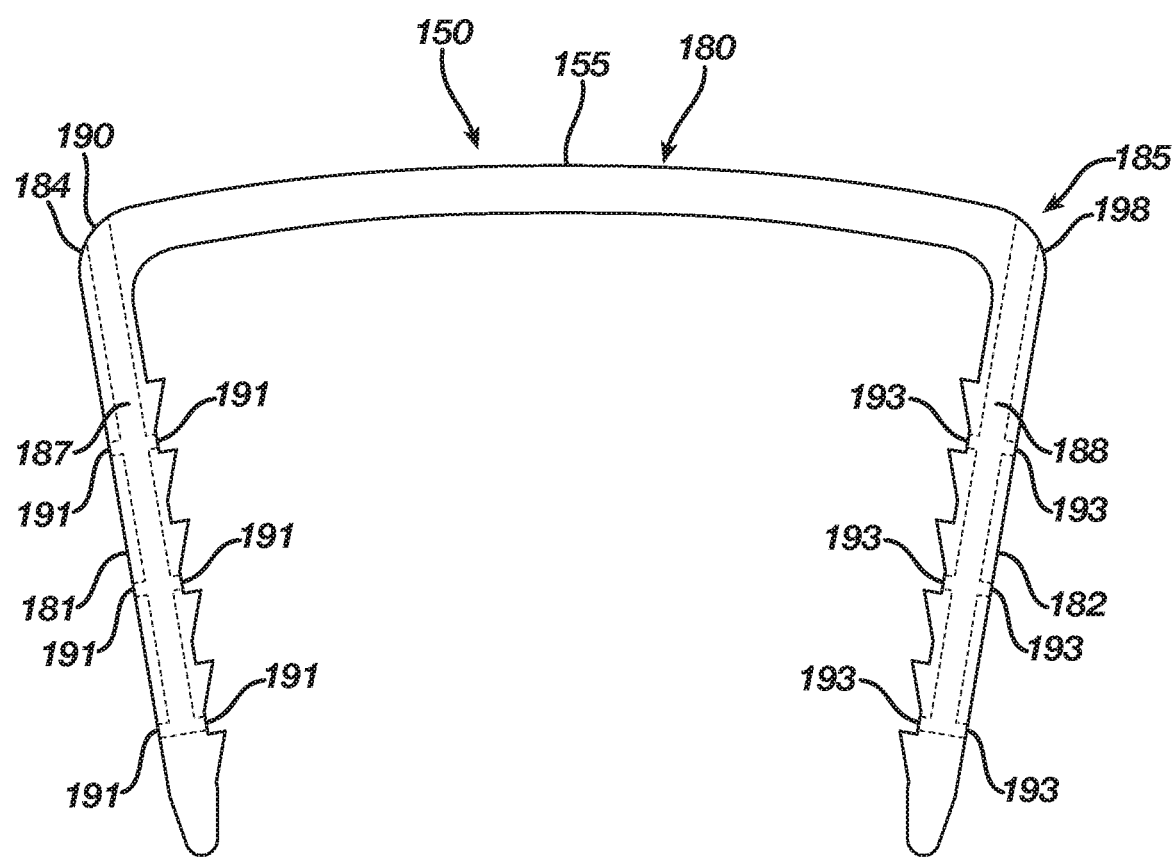
FIG. 47 is a side view thereof.

FIGS. 46 and 47 illustrate an orthopedic implant 150 according to a fourth embodiment in a natural shape. The implant 150 includes the natural shape and also an insertion shape. The implant 150 in the fourth embodiment may be manufactured from a shape memory material with superelastic or temperature dependent properties (e.g., Nitinol) such that the implant 150 transitions between its natural shape and its insertion shape. The implant 150 when deformed from its natural shape to its insertion shape stores energy deliverable to bone, bones, or bone pieces. In accordance with its manufacture from shape memory material, the implant 150 begins in its natural shape, is transitionable to its insertion shape, and, once implanted in bone, bones, or bone pieces, attempts to transition from its insertion shape to its natural shape whereby the implant 150 delivers the energy stored therein to the bone, bones, or bone pieces in order to affix the bone, bones, or bone pieces and promote a healing thereof. In the fourth embodiment, attempted transition of the implant 150 from its insertion shape to its natural shape continuously compresses the bone, bones, or bone pieces to promote fusion thereof. Nevertheless, one of ordinary skill in the art will recognize that the attempted transition of the implant 150 from its insertion shape to its natural shape may distract the bone, bones, or bone pieces to hold the bone, bones, or bone pieces in an arrangement that promotes a healing thereof. In a distraction configuration, FIGS. 46 and 47 would illustrate the orthopedic implant 150 in an insertion shape.

The implant 150 in the fourth embodiment includes a shape that differs from the implant 5 of the first embodiment in order to expand bone fixation surgeries performable using an implant according to the present invention. Nevertheless, the design concept and principle of operation for the implant 150 in the fourth embodiment is substantially identical to that of the implant 5 according to the first embodiment.

The implant 150 in the fourth embodiment includes a bridge 180 that differs in shape from the bridge 14 of the implant 5 and anchoring members in the form of legs 181-183 that differ in number from the legs 21 and 22 of the implant 5. The bridge 180 in the fourth embodiment is three-dimensional in form having a length, width, and height, and, in particular, the bridge 180 is plate-shaped with a Y configuration including an end 184 and an end 185 comprised of discrete ends 198 and 199. The leg 181 extends from a lower surface of the bridge 180 at its end 184, the leg 182 extends from the lower surface of the bridge 180 at its end 198, and the leg 183 extends from the lower surface of the bridge 180 at its end 199.

The implant 150 includes a cannulation 187 that originates in the bridge 180 with an inlet 190 in the bridge 180 at the leg 181 adjacent the end 184 of the bridge 180. The cannulation 187 traverses the bridge 180 and then the leg 181 until the cannulation 187 exits the leg 181 in one or more outlets 191 located at any point along the leg 181 including at a tip of the leg 181 such that the one or more outlets 191 deliver a bone augmentation material around the leg 181.

The implant 150 includes a cannulation 188 that originates in the bridge 180 with an inlet 192 in the bridge 180 at the leg 182 adjacent the end 198 of the bridge 180. The cannulation 188 traverses the bridge 180 and then the leg 182 until the cannulation 188 exits the leg 182 in one or more outlets 192 located at any point along the leg 182 including at a tip of the leg 182 such that the one or more outlets 192 deliver a bone augmentation material around the leg 182.

The implant 150 includes a cannulation 189 that originates in the bridge 180 with an inlet 194 in the bridge 180 at the leg 183 adjacent the end 199 of the bridge 180. The cannulation 189 traverses the bridge 180 and then the leg 183 until the cannulation 189 exits the leg 183 in one or more outlets 194 located at any point along the leg 183 including at a tip of the leg 183 such that the one or more outlets 194 deliver a bone augmentation material around the leg 183.

Although the bridge 180 of the implant 150 differs in shape from the bridge 14 of the implant 5 and includes three legs 181-183, the bridge 180 is substantially identical to the bridge 14 in that the bridge 180 includes a transition section 155 that locates the bridge 180 in a natural form. Nevertheless, the implant 150 is deformable under the action of superelasticity or temperature dependent shape memory from its natural shape to its insertion shape where the transition section 155 deforms to store energy while also moving the bridge 180 from its natural form to an insertion form. After implantation of the implant 150 into bone, bones, or bone pieces, the bridge 180 attempts to transition from its insertion form to its natural form whereby the bridge 180 delivers the energy stored therein such that the implant 150 affixes the bone, bones, or bone pieces through either a compression or a distraction thereof. Alternatively, or in combination, the bridge 180 may include transition sections located respectively where the legs 181-183 extend from the bridge 180.

An implantation of the implant 150 into bone, bones, or bone pieces includes the bridge 180 spanning a fixation zone of the bone, bones, or bone pieces with the leg 181 inserting into the bone, bones, or bone pieces adjacent a first side of the fixation zone and the legs 182 and 183 inserting into the bone, bones, or bone pieces adjacent a second side of the fixation zone followed by an attempted transition of the implant 150 from its insertion shape to its natural shape and a corresponding delivery of energy to the bone, bones, or bone pieces at the fixation zone. In order to enhance implantation of the implant 150 into the bone, bones, or bone pieces including an ability of the implant 150 to overcome any implantation issues associated with bone, bones, or bone pieces of poorer quality, the implant 150 includes the cannulations 187-189 that traverse the bridge 180 and respective legs 181-183 until exiting the respective legs 181-183 at respective outlets 191, 193, and 195. During implantation of the implant 150, a bone augmentation material introduced into the cannulations 187-189 via their respective inlet 190, 192, and 194 traverses the cannulations 187-189 and then exits the cannulations 187-189 at their respective outlets 191, 193, and 195 such that the bone augmentation material enters the bone, bones, or bone pieces around the legs 181-183 and their tips. The bone augmentation material fills the bone, bones, or bone pieces around the legs 181-183, and, once its sets or cures, the bone augmentation material enhances the structural integrity of the bone, bones, or bone pieces whereby the bone, bones, or bone pieces receive energy imparted thereto from the implant 150 without experiencing a structural failure that causes a loss of fixation and subsequent improper fusion or distraction thereof. The bone augmentation material accordingly augments the bone, bones, or bone pieces resulting in the bone, bones, or bone pieces arresting movement of the legs 181-183 during an attempted transition of the bridge 180 from its insertion form to its natural form such that the implant 150 imparts a force sufficient to fuse or distract the bone, bones, or bone pieces.

The body 280 in the second alternative embodiment is three-dimensional in form having a length, width, and height, and, in particular, the body 280 is plate-shaped with an X configuration including a first end 285 and a second end 286 comprised of discrete ends 287-290.

Figure 48:
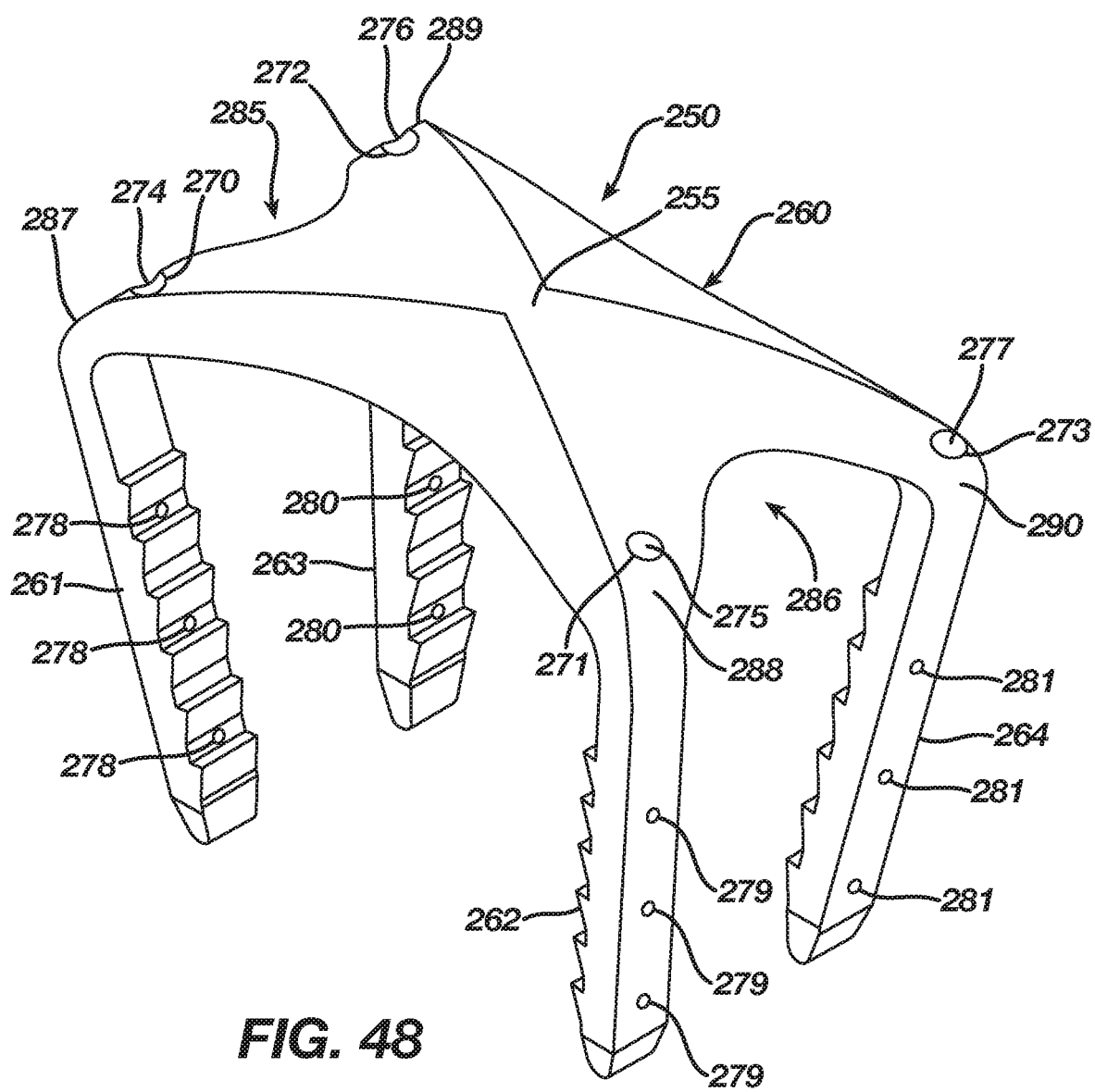
FIG. 48 is an isometric view illustrating a shape memory implant according to a fifth embodiment in a natural shape.
Figure 49:
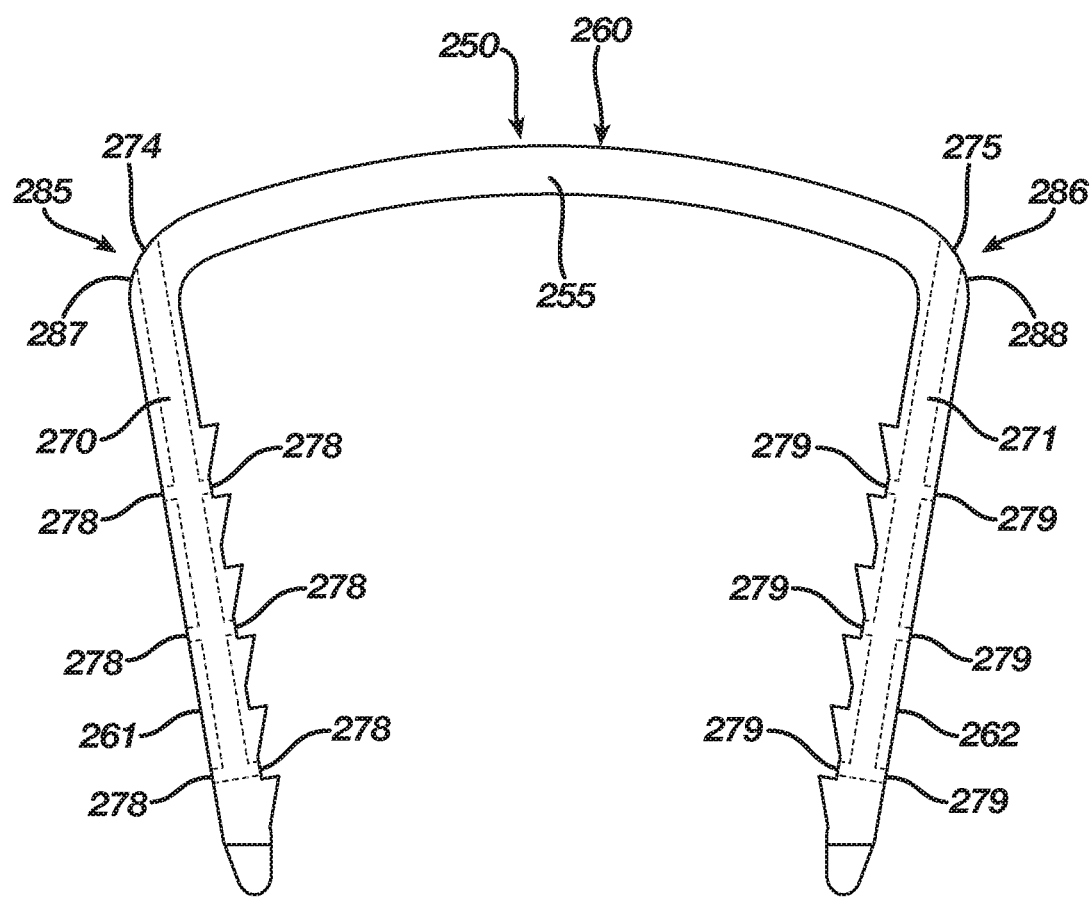
FIG. 49 is a side view thereof.

FIGS. 48 and 49 illustrate an orthopedic implant 250 according to a fifth embodiment in a natural shape. The implant 250 includes the natural shape and also an insertion shape. The implant 250 in the fifth embodiment may be manufactured from a shape memory material with superelastic or temperature dependent properties (e.g., Nitinol) such that the implant 250 transitions between its natural shape and its insertion shape. The implant 250 when deformed from its natural shape to its insertion shape stores energy deliverable to bone, bones, or bone pieces. In accordance with its manufacture from shape memory material, the implant 250 begins in its natural shape, is transitionable to its insertion shape, and, once implanted in bone, bones, or bone pieces, attempts to transition from its insertion shape to its natural shape whereby the implant 250 delivers the energy stored therein to the bone, bones, or bone pieces in order to affix the bone, bones, or bone pieces and promote a healing thereof. In the fifth embodiment, attempted transition of the implant 250 from its insertion shape to its natural shape continuously compresses the bone, bones, or bone pieces to promote fusion thereof. Nevertheless, one of ordinary skill in the art will recognize that the attempted transition of the implant 250 from its insertion shape to its natural shape may distract the bone, bones, or bone pieces to hold the bone, bones, or bone pieces in an arrangement that promotes a healing thereof. In a distraction configuration, FIGS. 48 and 49 would illustrate the orthopedic implant 250 in an insertion shape.

The implant 150 in the fifth embodiment includes a shape that differs from the implant 5 of the first embodiment in order to expand bone fixation surgeries performable using an implant according to the present invention. Nevertheless, the design concept and principle of operation for the implant 250 in the fifth embodiment is substantially identical to that of the implant 5 according to the first embodiment.

The implant 250 in the fifth embodiment includes a bridge 260 that differs in shape from the bridge 14 of the implant 5 and anchoring members in the form of legs 261-264 that differ in number from the legs 21 and 22 of the implant 5. The bridge 260 in the fifth embodiment is three-dimensional in form having a length, width, and height, and, in particular, the bridge 260 is plate-shaped with an X configuration including an end 285 comprised of discrete ends 287 and 289 and an end 286 comprised of discrete ends 288 and 290. The leg 261 extends from a lower surface of the bridge 260 at its end 285 and in particular at its discrete end 287, the leg 262 extends from a lower surface of the bridge 260 at its end 286 and in particular at its discrete end 288, and the leg 263 extends from a lower surface of the bridge 260 at its end 285 and in particular at its discrete end 289, and the leg 264 extends from a lower surface of the bridge 260 at its end 286 and in particular at its discrete end 290

The implant 250 includes a cannulation 270 that originates in the bridge 260 with an inlet 274 in the bridge 260 at the leg 261 adjacent the discrete end 287 of the bridge 260. The cannulation 270 traverses the bridge 260 and then the leg 261 until the cannulation 270 exits the leg 261 in one or more outlets 278 located at any point along the leg 261 including at a tip of the leg 261 such that the one or more outlets 278 deliver a bone augmentation material around the leg 261.

The implant 250 includes a cannulation 271 that originates in the bridge 260 with an inlet 275 in the bridge 260 at the leg 262 adjacent the discrete end 288 of the bridge 260. The cannulation 271 traverses the bridge 260 and then the leg 262 until the cannulation 271 exits the leg 262 in one or more outlets 279 located at any point along the leg 262 including at a tip of the leg 262 such that the one or more outlets 275 deliver a bone augmentation material around the leg 262.

The implant 250 includes a cannulation 272 that originates in the bridge 260 with an inlet 276 in the bridge 260 at the leg 263 adjacent the discrete end 289 of the bridge 260. The cannulation 272 traverses the bridge 260 and then the leg 263 until the cannulation 272 exits the leg 263 in one or more outlets 276 located at any point along the leg 263 including at a tip of the leg 263 such that the one or more outlets 276 deliver a bone augmentation material around the leg 263.

The implant 250 includes a cannulation 273 that originates in the bridge 260 with an inlet 277 in the bridge 260 at the leg 264 adjacent the discrete end 290 of the bridge 260. The cannulation 273 traverses the bridge 260 and then the leg 264 until the cannulation 273 exits the leg 264 in one or more outlets 277 located at any point along the leg 264 including at a tip of the leg 264 such that the one or more outlets 277 deliver a bone augmentation material around the leg 264.

Although the bridge 260 of the implant 250 differs in shape from the bridge 14 of the implant 5 and includes four legs 261-264, the bridge 260 is substantially identical to the bridge 14 in that the bridge 260 includes a transition section 255 that locates the bridge 260 in a natural form. Nevertheless, the implant 250 is deformable under the action of superelasticity or temperature dependent shape memory from its natural shape to its insertion shape where the transition section 255 deforms to store energy while also moving the bridge 260 from its natural form to an insertion form. After implantation of the implant 250 into bone, bones, or bone pieces, the bridge 260 attempts to transition from its insertion form to its natural form whereby the bridge 260 delivers the energy stored therein such that the implant 250 affixes the bone, bones, or bone pieces through either a compression or a distraction thereof. Alternatively, or in combination, the bridge 260 may include transition sections located respectively where the legs 261-264 extend from the bridge 260.

An implantation of the implant 250 into bone, bones, or bone pieces includes the bridge 260 spanning a fixation zone of the bone, bones, or bone pieces with the legs 261 and 263 inserting into the bone, bones, or bone pieces adjacent a first side of the fixation zone and the legs 262 and 264 inserting into the bone, bones, or bone pieces adjacent a second side of the fixation zone followed by an attempted transition of the implant 250 from its insertion shape to its natural shape and a corresponding delivery of energy to the bone, bones, or bone pieces at the fixation zone. In order to enhance implantation of the implant 250 into the bone, bones, or bone pieces including an ability of the implant 250 to overcome any implantation issues associated with bone, bones, or bone pieces of poorer quality, the implant 250 includes the cannulations 270-273 that traverse the bridge 260 and respective legs 261-264 until exiting the respective legs 261-264 at respective outlets 278-281. During implantation of the implant 250, a bone augmentation material introduced into the cannulations 270-273 via their respective inlet 274-277 traverses the cannulations 270-273 and then exits the cannulations 270-273 at their respective outlets 278-281 such that the bone augmentation material enters the bone, bones, or bone pieces around the legs 261-264 and their tips. The bone augmentation material fills the bone, bones, or bone pieces around the legs 261-264, and, once its sets or cures, the bone augmentation material enhances the structural integrity of the bone, bones, or bone pieces whereby the bone, bones, or bone pieces receive energy imparted thereto from the implant 250 without experiencing a structural failure that causes a loss of fixation and subsequent improper fusion or distraction thereof. The bone augmentation material accordingly augments the bone, bones, or bone pieces resulting in the bone, bones, or bone pieces arresting movement of the legs 261-264 during an attempted transition of the bridge 260 from its insertion form to its natural form such that the implant 250 imparts a force sufficient to fuse or distract the bone, bones, or bone pieces.

Figure 50:
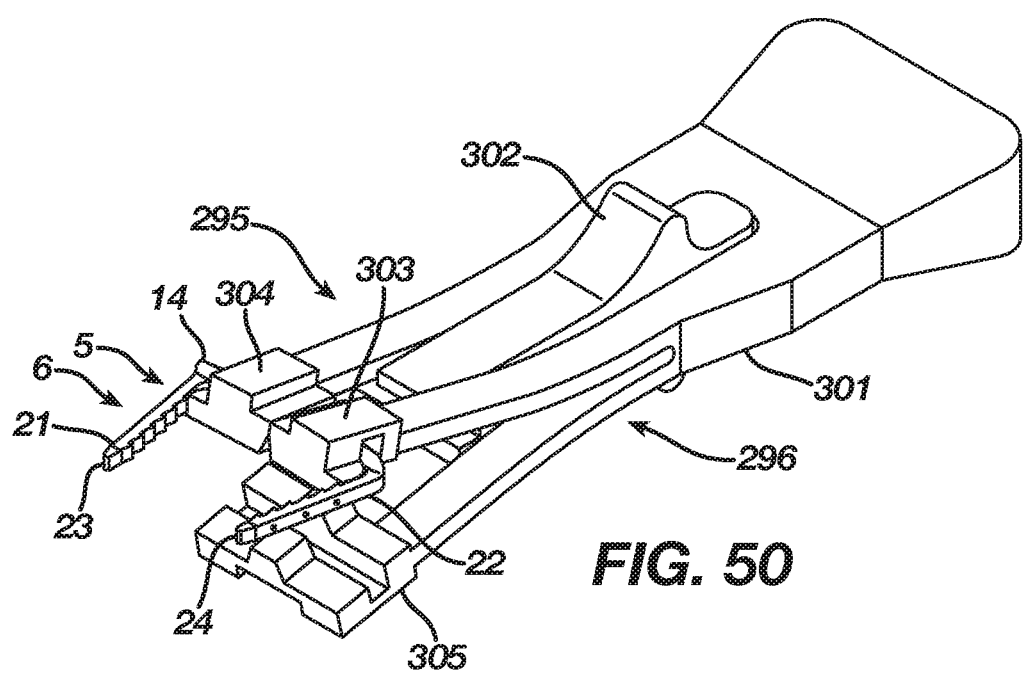
FIG. 50 is an isometric view illustrating an example implant insertion device prior to its loading with a shape memory implant according to the first embodiment.
Figure 51:
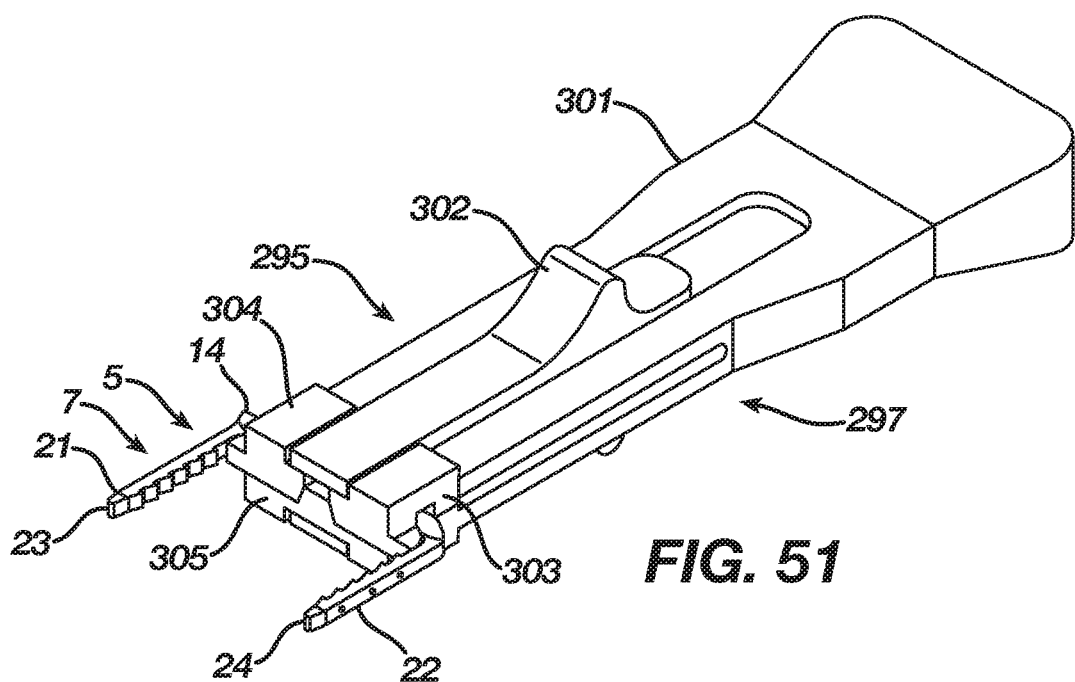
FIG. 51 is an isometric view illustrating the example implant insertion device loaded with a shape memory implant according to the first embodiment.

FIGS. 50 and 51 illustrate an implant insertion device 295 that engages the implant 5 and maintains the implant 5 in its insertion shape 7. FIG. 50 illustrates the implant insertion device 295 prior to its loading with the implant 5, whereas FIG. 51 illustrates the implant insertion device 295 loaded with the implant 5. Implant insertion devices suitable to maintain the implant 5 in its insertion shape 7, such as the exemplary implant insertion device 295, are available from DePuy Synthes Products, Inc., 325 Paramount Drive, Rayham, Mass. 02767. The implant insertion device 295 is presented herein as an example of a type of mechanical constraint that may be used with the implants of the present invention, nevertheless, one of ordinary skill in the art will recognize that any implant insertion device suitable to hold an implant of the present invention for use in a compression or distraction of bone, bones, or bone pieces may be utilized.

The implant insertion device 295 resides in either an implant disengagement position 296 as illustrated in FIG. 50 or an implant engagement position 297 as illustrated in FIG. 51 and is movable therebetween. In the implant disengagement position 296, the implant 5 slips into or out of the implant insertion device 295 with no obstruction. In the implant engagement position 297, the implant insertion device 295 engages the implant 5 and maintains the implant 5 in its insertion shape 7. In addition, the implant insertion device 295 allows a surgeon to manipulate the implant 5 and insert the implant 5 into bone, bones, or bone pieces that require fixating.

The implant insertion device 295 includes a body 301 and a slider 302. The body 301 is configured to accept the slider 302 such that the slider 302 moves along the body 301 between an unlocked and a locked position. The body 301 includes a handle and first, second, third, and fourth arms extending from the handle. The handle allows manipulation of the implant insertion device 295 and delivery of the implant 5 into bone, bones, or bone pieces. The first arm terminates in a first jaw 303 configured to engage the implant 5. Likewise, the second arm terminates in a second jaw 304 configured to engage the implant 5. The third and fourth arms collectively terminate in a third jaw 305 configured to engage the implant 5. The jaws 303-305 move between a disengaged position that releases the implant 5 and an engaged position whereby the jaws 303-305 engage the implant 5 and maintain the implant 5 in its insertion shape 7. The jaws 303-305 are configured to accept the slider 302 such that, when the slider 302 resides in its locked position, the slider 302 holds the jaws 303-305 in their engaged position. Conversely, when the slider 302 resides in its unlocked position, the slider 302 releases the jaws 303-305 such that the jaws 303-305 move to their disengaged position.

In a first method of receiving the implant 5, the implant insertion device 295 begins in its implant disengagement position 296 wherein the jaws 303-305 reside in their disengaged position. The implant 5 is mechanically deformed from its natural shape 6 to its insertion shape 7 such that the implant 5 stores mechanical energy. Once deformed, the implant 5 inserts within the jaws 303 and 304; in particular, the bridge 14 inserts within the jaws 303 and 304. After insertion of the implant 5, the jaws 303-305 are moved from their disengaged position to their engaged position, which entails movement of the jaws 303 and 304 downward and the jaw 305 upward until the jaws 303 and 304 abut the jaw 305. Abutting the jaws 303 and 304 with the jaw 305 results in the jaw 305 receiving therein the implant 5 and, in particular, the bridge 14 such that the jaws 303-305 engage the bridge 14 thereby maintaining the implant 5 in its insertion shape 7. Abutting the jaws 303 and 304 with the jaw 305 further results in the jaw 305 urging the jaws 303 and 304 to engage the implant 5 and, in particular, the legs 21 and 22 such that the jaws 303 and 304 contact the legs 21 and 22 thereby maintaining the implant 5 in its insertion shape 7. With the jaws 303-305 now moved to their engaged position, the slider 302 is progressed from its unlocked to its locked position where the slider 302 holds the jaws 304-305 in their engaged position thereby clamping the implant 5 between the jaws 303-305 such that implant 5 remains loaded on the implant insertion device 295 in its insertion shape 7 with mechanical energy stored therein.

While the implant 5 may be mechanically deformed from its natural shape 6 to its insertion shape 7 before loading on the implant insertion device 295, in a second method, the implant 5 may be loaded on the implant insertion device 295 in its natural shape 6 and then mechanically deformed to its insertion shape 7 by the implant insertion device 295. The implant 5 inserts in its natural shape 6 within the jaws 303 and 304; in particular, the bridge 14 inserts within the jaws 303 and 304. After insertion of the implant 5, the jaws 303-305 are moved from their disengaged position to their engaged position, which entails movement of the jaws 303 and 304 downward and the jaw 305 upward until the jaws 303 and 304 abut the jaw 305. Abutting the jaws 303 and 304 with the jaw 305 results in the jaw 305 receiving therein the implant 5 and, in particular, the bridge 14 such that the jaws 303-305 engage the bridge 14 whereby the jaws 303-305 impart a force to the implant 5 such that the implant 5 mechanically deforms from its natural shape 6 to its insertion shape 7 further whereby the jaws 303-305 maintain the implant 5 in its insertion shape 7. Abutting the jaws 303 and 304 with the jaw 305 further results in the jaw 305 urging the jaws 303 and 304 to engage the implant 5 and, in particular, the legs 21 and 22 such that the jaws 303 and 304 contact the legs 21 and 22 whereby the jaws 303 and 304 impart a force to the implant 5 such that the implant 5 mechanically deforms from its natural shape 6 to its insertion shape 7 further whereby the jaws 303 and 304 maintain the implant 5 in its insertion shape 7. With the jaws 303-305 now moved to their engaged position, the slider 302 is progressed from its unlocked to its locked position where the slider 302 holds the jaws 304-305 in their engaged position thereby clamping the implant 5 between the jaws 303-305 such that implant 5 remains loaded on the implant insertion device 295 in its insertion shape 7 with mechanical energy stored therein. Although not necessary, the implant 5 may be cooled prior to loading on the implant insertion device 295 in order to place it in a martensitic state and aid in movement of the implant 5 from its natural shape 6 to its insertion shape 7.

The implant insertion device 295 and its loading with the implant 5 has been shown in order to provide an example mechanical constraint. Nevertheless, one of ordinary skill in the art will recognize that any mechanical device, such as forceps, suitable to engage the implant 5 and maintain the implant 5 in its insertion shape 7 may be employed.

Figure 52:
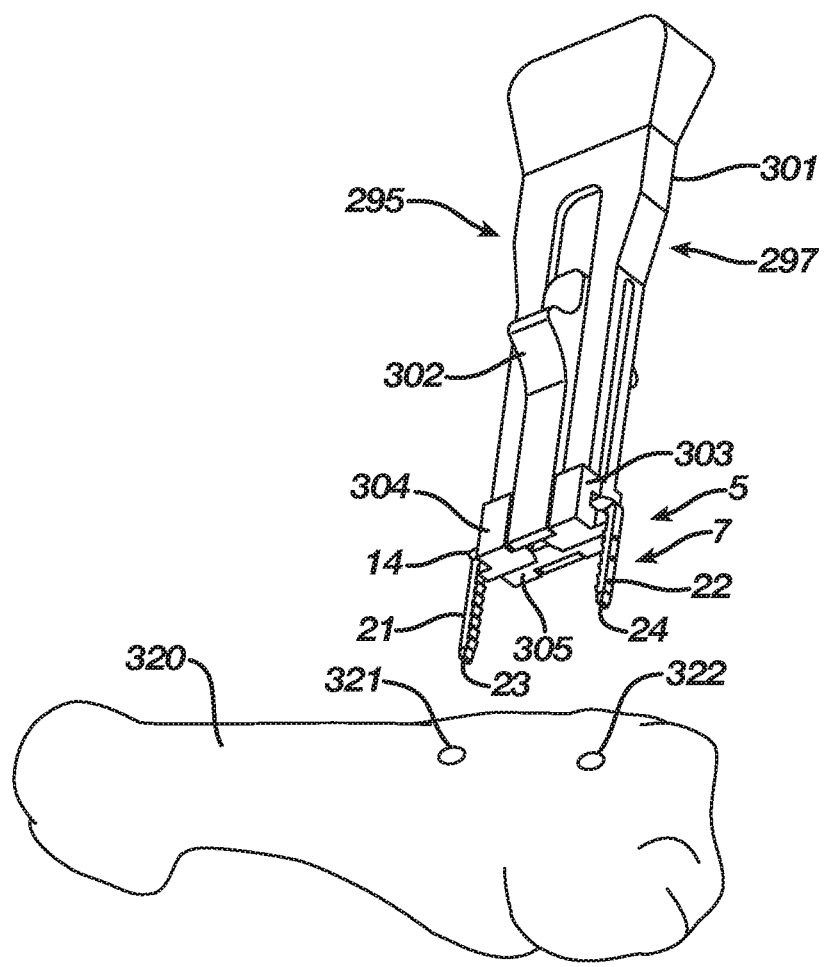
FIGS. 52-54 are isometric views illustrating insertion of a shape memory implant according to the first embodiment into bone, bones, or bone pieces.

FIG. 52 illustrates the implant insertion device 295 with the implant 5 loaded thereon whereby the implant insertion device 295 retains the implant 5 in its insertion shape 7 such that the implant 5 is ready for implantation into bone, bones, or bone pieces, and, in particular, into a bone 320 which is presented herein as an example. A surgeon aligns the bone 320 and then drills holes 321 and 322 therein at a desired location and spacing for insertion of the legs 21 and 22 into the bone 320 when the implant 5 resides in its insertion shape 7. The surgeon next utilizes the implant insertion device 295 to position the tips 23 and 24 of the legs 21 and 22 at the pre-drilled holes 321 and 322 and then insert the legs 21 and 22 into the bone 320 via the pre-drilled holes 321 and 322. Alternatively, the surgeon may align the bone 320 followed by the use of the implant insertion device 295 to impact the legs 21 and 22 into the bone 320 at a desired location.

Once the implant 5 inserts into the bone 320, the implant 5 is ready for removal from the implant insertion device 295. However, either prior to the insertion of the implant 5 into the bone 320 or prior to the removal of the implant 5 from the implant insertion device 295 after its insertion into the bone 320, a bone augmentation material delivery device 325, such as a syringe or the like, is filled with a bone augmentation material 326, such as bone cement. With the bone augmentation material delivery device 325 prepared to supply the bone augmentation material 326, the implant 5 is removed from the implant insertion device 295. To remove the implant 5 from the implant insertion device 295, the surgeon progresses the slider 302 from its locked position to its unlocked position resulting in the slider 302 releasing the jaws 303-305. The released jaws 303-305 travel from their engaged position to their disengaged position such that the implant insertion device 295 transitions from its implant engagement position 297 to its implant disengagement position 296 whereby the implant 5 disengages from the implant insertion device 295 without obstruction. In particular, the jaws 303 and 304 move away from the jaw 305 until the jaws 303 and 304 no longer abut the jaw 305. As a consequence, the jaws 303-305 release the implant 5 thereby allowing the surgeon to remove the implant insertion device 295 from the implant 5 thereby leaving the implant 5 within the bone 320.

After disengaging the implant insertion device 295 from the implant 5, the surgeon tamps the implant 5 in abutting relationship with bone 320.

Figure 53:
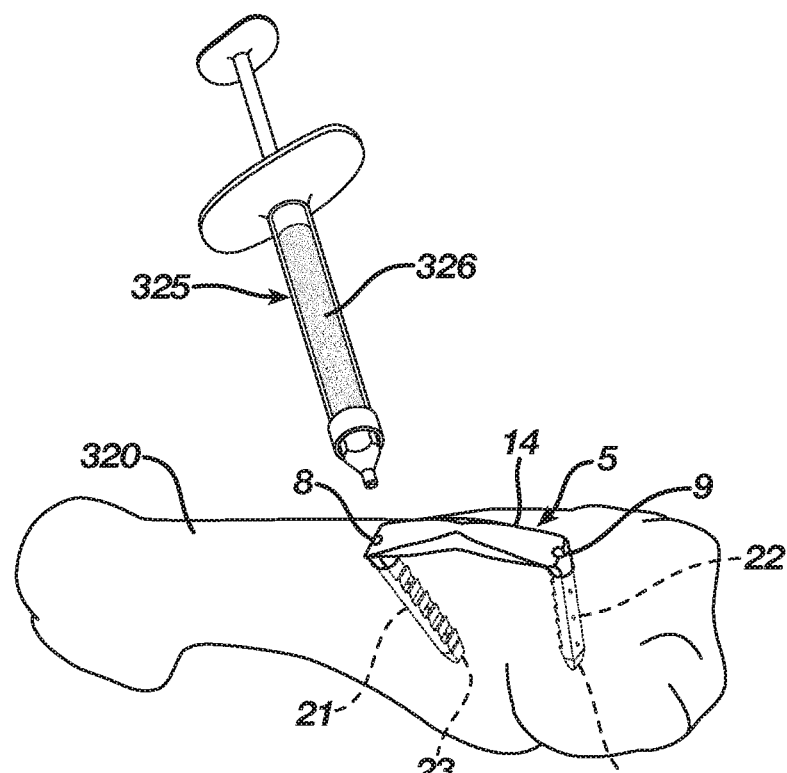
Figure 54:
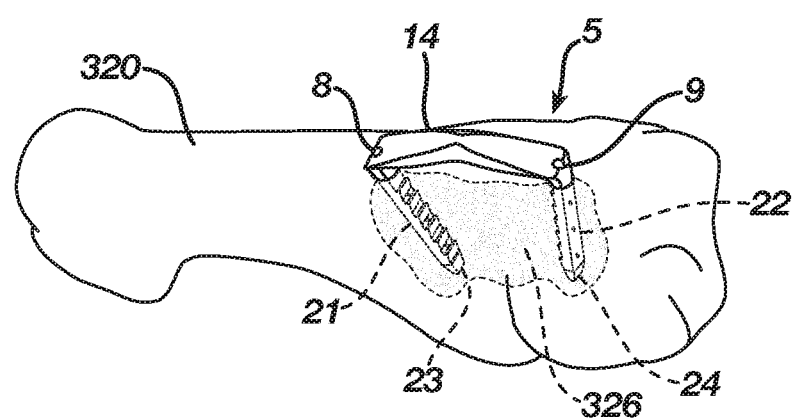

Upon the release of the implant 5 from the implant insertion device 295, the surgeon as illustrated in FIG. 53 employs the bone augmentation material delivery device 325 to convey the bone augmentation material 326 into the bone 320. The surgeon aligns an outlet of the bone augmentation material delivery device 325 with the cannulation 8 of the implant 5 and then actuates the bone augmentation material delivery device 325 to deliver the bone augmentation material 326 into the bone 320 via the cannulation 8. The bone augmentation material 326 enters the cannulation 8 via its inlet 10, traverses the cannulation 8, and then exits the cannulation 8 at its outlets 11 such that the bone augmentation material 326 enters the bone 320 pieces around the leg 21 and its tip 23. The surgeon aligns the outlet of the bone augmentation material delivery device 325 with the cannulation 9 of the implant 5 and then actuates the bone augmentation material delivery device 325 to deliver the bone augmentation material 326 into the bone 320 via the cannulation 9. The bone augmentation material 326 enters the cannulation 9 via its inlet 12, traverses the cannulation 9, and then exits the cannulation 9 at its outlets 11 such that the bone augmentation material 326 enters the bone 320 pieces around the leg 22 and its tip 24. The bone augmentation material 326 as illustrated in FIG. 54 fills the bone 320 around the legs 21 and 22, and, once its sets or cures, the bone augmentation material 326 enhances the structural integrity of the bone 320.

With the implant 5 released from the implant insertion device 295 and inserted into the bone 320, the implant 5 attempts to transition from its insertion shape 7 to its natural shape 6 such that the implant 5 through its compression or distraction of the bone 320 remains implanted in the bone 320 thereby holding the bone 320 in a desired alignment and assisting in the fixation and healing thereof. In particular, the bridge 14 attempts to transition from its insertion form to its natural form while the legs 21 and 22 attempt to move from their insertion position to their natural position. The bone 320 due to its augmentation with the bone augmentation material 326 and corresponding increased structural integrity receives energy imparted thereto from the implant 5 without experiencing a structural failure that causes a loss of fixation and subsequent improper fusion or distraction thereof. The bone augmentation material accordingly augments the bone 320 resulting in the bone 320 arresting movement of the legs 21 and 22 from their insertion position to their natural position during an attempted transition of the bridge 14 from its insertion form to its natural form such that the implant 5 imparts a force sufficient to fuse or distract the bone 320.

Figure 55:
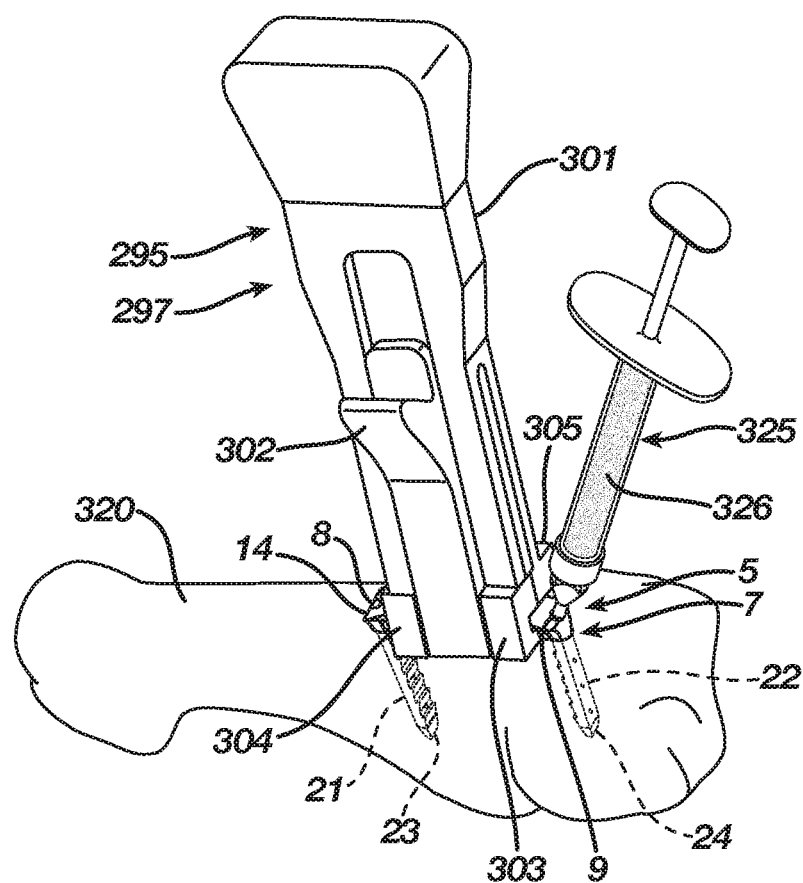
FIG. 55 is an isometric view illustrating an alternative insertion of a shape memory implant according to the first embodiment into bone, bones, or bone pieces.

FIG. 55 illustrates an alternative delivery of the bone augmentation material 326 into the bone 320 employing the bone augmentation material delivery device 325, which is filled with the bone augmentation material 326 prior to the insertion of the implant 5 into the bone 320. A surgeon implants the implant 5 using the implant insertion device 295 as previously described with reference to FIG. 52. However, prior to the removal of the implant 5 from the implant insertion device 295 after its insertion into the bone 320, the surgeon aligns an outlet of the bone augmentation material delivery device 325 with the cannulation 8 of the implant 5 and then actuates the bone augmentation material delivery device 325 to deliver the bone augmentation material 326 into the bone 320 via the cannulation 8. The bone augmentation material 326 enters the cannulation 8 via its inlet 10, traverses the cannulation 8, and then exits the cannulation 8 at its outlets 11 such that the bone augmentation material 326 enters the bone 320 pieces around the leg 21 and its tip 23. The surgeon aligns the outlet of the bone augmentation material delivery device 325 with the cannulation 9 of the implant 5 and then actuates the bone augmentation material delivery device 325 to deliver the bone augmentation material 326 into the bone 320 via the cannulation 9. The bone augmentation material 326 enters the cannulation 9 via its inlet 12, traverses the cannulation 9, and then exits the cannulation 9 at its outlets 11 such that the bone augmentation material 326 enters the bone 320 pieces around the leg 22 and its tip 24. The bone augmentation material 326 fills the bone 320 around the legs 21 and 22, and, once its sets or cures, the bone augmentation material 326 enhances the structural integrity of the bone 320.

After insertion of the implant 5 into the bone 320 and the subsequent delivery of the bone augmentation material 326 into the bone 320, the implant 5 is ready for removal from the implant insertion device 295. The surgeon progresses the slider 302 from its locked position to its unlocked position resulting in the slider 302 releasing the jaws 303-305, which travel from their engaged position to their disengaged position. The implant insertion device 295 accordingly transitions from its implant engagement position 297 to its implant disengagement position 296 whereby the implant 5 disengages from the implant insertion device 295 without obstruction thereby allowing the surgeon to remove the implant insertion device 295 from the implant 5. With the implant insertion device 295 disengaged from the implant 5, the surgeon tamps the implant 5 in abutting relationship with bone 320.

Once the implant 5 is released from the implant insertion device 295 and tamped into the bone 320, the implant 5 attempts to transition from its insertion shape 7 to its natural shape 6 such that the implant 5 through its compression or distraction of the bone 320 remains implanted in the bone 320 thereby holding the bone 320 in a desired alignment and assisting in the fixation and healing thereof. In particular, the bridge 14 attempts to transition from its insertion form to its natural form while the legs 21 and 22 attempt to move from their insertion position to their natural position. As illustrated in FIG. 54, the bone 320 due to its augmentation with the bone augmentation material 326 and corresponding increased structural integrity receives energy imparted thereto from the implant 5 without experiencing a structural failure that causes a loss of fixation and subsequent improper fusion or distraction thereof. The bone augmentation material accordingly augments the bone 320 resulting in the bone 320 arresting movement of the legs 21 and 22 from their insertion position to their natural position during an attempted transition of the bridge 14 from its insertion form to its natural form such that the implant 5 imparts a force sufficient to fuse or distract the bone 320.

In view of the foregoing embodiments illustrating an orthopedic implant according to the present invention, it should be understood that an orthopedic implant will fall within the scope of the present invention regardless of its body shape and number of legs provided the implant includes at least one cannulation. Moreover, although the present invention has been described in terms of the foregoing embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An apparatus for fixating bone, comprising:
an orthopedic implant comprised of a shape memory material and adapted for implantation into the bone, wherein the orthopedic implant is moveable between a natural shape and an insertion shape, the orthopedic implant, comprising:
a bridge,
a first leg extending from the bridge, the bridge and the first leg defining a first cannulation therethrough, whereby the first cannulation includes an inlet in the bridge and at least one outlet in the first leg, further whereby the first cannulation traverses the bridge and the first leg to deliver a bone augmentation material into the bone around the first leg,
a second leg extending from the bridge, the bridge and the second leg defining a second cannulation therethrough, whereby the second cannulation includes an inlet in the bridge and at least one outlet in the second leg, further whereby the second cannulation traverses the bridge and the second leg to deliver a bone augmentation material into the bone around the second leg, and
the first and second legs reside in a natural position when the orthopedic implant resides in its natural shape and in an insertion position when the orthopedic implant resides in its insertion shape; and
the orthopedic implant implants into the bone in its insertion shape such that the first and second legs implant into the bone in their insertion position with the bridge traversing a fixation zone of the bone, wherein, after implantation of the orthopedic implant, a bone augmentation material delivered into the bone via the first cannulation and the second cannulation augments the bone, further wherein the orthopedic implant attempts transition from its insertion shape to its natural shape while the first and second legs attempt transition from their insertion position to their natural position such that the orthopedic implant fixates the bone.

2. The apparatus for fixating bone according to claim 1, wherein the bridge comprises at least one transition section including a natural form when the orthopedic implant resides in its natural shape that locates the first and second legs in their natural position and an insertion form when the orthopedic implant resides in its insertion shape that locates the first and second legs in their insertion shape.

3. The apparatus for fixating bone according to claim 1, wherein:
the bridge includes a first end and a second end;
the first leg extends from the bridge adjacent its first end; and
the second leg extends from the bridge adjacent its second end.

4. The apparatus for fixating bone according to claim 3, comprising:
a third leg extending from the bridge between the first leg and a central axis of the bridge, wherein the bridge and the third leg define a third cannulation adapted to deliver a bone augmentation material to the bone; and
a fourth leg extending from the bridge between the second leg and a central axis of the bridge, wherein the bridge and the fourth leg define a fourth cannulation adapted to deliver a bone augmentation material to the bone.

5. The apparatus for fixating bone according to claim 4, wherein:

the third cannulation includes an inlet in the bridge and at least one outlet in the third leg whereby the third cannulation traverses the bridge and the third leg to deliver a bone augmentation material into the bone around the third leg; and the fourth cannulation includes an inlet in the bridge and at least one outlet in the fourth leg whereby the fourth cannulation traverses the bridge and the fourth leg to deliver a bone augmentation material into the bone around the fourth leg.

6. The apparatus for fixating bone according to claim 3, comprising a third leg extending from the bridge at its first end, wherein the third leg resides adjacent the first leg, further wherein the bridge and the third leg define a third cannulation adapted to deliver a bone augmentation material to the bone.

7. The apparatus for fixating bone according to claim 6, wherein the third cannulation includes an inlet in the bridge and at least one outlet in the third leg whereby the third cannulation traverses the bridge and the third leg to deliver a bone augmentation material into the bone around the third leg.

8. The apparatus for fixating bone according to claim 6, comprising a fourth leg extending from the bridge at its second end, wherein the fourth leg resides adjacent the second leg, further wherein the bridge and the fourth leg define a fourth cannulation adapted to deliver a bone augmentation material to the bone.

9. The apparatus for fixating bone according to claim 8, wherein the fourth cannulation includes an inlet in the bridge and at least one outlet in the fourth leg whereby the fourth cannulation traverses the bridge and the fourth leg to deliver a bone augmentation material into the bone around the fourth leg.

10. The apparatus for fixating bone according to claim 3, wherein:
the bridge includes a first aperture adjacent a first end thereof adapted to receive therethrough a fixation device that engages the bone;
the bridge includes a second aperture adjacent a second end thereof adapted to receive therethrough a fixation device that engages the bone;
the first leg extends from the bridge between the first aperture and a central axis of the bridge; and
the second leg extends from the bridge between the second aperture and a central axis of the bridge.

11. An orthopedic implant for fixating bone, the orthopedic implant comprising a shape memory material and adapted for implantation into the bone, whereby the orthopedic implant is moveable between a natural shape and an insertion shape, the orthopedic implant, comprising:
a bridge;
a first leg extending from the bridge;
a second leg extending from the bridge, wherein the first and second legs reside in a natural position when the orthopedic implant resides in its natural shape, further wherein the first and second legs reside in an insertion position when the orthopedic implant resides in its insertion shape;
the bridge and the first leg defining a first cannulation adapted to deliver a bone augmentation material to the bone, whereby the first cannulation includes an inlet in the bridge and at least one outlet in the first leg, further whereby the first cannulation traverses the bridge and the first leg to deliver the bone augmentation material into the bone around the first leg;

the bridge and the second leg defining a second cannulation adapted to deliver a bone augmentation material to the bone, whereby the second cannulation includes an inlet in the bridge and at least one outlet in the second leg, further whereby the second cannulation traverses the bridge and the second leg to deliver the bone augmentation material into the bone around the second leg; and the first and second legs implant into the bone in their insertion position with the bridge traversing a fixation zone of the bone, wherein, after implantation of the orthopedic implant:
a bone augmentation material delivered into the bone via the first and second cannulations augments the bone, and
the orthopedic implant attempts transition from its insertion shape to its natural shape whereby the first and second legs attempt movement from their insertion position to their natural position such that the orthopedic implant fixates the bone.

12. The orthopedic implant for fixating bone according to claim 11, wherein the bridge comprises at least one transition section including a natural form when the orthopedic implant resides in its natural shape that locates the first and second legs in their natural position and an insertion form when the orthopedic implant resides in its insertion shape that locates the first and second legs in their insertion shape.

13. The orthopedic implant for fixating bone according to claim 11, wherein:
the bridge includes a first end and a second end;
the first leg extends from the bridge adjacent its first end; and
the second leg extends from the bridge adjacent its second end.

14. The orthopedic implant for fixating bone according to claim 13, comprising:
a third leg extending from the bridge between the first leg and a central axis of the bridge, wherein the bridge and the third leg define a third cannulation adapted to deliver a bone augmentation material to the bone; and
a fourth leg extending from the bridge between the second leg and a central axis of the bridge, wherein the bridge and the fourth leg define a fourth cannulation adapted to deliver a bone augmentation material to the bone.

15. The orthopedic implant for fixating bone according to claim 14, wherein:
the third cannulation includes an inlet in the bridge and at least one outlet in the third leg whereby the third cannulation traverses the bridge and the third leg to deliver a bone augmentation material into the bone around the third leg; and
the fourth cannulation includes an inlet in the bridge and at least one outlet in the fourth leg whereby the fourth cannulation traverses the bridge and the fourth leg to deliver a bone augmentation material into the bone around the fourth leg.

16. The orthopedic implant for fixating bone according to claim 13, comprising a third leg extending from the bridge at its first end, wherein the third leg resides adjacent the first leg, further wherein the bridge and the third leg define a third cannulation adapted to deliver a bone augmentation material to the bone.

17. The orthopedic implant for fixating bone according to claim 16, wherein the third cannulation includes an inlet in the bridge and at least one outlet in the third leg whereby the third cannulation traverses the bridge and the third leg to deliver a bone augmentation material into the bone around the third leg.

18. The orthopedic implant for fixating bone according to claim 16, comprising a fourth leg extending from the bridge at its second end, wherein the fourth leg resides adjacent the second leg, further wherein the bridge and the fourth leg define a fourth cannulation adapted to deliver a bone augmentation material to the bone.

19. The orthopedic implant for fixating bone according to claim 18, wherein the fourth cannulation includes an inlet in the bridge and at least one outlet in the fourth leg whereby the fourth cannulation traverses the bridge and the fourth leg to deliver a bone augmentation material into the bone around the fourth leg.

20. The orthopedic implant for fixating bone according to claim 13, wherein:
- the bridge includes a first aperture adjacent a first end thereof adapted to receive therethrough a fixation device that engages the bone;
- the bridge includes a second aperture adjacent a second end thereof adapted to receive therethrough a fixation device that engages the bone;
- the first leg extends from the bridge between the first aperture and a central axis of the bridge; and
- the second leg extends from the bridge between the second aperture and a central axis of the bridge.

* * * * *